United States Patent
Gow et al.

(10) Patent No.: US 11,306,138 B2
(45) Date of Patent: Apr. 19, 2022

(54) ANTIBODY MOLECULES AND USES THEREOF

(71) Applicant: THE UNIVERSITY COURT OF THE UNIVERSITY OF ABERDEEN, Aberdeen (GB)

(72) Inventors: Neil Andrew Robert Gow, Aberdeen (GB); Fiona Marion Rudkin, Aberdeen (GB); Lars-Peter Erwig, Blunham (GB); Allan Jensen, Frederiksberg (DK)

(73) Assignee: THE UNIVERSITY COURT OF THE UNIVERSITY OF ABERDEEN, Aberdeen (GB)

( * ) Notice: Subject to any disclaimer, the term of this patent is extended or adjusted under 35 U.S.C. 154(b) by 361 days.

(21) Appl. No.: 15/556,145

(22) PCT Filed: Mar. 4, 2016

(86) PCT No.: PCT/GB2016/050577
§ 371 (c)(1),
(2) Date: Sep. 6, 2017

(87) PCT Pub. No.: WO2016/142660
PCT Pub. Date: Sep. 15, 2016

(65) Prior Publication Data
US 2018/0037640 A1 Feb. 8, 2018

(30) Foreign Application Priority Data
Mar. 6, 2015 (GB) .................... 1503812

(51) Int. Cl.
*C07K 16/14* (2006.01)
*G01N 33/569* (2006.01)
*A61K 39/395* (2006.01)
*A61K 45/06* (2006.01)
*A61K 39/00* (2006.01)

(52) U.S. Cl.
CPC ........ *C07K 16/14* (2013.01); *A61K 39/39575* (2013.01); *A61K 45/06* (2013.01); *G01N 33/56961* (2013.01); *A61K 2039/505* (2013.01); *C07K 2317/21* (2013.01); *C07K 2317/33* (2013.01); *C07K 2317/52* (2013.01); *C07K 2317/56* (2013.01); *C07K 2317/565* (2013.01); *C07K 2317/92* (2013.01); *G01N 2333/40* (2013.01); *G01N 2469/10* (2013.01)

(58) Field of Classification Search
None
See application file for complete search history.

(56) References Cited

U.S. PATENT DOCUMENTS

| 7,241,613 B1 | 7/2007 | Willins et al. |
| 2003/0124134 A1 | 7/2003 | Edwards et al. |
| 2009/0081196 A1 | 3/2009 | Cassone |

FOREIGN PATENT DOCUMENTS

| WO | WO 2000/48633 | 8/2000 |
| WO | WO 2013/040478 | 3/2013 |

OTHER PUBLICATIONS

Bendig (Methods: A Companion to Methods in Enzymology 1995; 8:83-93).*
Kussie et al (1994).*
Chen et al, (1995).*
Chien et al (PNAS 86:5532-5536, 1989).*
Chiu et al (Antibodies 8(55):1-80, 2019).*
Lu et al (Nat. Rev. Immunology 18(1):46-61, 2018).*
Bailey, D.A. et al. "The Candida albicans HYR1 gene, which is activated in response to hyphal development, belongs to a gene family encoding yeast cell wall proteins" (1996) J. of Bacteriology 178(18):5353-5360.
Bliss, J.M. et al. "Differentiation of Candida albicans and Candida dubliniensis by Using Recombinant Human Antibody Single-Chain Variable Fragments Specific for Hypha" (2003) J. of Clinical Microbiology 41(3):1152-1160.
Casadevall, A. et al. "Immunoglobulins in Defense, Pathogenesis, and Therapy of Fungal Disease" (2012) Cell Host & Microbe 11(5):447-456.
Haidaris, C. et al. "Recombinant human antibody single chain variable fragments reactive with Candida albicans surface antigens" (2001) J. of Immunological Methods 257:185-202.
Laforce-Nesbitt, S.S. et al. "Inhibition of Candida albicans adhesion by recombinant human antibody single-chain variable fragment specific for Als3p" (2008) FEMS Immunology and Medical Microbiology 54(2):195-202.
Meijer, P.J., et al. "Isolation of Human Antibody Repertoires with Preservation of the Natural Heavy and Light Chain Pairing" (2006) J. of Molecular Biology 358(3):764-772.
Meijer, P.J., et al. "Human antibody repertoires" (2009) Methods in Molecular Biology 525:261-277.
Wilson, P., et al. "Tools to therapeutically harness the human antibody response" (2012) J. Immunology 12(10):709-719.
International Search Report and Written Opinion for PCT/GB2016/050577, dated Jul. 20, 2016 (25 pages).

(Continued)

*Primary Examiner* — Patricia Duffy
(74) *Attorney, Agent, or Firm* — Quarles & Brady LLP

(57) ABSTRACT

This invention relates to recombinant human antibody molecules. The antibodies bind fungal antigens, for example from *Candida* spp. Human antibody encoding genes targeting clinically relevant *Candida* epitopes have been isolated from single B cells from carefully selected donors and screened with specified types of protein or cell wall extract. The panel of purified, fully human recombinant IgG1 mAbs generated displayed a diverse range of specific binding profiles and demonstrated efficacy in a disease model. The fully human mAbs and derivatives thereof have utility in the generation of diagnostics, therapeutics and vaccines.

14 Claims, 27 Drawing Sheets

Specification includes a Sequence Listing.

(56) References Cited

OTHER PUBLICATIONS

Rudkin, F.M., et al., "Single human B cell-derived monoclonal anti-*Candida* antibodies enhance phagocytosis and protect against disseminated candidiasis", Nature Communications, 2018, 9(5288): 1-16, doi:org/10.1038/s41467-018-07738-1.

International Preliminary Report on Patentability for International Patent Application No. PCT/GB2016/050577 dated Sep. 21, 2017 (15 pages).

* cited by examiner

Figure 2:
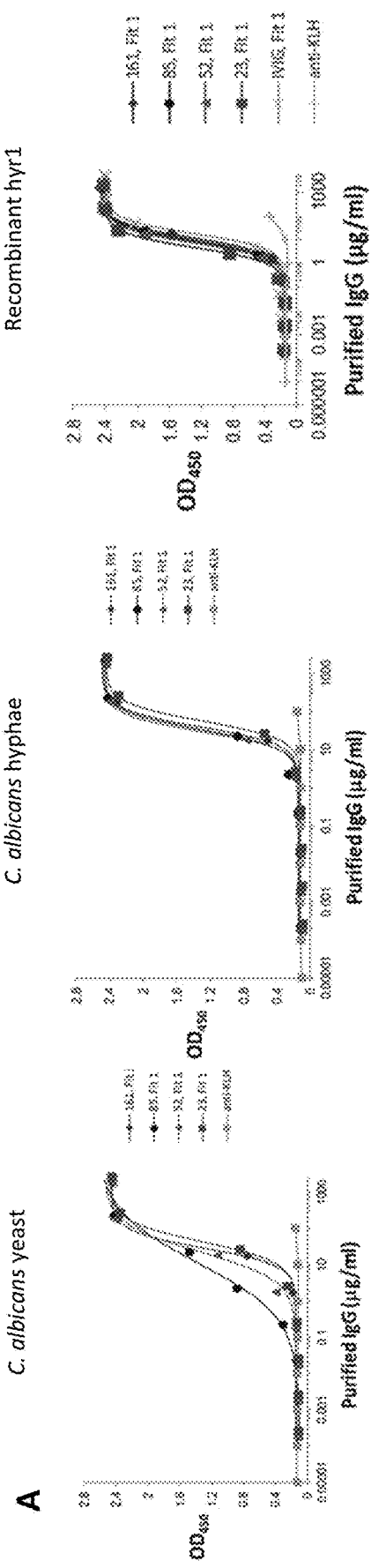
Figure 2:
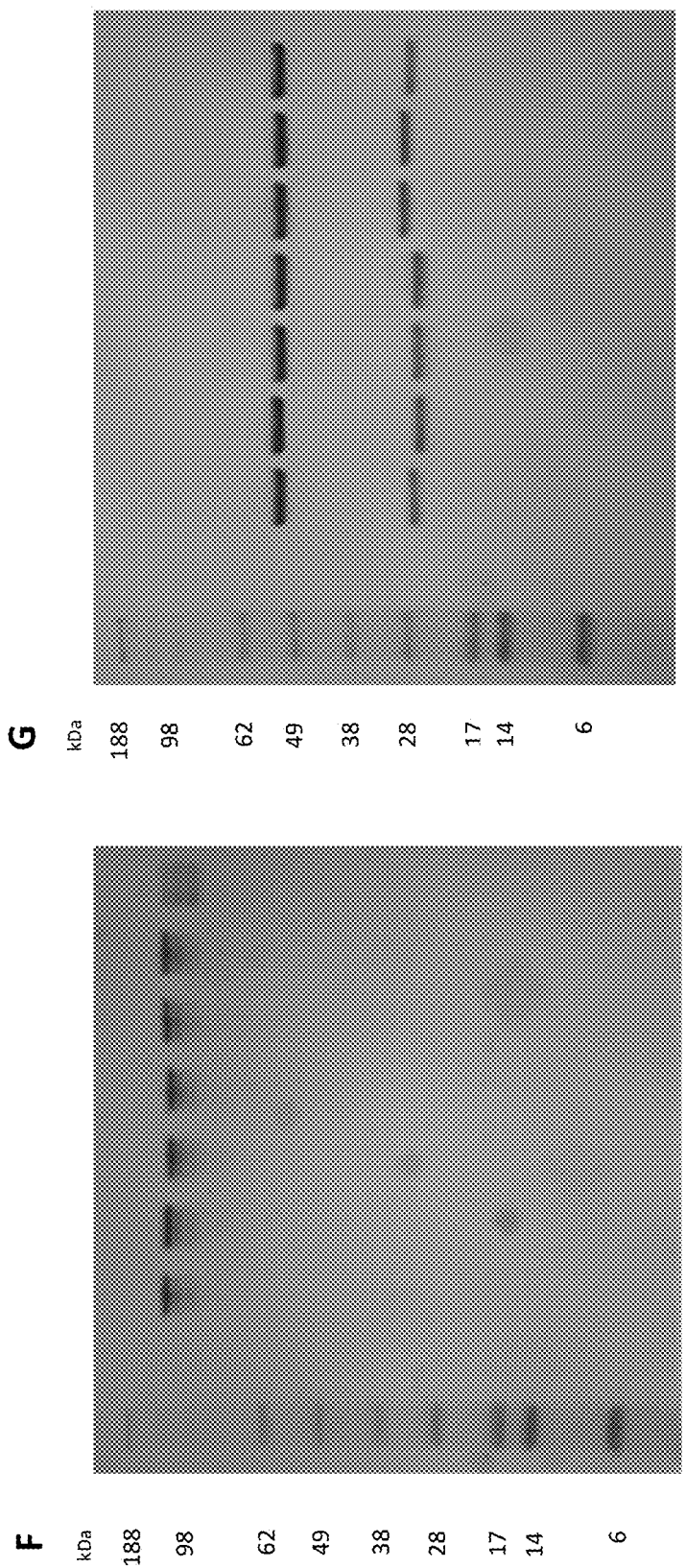

Figure 2
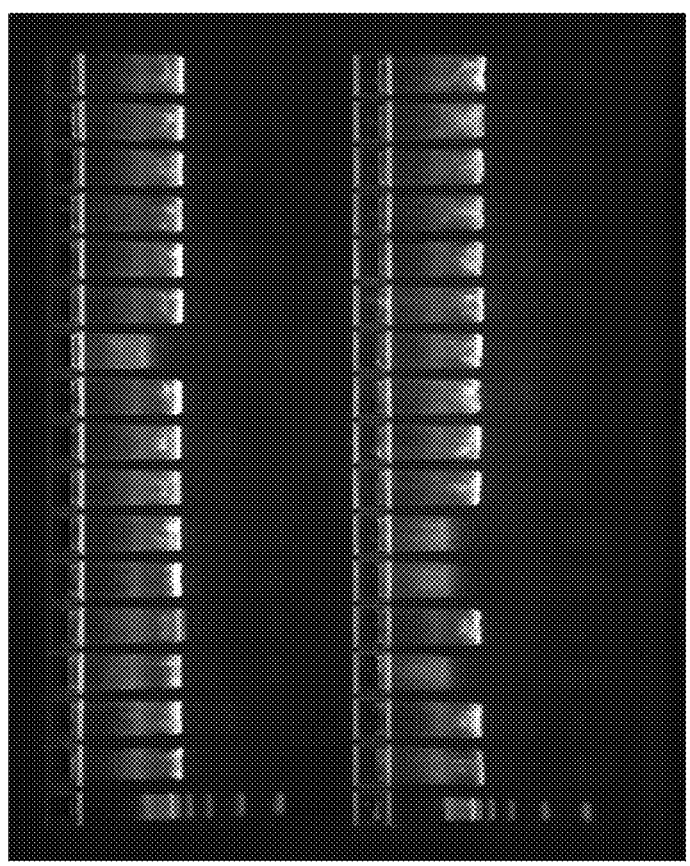
C
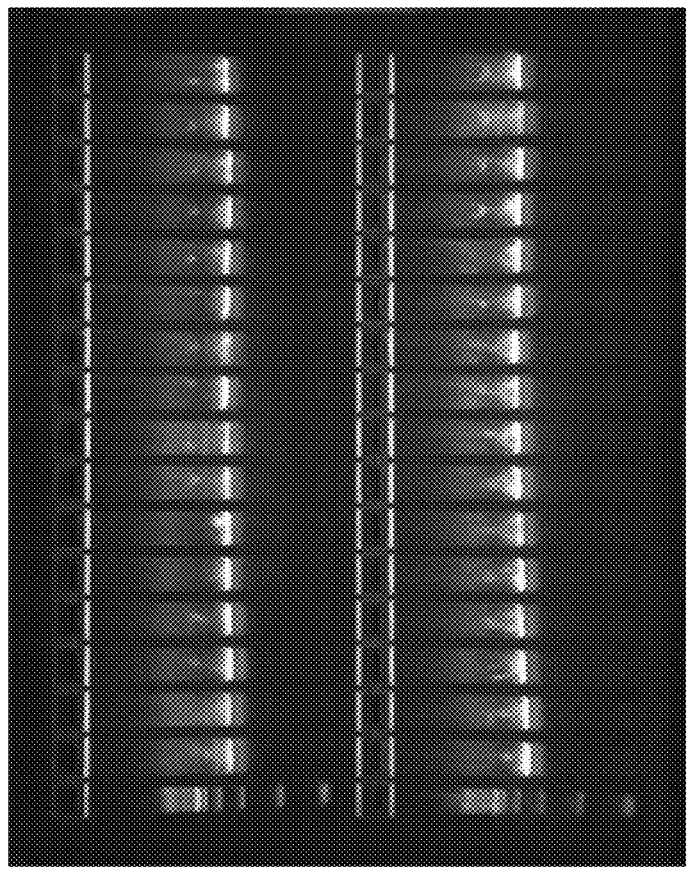
B

Figure 2
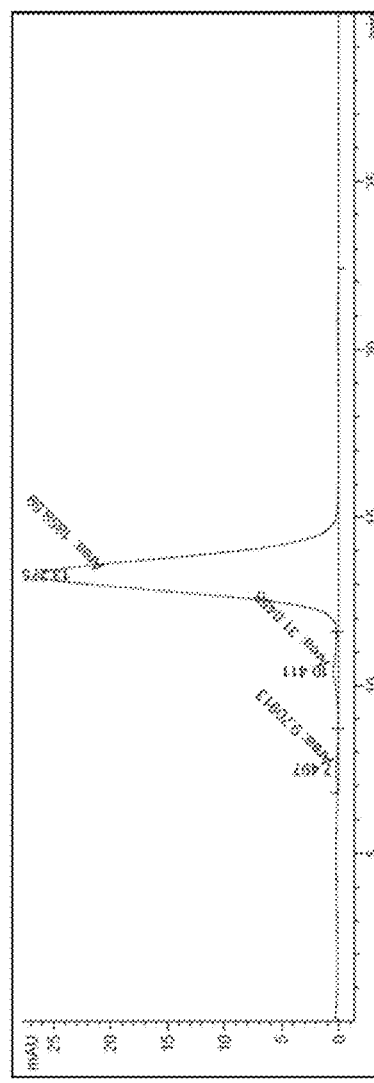
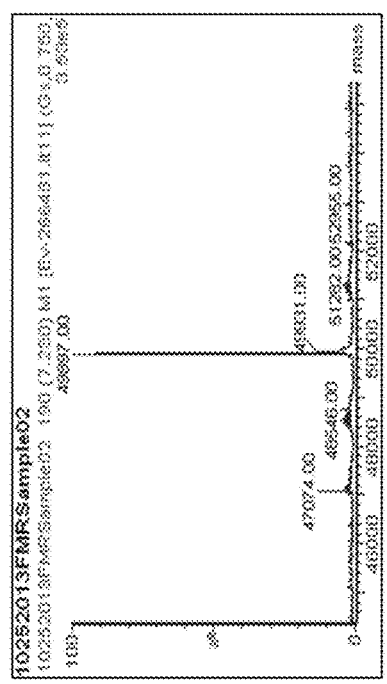

Figure 6

A

| Antibody | C. albicans | C. dubliniensis | C. glabrata | C. tropicalis | C. parapsilosis | C. krusei | C. lusitaniae |
|---|---|---|---|---|---|---|---|
| AB120 | ++++++++ | --- | - | --- | --- | - | --- |
| AB121 | ++++++++ | --- | - | --- | --- | - | --- |
| AB122 | ++++++++ | --- | - | --- | --- | - | --- |
| AB123 | ++++++++ | --- | - | --- | --- | - | --- |

B

| mAb | C. albicans | C. dubliniensis | C. tropicalis | C. parapsilosis | C. lusitaniae | C. auris | C. haemulonii | C. glabrata | C. krusei | A. fumigatus | C. neoformans | C. gattii | P. carinii | M. dermatis | M. circinelloides |
|---|---|---|---|---|---|---|---|---|---|---|---|---|---|---|---|
| AB118 | ++++++++ | ++++++++ | ++++++++ | ++++++++ | ++++++++ | ++++++++ | ++++++++ | //////// | --- | --- | --- | --- | --- | --- | --- |
| AB119 | ++++++++ | ++++++++ | ++++++++ | ++++++++ | ++++++++ | ++++++++ | ++++++++ | //////// | --- | --- | --- | --- | --- | --- | --- |
| AB126 | //////// | //////// | //////// | //////// | ======== | ######## | //////// | //////// | ######## | --- | --- | --- | --- | --- | --- |
| AB127 | ++++++++ | ++++++++ | ++++++++ | ######## | ++++++++ | ######## | ======== | --- | --- | --- | --- | --- | --- | --- | --- |
| AB129 | //////// | //////// | //////// | //////// | ++++++++ | //////// | //////// | //////// | ======== | --- | --- | --- | --- | --- | --- |
| AB131 | //////// | ======== | //////// | //////// | //////// | //////// | ######## | ######## | //////// | --- | --- | --- | --- | --- | --- |
| AB132 | ++++++++ | ++++++++ | ++++++++ | ++++++++ | ++++++++ | ======== | //////// | //////// | --- | --- | --- | --- | --- | --- | --- |
| AB133 | //////// | ++++++++ | //////// | //////// | //////// | ######## | ######## | //////// | --- | --- | --- | --- | --- | --- | --- |
| AB134 | ++++++++ | ++++++++ | ++++++++ | ++++++++ | ++++++++ | --- | ++++++++ | //////// | --- | --- | --- | --- | --- | --- | --- |
| AB135 | //////// | ++++++++ | //////// | ++++++++ | ++++++++ | ######## | ######## | //////// | --- | --- | --- | --- | --- | --- | --- |
| AB139 | ++++++++ | ++++++++ | ++++++++ | ++++++++ | ++++++++ | ++++++++ | ++++++++ | //////// | --- | --- | --- | --- | --- | --- | --- |
| AB140 | ++++++++ | ++++++++ | ++++++++ | ++++++++ | ++++++++ | ++++++++ | ++++++++ | //////// | --- | --- | --- | --- | --- | --- | --- |

Strong binding ← ++++++++ | //////// | ######## | ======== | --- → No binding

Figure 10:
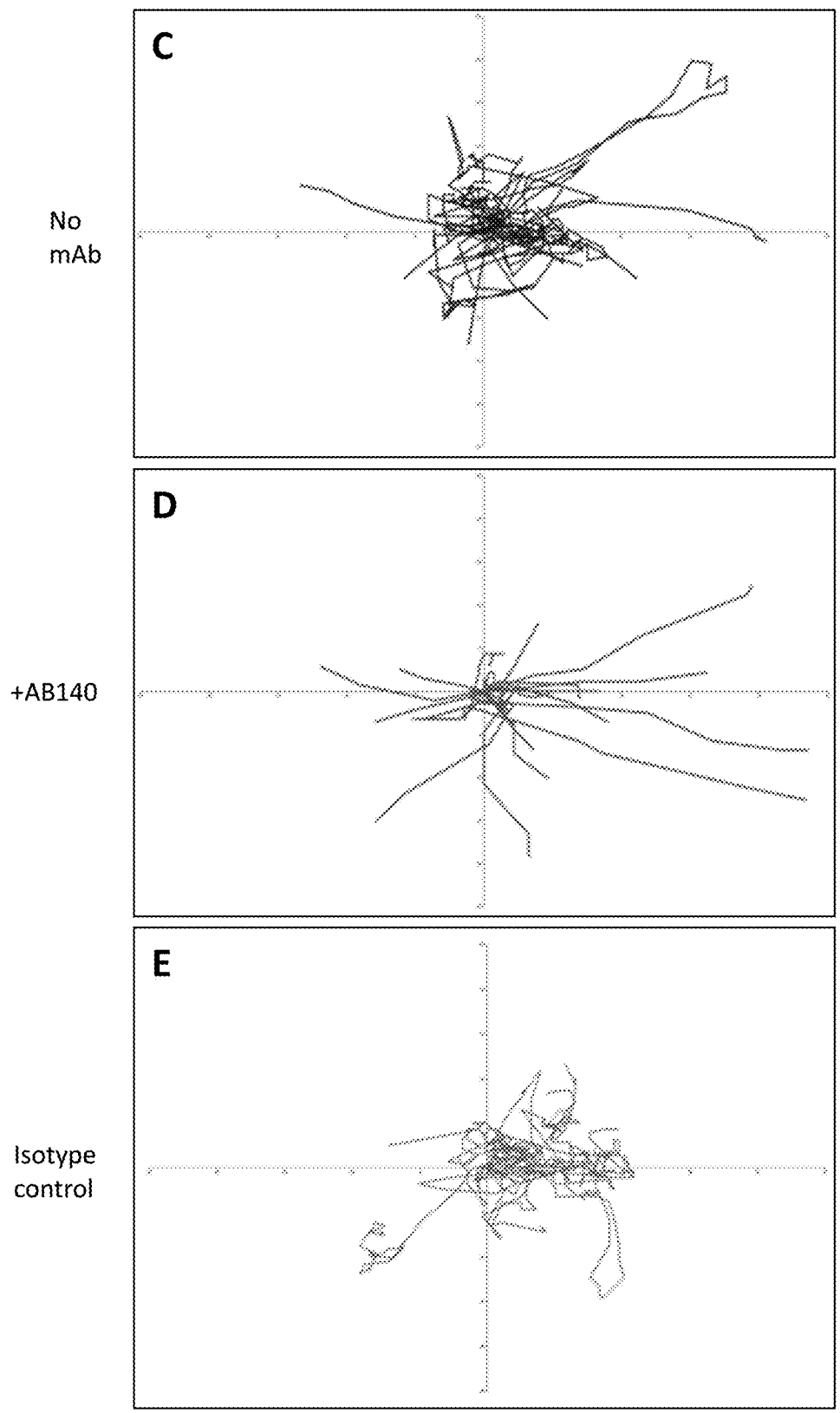

Figure 10
A
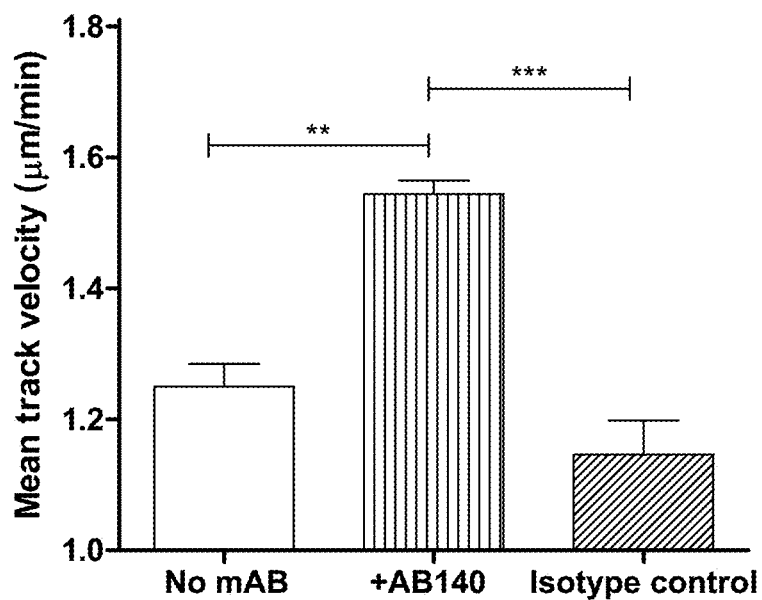
B
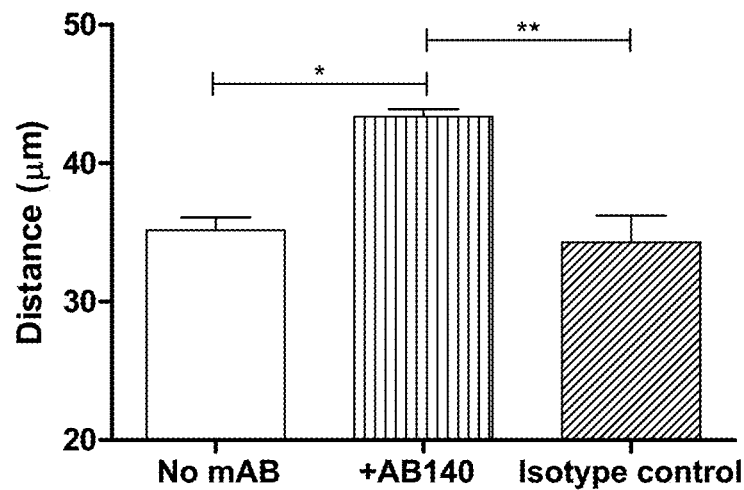

Figure 11
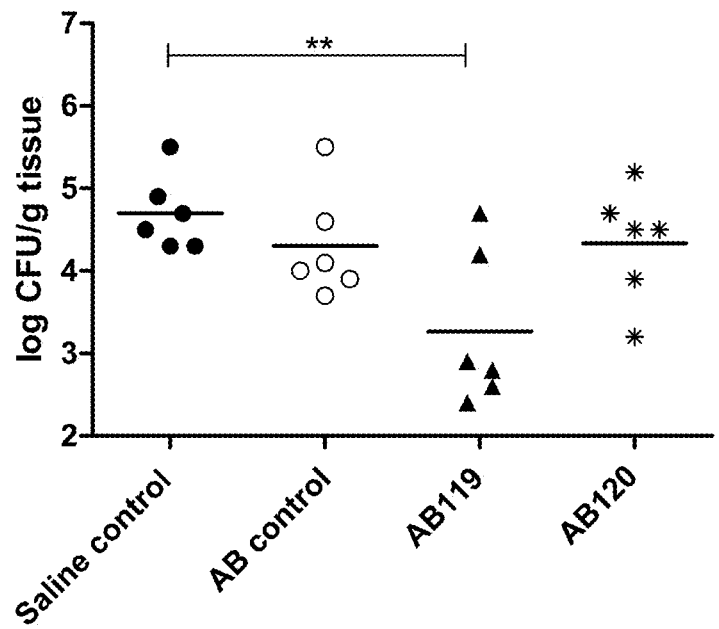
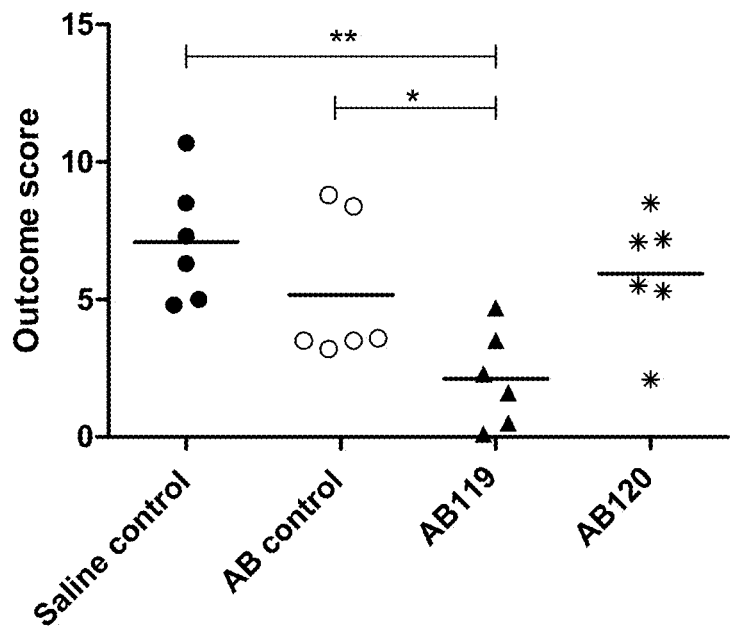

A

Figure 16:
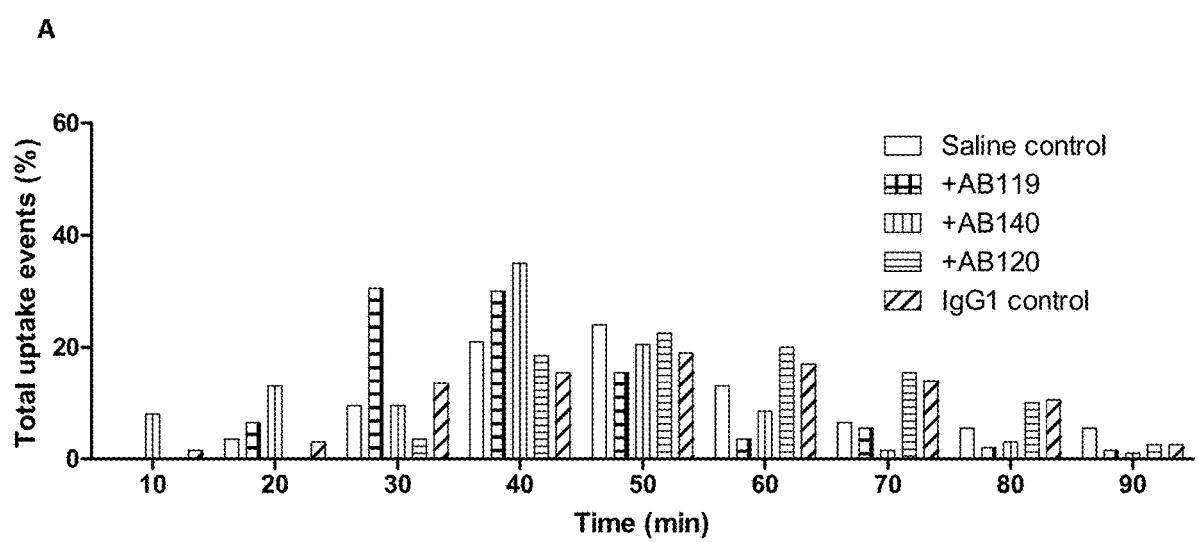

Figure 16
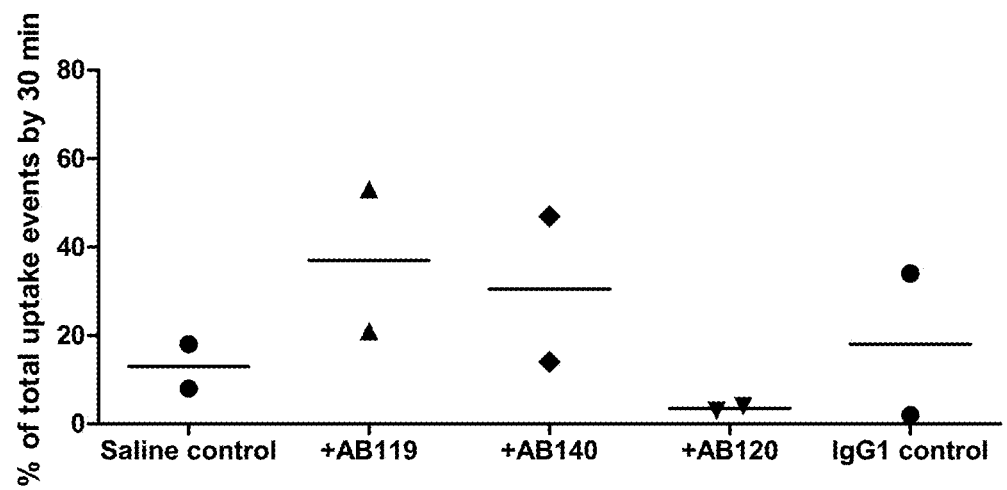
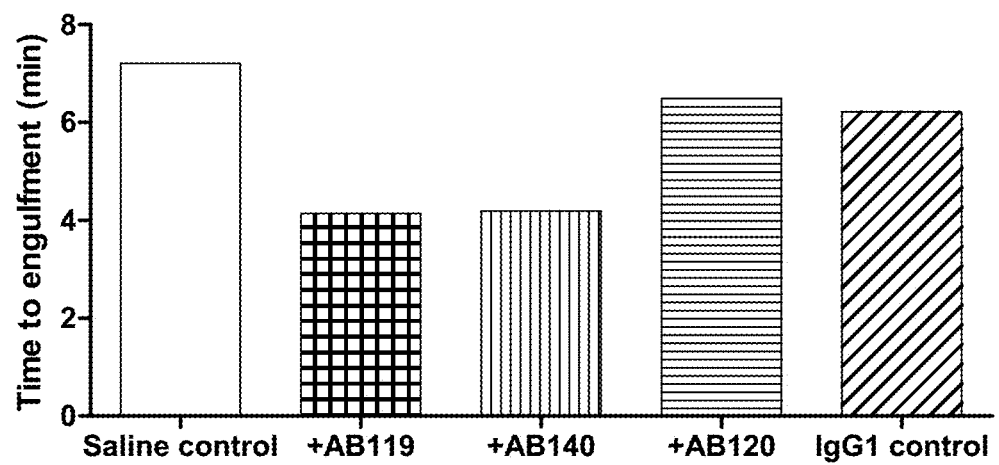

Figure 17
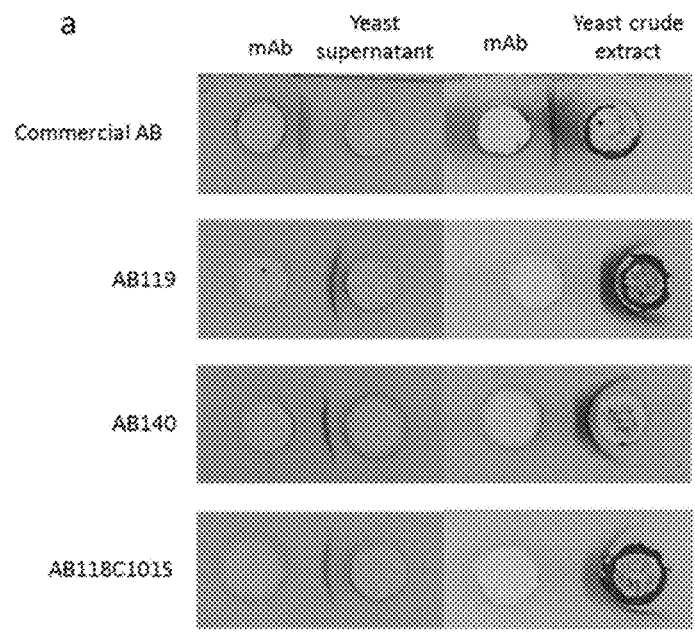
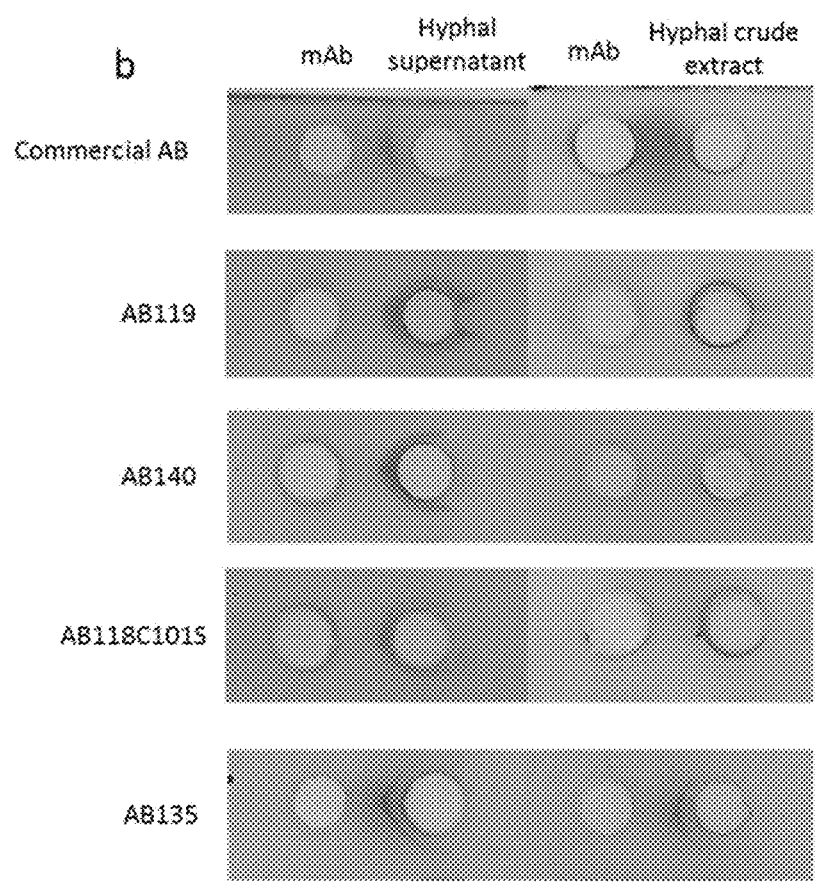

ANTIBODY MOLECULES AND USES THEREOF

CROSS-REFERENCE TO RELATED APPLICATIONS

This patent application is a national stage filing under 35 U.S.C. 371 of International Application No. PCT/GB2016/050577, filed Mar. 4, 2016, which claims the benefit of priority of United Kingdom Patent Application No. 1503812.8, filed Mar. 6, 2015, both of which are incorporated herein by reference in their entirety.

TECHNICAL FIELD

This invention relates to recombinant human antibody molecules. The antibodies bind fungal antigens, for example from *Candida* spp. Such antibody molecules find use in the treatment, diagnosis and/or detection of fungal infections.

BACKGROUND ART

Fungi cause 3 million life-threatening infections each year, killing more people than tuberculosis and as many people as malaria (1). To make inroads into these high disease burdens and mortality figures, better diagnostics, treatments and fungal vaccines are urgently required.

*Candida* species collectively account for the majority of serious fungal infections and represent the fourth leading cause of healthcare-associated infections in the US (1, 2).

*Candida albicans* is a common human commensal and the most prevalent fungal opportunistic pathogen (3). *C. albicans* is polymorphic, phenotypically variable and genetically diverse. Impairment of host immunity, due to mutation, pharmacological or surgical intervention, trauma or alteration in the natural microbiota, determines the frequency and severity of disease (4). Late diagnosis of invasive candidiasis using 'gold standard' blood culture methodologies and limitations in the versatility and accuracy if some diagnostic tests contribute to the overall poor prognosis and high mortality rates associated with septicaemia and invasive fungal disease (5-7).

Existing classes of antifungals are effective against infection but tend to have relatively narrow spectra of activity that means that informed therapy is predicated on accurate diagnosis (2, 8).

There are currently no vaccines for fungal infection in the clinic although experimental vaccines based on fungal cell wall targets are in pre-clinical development (20, 22-27). These include the investigational vaccine NDV-3 based on a recombinant fragment of the Als3 cell wall adhesin which has now entered phase II clinical trials for recurrent vulvovaginal candidiasis (RVVC) (26, 28) and a *Candida*-specific vaccine based on the recombinant N-terminal fragment of the Hyr1 protein expressed on *C. albicans* hyphae which has shown efficacy in a murine model of disseminated candidiasis (23, 29). These experimental vaccines exert their protective effects by eliciting neutralising and/or protective antibodies (23).

Protective monoclonal antibody (mAbs) for clinically relevant fungi have been reported (15-17). A number of protective mAbs targeting pan fungal and species-specific epitopes have been isolated, which are almost exclusively murine in origin, and generated via hybridoma technology (15, 18-22).

Increased mAb research in the field of mycotic disease has also led to progress in mAb-based diagnostics including the *Aspergillus*-specific mAb JF5 for the detection of invasive pulmonary aspergillosis (IPA), a *C. albicans* germ tube antibody (CAGTA) for deep-seated *Candida* infection and a new cryptococcal dipstick antigen test (30-33).

Nevertheless it can be seen that novel sources of diagnostic and therapeutic reagents targeting fungal pathogens would provide a contribution to the art.

DISCLOSURE OF THE INVENTION

The present invention seeks to provide novel diagnostics and therapeutics for fungal infections, through a mAb-based approach using *C. albicans* as the model organism.

The inventors have isolated human antibody encoding genes targeting clinically relevant *Candida* epitopes from single B cells that were derived from donors with a history of mucosal *Candida* infections screened with recombinant *Candida albicans* Hyr1 cell wall protein or whole fungal cell wall extracts. The panel of purified, fully human recombinant IgG1 mAbs generated displayed a diverse range of specific binding profiles to other pathogenic fungi and demonstrated efficacy in a murine model of disseminated candidiasis. The fully human mAbs have utility in the generation of diagnostics, therapeutics and vaccines.

In various aspects of the invention there are provided isolated recombinant human anti-*Candida* antibody molecule derived from single B cells, for example which specifically bind *Candida* cells or more specifically *C. albicans* hyphae.

Preferred antibody molecules have CDRs, FWs, VH and VL domains having sequences set out in Tables A-R, each Table being the sequence of one of the 18 antibodies of the Examples, or derivatives of those sequences having one or more amino acid substitutions, deletions or insertions.

Also provided are methods for producing an antibody antigen-binding domain for a fungal antigen, or for producing an antibody molecule that specifically binds to a fungal antigen, which methods comprise utilising or modifying one or more of the CDRs, FWs, VH and VL domains having sequences set out in Tables A-R.

Also provided are methods of identifying or labelling a *Candida* cell, or the hyphae of *C. albicans*, of opsonising, or increasing the rate of opsonisation of a *Candida* cell, of increasing the rate of engulfment of a *Candida* cell, or of increasing the rate of macrophage attraction to *Candida* cell, the methods utilising the antibody molecules of the invention.

The invention also provides therapeutic and diagnostic utilities for the antibody molecules of the invention, and diagnostic devices utilising them.

Some of these aspects and embodiments of the invention will now be described in more detail.

mAbs and Processes of Production

Pooled immunoglobulin from serum was one of the first widely available treatments for microbial infections and that hyperimmune human sera immunoglobulin is still used today to treat a number of infections including cytomegalovirus (CMV), hepatitis A and B virus (HAV, HBV) rabies and measles (12-14). Nevertheless, although in recent years humanised versions of mAbs have become some of the world's bestselling drugs, to date the majority of these mAbs have been licensed for the treatment of cancer and autoimmune diseases (9-11), there is currently only one mAb approved for the treatment of an infectious disease (13).

Methods for the production of mAbs for therapeutic and/or diagnostic use have diversified dramatically over the decades. Early mAbs were mainly of murine origin but tended to be immunogenic in the human host (34, 35). The majority of mAbs currently in the clinics are humanized or fully human IgG1 mAbs generated through hybridoma cell lines (14, 35). Combinatorial display technologies using phage or yeast have been valuable but require a period of in vitro affinity maturation and lose the natural antibody heavy and light chain pairings (14).

Recently, direct amplification of individual VH and VL chain domain genes from single human B cells to ensure retention of native antibody heavy and light chain pairings, has led to the generation of fully human mAbs with increased safety and relevance to human disease in areas where current treatments are suboptimal (14, 36-39).

Antibody Molecules

Anti-*Candida* recombinant human antibody molecules of the invention may include any polypeptide or protein comprising an antibody antigen-binding site described herein, including Fab, $Fab_2$, $Fab_3$, diabodies, triabodies, tetrabodies, minibodies and single-domain antibodies, as well as whole antibodies of any isotype or sub-class.

The anti-*Candida* recombinant human antibody molecules may also be a single-chain variable fragment (scFv) or single-chain antibody (scAb). An scFv fragment is a fusion of a variable heavy (VH) and variable light (VL) chain. A scAb has a constant light (CL) chain fused to the VL chain of an scFv fragment. The CL chain is optionally the human kappa light chain (HuCK). A single chain Fv (scFv) may be comprised within a mini-immunoglobulin or small immunoprotein (SIP), e.g. as described in Li et al. (1997). An SIP may comprise an scFv molecule fused to the CH4 domain of the human IgE secretory isoform IgE-S2 ($\varepsilon_{S2}$—CH4; Batista, F. D., Anand, S., Presani, G., Efremov, D. G. and Burrone, O. R. (1996). The two membrane isoforms of human IgE assemble into functionally distinct B cell antigen receptors. *J. Exp. Med.* 184:2197-2205) forming an homo-dimeric mini-immunoglobulin antibody molecule.

Antibody molecules and methods for their construction and use are described, in for example, Holliger, P. and Hudson, P. J. (2005). Engineered antibody fragments and the rise of single domains. *Nat. Biotechnol.* 23:1126-1136.

Anti-*Candida* recombinant human antibody molecules as described herein may lack antibody constant regions.

However in some preferred embodiments, the anti-*Candida* recombinant human antibody molecule of the invention is a whole antibody. For example, the anti-*Candida* recombinant human antibody molecule may be an IgG, IgA, IgE or IgM or any of the isotype sub-classes, particularly IgG1.

Anti-*Candida* recombinant human antibody molecules as described will generally be provided in isolated form, in the sense of being free from contaminants, such as antibodies able to bind other polypeptides and/or serum components.

Anti-*Candida* recombinant human antibody molecules of the invention may be obtained in the light of the disclosure herein, for example using techniques described in reference (14).

Antibody molecules of the invention typically comprise an antigen binding domain comprising an immunoglobulin heavy chain variable domain (VH) and an immunoglobulin light chain variable domain (VL).

Each of the VH and VL domains typically comprise 3 complementarity determining regions (CDRs) responsible for antigen binding, interspersed by 4 framework (FW) regions.

In Tables A-R hereinafter, the sequences of each of the CDRs and FWs for each of the VH and VL domains is given for each of the preferred 18 antibodies of the invention i.e. Antibodies 120-124 (directed to the Hyr1 protein), and also 118-119, 126-127, 129-135, and 139-140 (directed to *C. albicans* 'whole cell'):

Tables VH and VL give the entire VH and VL domains of these 18 antibodies.

In these tables, each antibody the sequences are numbered as follows:

| | |
|---|---|
| 1x | H FW1 |
| 2x | H CDR1 |
| 3x | H FW2 |
| 4x | H CDR2 |
| 5x | H FW3 |
| 6x | H CDR3 |
| 7x | H FW4 |
| 8x | L FW1 |
| 9x | L CDR1 |
| 10x | L FW2 |
| 11x | L CDR2 |
| 12x | L FW3 |
| 13x | L CDR3 |
| 14x | L FW4 |
| 15x | VH full sequence |
| 16x | VL full sequence |

Tables "VH-CDR3-mod" and "VL-CDR3-mod" show pairs of variants of the CDR3 sequences of some of the VH domains (i.e. SEQ ID No 6x) and VL domains (SEQ ID No 13x) respectively. These VH-CDR3 variants are numbered SEQ ID Nos 17x/18x and these VL-CDR3 variants are numbered SEQ ID No 19x/20x.

In each case 'x' represents any single letter of A-R, each letter representing one of the 18 antibodies 118-124, 126-127, 129-135, and 139-140, for example 'A' represents antibody AB119 described in Table A and Tables VH and VL. It will be understood that the description in relation to sequence 'x' applies mutatis mutandis to any of the antibodies described in Tables A-R, as if that description was written individually for each antibody.

In some embodiments, Anti-*Candida* recombinant human antibody molecules of the invention may binding to the target wholly or substantially through a VHCDR3 sequence described herein.

Thus, for example, an anti-*Candida* recombinant human antibody molecule may comprise a VH domain comprising a HCDR3 having the amino acid sequence of SEQ ID NO: 6x or the sequence of SEQ ID NO: 6x with 1 or more, for example 2, or 3 or more amino acid substitutions, deletions or insertions (e.g. as shown in SEQ ID NO: 17x or 18x).

Substitutions as described herein may be conservative substitutions or may be present to remove Cys residues from the native sequence. In some embodiments, an antibody may comprise one or more substitutions, deletions or insertions which remove a glycosylation site.

The HCDR3 may be the only region of the antibody molecule that interacts with a target epitope or substantially the only region. The HCDR3 may therefore determine the specificity and/or affinity of the antibody molecule for the target.

The VH domain of an anti-*Candida* recombinant human antibody molecule may additionally comprise an HCDR2 having the amino acid sequence of SEQ ID NO: 4x or the sequence of SEQ ID NO: 4x with 1 or more, for example 2, or 3 or more amino acid substitutions, deletions or insertions.

The VH domain of an anti-*Candida* recombinant human antibody molecule may further comprise an HCDR1 having the amino acid sequence of SEQ ID NO: 2x or the sequence of SEQ ID NO: 2x with 1 or more, for example 2 or 3 or more amino acid substitutions, deletions or insertions.

In some embodiments, an antibody molecule may comprise a VH domain comprising a HCDR1, a HCDR2 and a HCDR3 having the sequences of SEQ ID NOs 2x, 4x and 6x respectively.

In some embodiments, an antibody molecule may comprise a VH domain comprising one or more or all of a FW1, a FW2, a FW3 and a FW4 having the sequences of SEQ ID NOs 1x, 3x, 5x and 7x respectively. Any of these FW regions may include 1 or more, for example 2 or 3 or more amino acid substitutions, deletions or insertions.

For example, an antibody molecule may comprise a VH domain having the sequence of SEQ ID NO: 15x or the sequence of SEQ ID NO: 15x with 1 or more, for example 2, 3, 4, 5, 6, 7, 8, 9, 10 or more amino acid substitutions, deletions or insertions in SEQ ID NO: 15x.

The anti-*Candida* recombinant human antibody molecule will typically further comprise a VL domain, for example a VL domain comprising LCDR1, LCDR2 and LCDR3 having the sequences of SEQ ID NOs 9x, 11x and 13x respectively, or the sequences of SEQ ID NOs 9x, 11x and 13x respectively with, independently, 1 or more, for example 2 or 3 or more amino acid substitutions, deletions or insertions. Examples of variant LCDR3 sequences are shown in SEQ ID NOs: 19x and 20x.

In some embodiments, an antibody molecule may comprise a VL domain comprising one or more or all of a FW1, a FW2, a FW3 and a FW4 having the sequences of SEQ ID NOs 8x, 10x, 12x and 14x respectively. Any of these may include 1 or more, for example 2 or 3 or more amino acid substitutions, deletions or insertions.

For example, an antibody molecule may comprise a VL domain having the sequence of SEQ ID NO: 16x or the sequence of SEQ ID NO: 16x with 1 or more, for example 2, 3, 4, 5, 6, 7, 8, 9, 10 or more amino acid substitutions, deletions or insertions in SEQ ID NO: 16x.

The anti-*Candida* recombinant human antibody molecule may for example comprise one or more amino acid substitutions, deletions or insertions which improve one or more properties of the antibody, for example affinity, functional half-life, on and off rates.

The techniques required in order to introduce substitutions, deletions or insertions within amino acid sequences of CDRs, antibody VH or VL domains and antibodies are generally available in the art. Variant sequences may be made, with substitutions, deletions or insertions that may or may not be predicted to have a minimal or beneficial effect on activity, and tested for ability to bind to *C. albicans* antigens and/or for any other desired property.

In some embodiments, an anti-*Candida* recombinant human antibody molecule may comprise a VH domain comprising a HCDR1, a HCDR2 and a HCDR3 having the sequences of SEQ ID NOs 2x, 4x, and 6x (or 17x or 18x), respectively, and a VL domain comprising a LCDR1, a LCDR2 and a LCDR3 having the sequences of SEQ ID NOs 9x, 11x and 13x (or 19x or 20x), respectively.

For example, the VH and VL domains may have the amino acid sequences of SEQ ID NO: 15x and SEQ ID NO: 16x respectively; or may have the amino acid sequences of SEQ ID NO: 15x and SEQ ID NO: 16x comprising, independently 1 or more, for example 2, 3, 4, 5, 6, 7, 8, 9, 10 or more amino acid substitutions, deletions or insertions.

In some embodiments, an anti-*Candida* recombinant human antibody molecule VH domain may have at least about 60% sequence identity to SEQ ID NO: 15x, e.g. at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 15x.

In some embodiments, an anti-*Candida* recombinant human antibody molecule VL domain may have at least about 60% sequence identity to SEQ ID NO: 16x, e.g. at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity to SEQ ID NO: 16x.

The anti-*Candida* recombinant human antibody molecule may be in any format, as described above, In some preferred embodiments, the anti-*Candida* recombinant human antibody molecule may be a whole antibody, for example an IgG, such as IgG1, IgA, IgE or IgM. In some preferred embodiments, than anti-*Candida* recombinant human antibody molecule is a scAb or scFv.

An anti-*Candida* recombinant human antibody molecule of the invention may be one which competes for binding to the target (e.g. Hyr1) with an antibody molecule described herein, for example an antibody molecule which
(i) binds Hyr1 and
(ii) comprises a VH domain of SEQ ID NO: 15x and/or VL domain of SEQ ID NO: 16x; an HCDR3 of SEQ ID NO: 6x; an HCDR1, HCDR2, LCDR1, LCDR2, or LCDR3 of SEQ ID NOS: 2x, 4x, 9x, 11x or 13x respectively; a VH domain comprising HCDR1, HCDR2 and HCDR3 sequences of SEQ ID NOS: 2x, 4x and 6x respectively; and/or a VH domain comprising HCDR1, HCDR2 and HCDR3 sequences of SEQ ID NOS: 2x, 4x and 6x and a VL domain comprising LCDR1, LDR2 and LCDR3 sequences of SEQ ID NOS: 9x, 11x and 13x respectively,
where x here is C, D, E, F or G.

An anti-*Candida* recombinant human antibody molecule of the invention may be one which competes for binding to the target (e.g. *C. albicans* whole cell wall extract) with an antibody molecule described herein, for example an anti-body molecule which
(i) binds *C. albicans* whole cell wall extract, and
(ii) comprises a VH domain of SEQ ID NO: 15x and/or VL domain of SEQ ID NO: 16x; an HCDR3 of SEQ ID NO: 6x; an HCDR1, HCDR2, LCDR1, LCDR2, or LCDR3 of SEQ ID NOS: 2x, 4x, 9x, 11x or 13x respectively; a VH domain comprising HCDR1, HCDR2 and HCDR3 sequences of SEQ ID NOS: 2x, 4x and 6x respectively; and/or a VH domain comprising HCDR1, HCDR2 and HCDR3 sequences of SEQ ID NOS: 2x, 4x and 6x and a VL domain comprising LCDR1, LDR2 and LCDR3 sequences of SEQ ID NOS: 9x, 11x and 13x respectively,
where x here is A-B, or H—R.

Competition between antibody molecules may be assayed easily in vitro, for example using ELISA and/or by tagging a specific reporter molecule to one antibody molecule which can be detected in the presence of one or more other untagged antibody molecules, to enable identification of antibody molecules which bind the same epitope or an overlapping epitope. Such methods are readily known to one of ordinary skill in the art.

Thus, a further aspect of the present invention provides a binding member or antibody molecule comprising an antigen-binding site that competes with an antibody molecule, for example an antibody molecule comprising a VH and/or VL domain, CDR e.g. HCDR3 or set of CDRs of the parent antibody described above for binding to target antigen. A suitable antibody molecule may comprise an antibody antigen-binding site which competes with an antibody antigen-binding site for binding to target antigen wherein the antibody antigen-binding site is composed of a VH domain and a VL domain, and wherein the VH and VL domains comprise HCDR1, HCDR2 and HCDR3 sequences of SEQ ID NOS: 2x, 4x, and 6x (or 17x or 18x) and LCDR1, LDR2 and LCDR3 sequences of SEQ ID NOS: 9x, 11x, and 13x (or 19x or 20x) respectively, for example the VH and VL domains of SEQ ID NOS: 15x and 16x.

The VH and VL framework encoded by the genes encoded from the B cell antibody factories can be readily modified by molecular genetics to alter and refine the properties of the antibodies. Such modified sequences are termed "derived" from the B cells herein.

For example is may be desired to remove Cys residues in the sequence, to minimise potential incorrect Cys pairings.

Thus the invention also provides a method for producing an antibody antigen-binding domain for a fungal target as described herein, preferably *C. albicans* Hyr1 protein or whole cell wall extract, which comprises:
  providing, by way of addition, deletion, substitution or insertion of one or more amino acids in the amino acid sequence of a parent VH domain comprising HCDR1, HCDR2 and HCDR3, wherein the parent VH domain HCDR1, HCDR2 and HCDR3 have the amino acid sequences of SEQ ID NOS: 2x, 4x and 6x respectively, a VH domain which is an amino acid sequence variant of the parent VH domain, and;
  optionally combining the VH domain thus provided with one or more VL domains to provide one or more VH/VL combinations; and
  testing said VH domain which is an amino acid sequence variant of the parent VH domain or the VH/VL combination or combinations to identify an antibody antigen binding domain for target antigen.

A VH domain which is an amino acid sequence variant of the parent VH domain may have the HCDR3 sequence of SEQ ID NO: 6x or a variant with the addition, deletion, substitution or insertion of one, two, three or more amino acids e.g. 17x or 18x.

The VH domain which is an amino acid sequence variant of the parent VH domain may have the HCDR1 and HCDR2 sequences of SEQ ID NOS: 2x and 4x respectively, or variants of these sequences with the addition, deletion, substitution or insertion of one, two, three or more amino acids.

The invention also provides a method for producing an antibody antigen-binding domain for a fungal target as described herein, preferably *C. albicans* Hyr1 protein or whole cell wall extract, which comprises:
  providing starting nucleic acid encoding a VH domain or a starting repertoire of nucleic acids each encoding a VH domain, wherein the VH domain or VH domains either comprise a HCDR1, HCDR2 and/or HCDR3 to be replaced or lack a HCDR1, HCDR2 and/or HCDR3 encoding region;
  combining said starting nucleic acid or starting repertoire with donor nucleic acid or donor nucleic acids encoding or produced by mutation of the amino acid sequence of an HCDR1, HCDR2, and/or HCDR3 having the amino acid sequences of SEQ ID NOS: 2x, 4x and 6x respectively, such that said donor nucleic acid is or donor nucleic acids are inserted into the CDR1, CDR2 and/or CDR3 region in the starting nucleic acid or starting repertoire, so as to provide a product repertoire of nucleic acids encoding VH domains;
  expressing the nucleic acids of said product repertoire to produce product VH domains;
  optionally combining said product VH domains with one or more VL domains; selecting an antibody molecule that binds the fungal target, which antibody molecule comprises a product VH domain and optionally a VL domain; and recovering said antibody molecule or nucleic acid encoding it.

Suitable techniques for the maturation and optimisation of antibody molecules are well-known in the art.

Anti-*Candida* recombinant human antibody molecules may be further modified by chemical modification, for example by PEGylation, or by incorporation in a liposome, to improve their pharmaceutical properties, for example by increasing in vivo half-life.

An anti-*Candida* recombinant human antibody molecule as described herein may conjugated to a toxic payload (e.g. ricin) that could kill the fungus and act as a therapeutic antibody.

An anti-*Candida* recombinant human antibody molecule as described herein may be one which binds Hyr1 with an $EC_{50}$ values of 1 to 1500, e.g. 10 to 500, or 20 to 200 ng/ml.

An anti-*Candida* recombinant human antibody molecule as described herein may be one which binds *C. albicans* with an $EC_{50}$ values of 1 to 1500, e.g. 1 to 500, or 1 to 40 ng/ml.

EC50 can be assessed as described hereinafter with ELISA e.g. as described in the Examples below for "Circulating IgG Enzyme-linked Immunosorbent assay (ELISA) to identify donors with B cells to take forward" and "B cell supernatant screen against target antigens via ELISA".

Provided herein is a method of binding a fungal cell, for example *C. albicans*, the method comprising contacting the fungal cell with an anti-*Candida* recombinant human antibody molecule as described herein.

It is known that there are a large number of *Candida* species. Key *Candida* species which may be targeted by the antibodies described herein include *Candida albicans, Candida glabrata, Candida tropicalis, Candida parapsilosis* (a clonal complex of three species—*C. parapsilosis, C. orthopsilosis* and *C. metapsilosis*), and *Candida krusei* (synonym: *Issatchenkia orientalis*). Less-prominent species include *Candida guilliermondii, Candida lusitaniae, Candida kefyr, Candida famata* (synonym: *Debaryomyces hansenii*), *Candida inconspicua, Candida rugosa, Candida dubliniensis, Candida norvegensis, Candida auris, Candida haemulonii*.

As described herein, the anti-*Candida* recombinant human antibody molecules of the invention can detect both morphology specific and morphology-independent epitopes with high specificity. The antibody molecules described herein may thus bind to *C. albicans* with high affinity relative to other fungal targets. For example, an antibody molecule of the invention may display a binding affinity for *C. albicans* which is at least 1000 fold or at least 2000 fold greater than a non-*Candida* pathogenic fungus such as *Aspergillus fumigatus* and *Cryptococcus neoformans* and *Pneumocystis jirovecii*.

Nevertheless an anti-*Candida* recombinant human antibody molecule as described herein may bind to the species closely related to *C. albicans* e.g. *C. dubliniensis, C. tropicalis, C. parapsilosis* (clonal complex), *C. krusei, C. auris* (clonal complex), *C. glabrata* and *C. lusitaniae* e.g. for example with an affinity within a 1000-fold o of the binding to *C. albicans* (assessed using EC50).

Provided herein is a method of opsonising, or increasing the rate of opsonisation of a fungal cell, for example *C. albicans*, the method comprising contacting or pre-incubating the fungal cell with an anti-*Candida* recombinant human antibody molecule as described herein.

Provided herein is a method of increasing the rate of engulfment of a fungal cell, for example *C. albicans*, by macrophages, the method comprising contacting the fungal cell with an anti-*Candida* recombinant human antibody molecule as described herein. The antibody molecule may optionally be one specific for the hyphal-specific protein Hyr1.

Provided herein is a method of increasing the rate of macrophage attraction to a fungal cell, for example *C. albicans*, the method comprising contacting or pre-incubating the fungal cell with an anti-*Candida* recombinant human antibody molecule as described herein. The antibody molecule may optionally be one raised to whole cell wall preparation of the fungal cell.

Treatment of Disease

An anti-*Candida* recombinant human antibody molecule as described herein may be used for clinical benefit in the treatment of a fungus-associated condition, and particularly infections caused by *Candida* species, i.e. candidiasis. Preferred antibody molecules are those specific for *C. albicans* cell wall preparations.

*C. albicans* is the most common serious fungal pathogen of humans, and the embodiments disclosed herein may be used in the prophylaxis or treatment of any condition related to infection caused by *C. albicans*.

The fungus is part of the normal gut flora of around 50% of the population and is normally harmless but can cause superficial mucosal infections such as oral and vaginal thrush and life-threatening systemic disseminated disease in immunocompromised individuals. Immunocompromised individuals may have a weakened immune system due to medical treatment (e.g. cancer treatment or organ transplant recipients), or due to a disease or disorder (e.g. HIV/AIDS, SCID, CVID). Other conditions that may be treated include lung infections in cystic fibrosis patients, mixed microbial infections, which include both bacteria (e.g. *Pseudomonas* spp.) and fungi, fungal infections on indwelling medical devices such as catheters, and skin and urinary tract infections.

The antibody molecules as described herein may be useful in the surgical and other medical procedures which may lead to immunosuppression, or medical procedures in patients who are already immunosuppressed.

Patients suitable for treatment as described herein include patients with conditions in which fungal infection is a symptom or a side-effect of treatment or which confer an increased risk of fungal infection or patients who are predisposed to or at increased risk of fungal infection, relative to the general population. For example, an anti-*Candida* recombinant human antibody molecule as described herein may also be useful in the treatment or prevention of fungal infection in cancer patients.

An anti-*Candida* recombinant human antibody molecule as described herein may be used in a method of treatment of the human or animal body, including prophylactic or preventative treatment (e.g. treatment before the onset of a condition in an individual to reduce the risk of the condition occurring in the individual; delay its onset; or reduce its severity after onset). The method of treatment may comprise administering an anti-*Candida* recombinant human antibody molecule to an individual in need thereof.

Aspects of the invention provide; an anti-*Candida* recombinant human antibody molecule as described herein for use in a method of treatment of the human or animal body; an anti-*Candida* recombinant human antibody molecule as described herein for use in a method of treatment of a fungal infection; the use of an anti-*Candida* recombinant human antibody molecule as described herein in the manufacture of a medicament for the treatment of a fungal infection; and a method of treatment of a fungal infection comprising administering an anti-*Candida* recombinant human antibody molecule as described herein to an individual in need thereof.

Pharmaceutical Compositions and Dosage Regimens

Anti-*Candida* recombinant human antibody molecules may be comprised in pharmaceutical compositions with a pharmaceutically acceptable excipient.

A pharmaceutically acceptable excipient may be a compound or a combination of compounds entering into a pharmaceutical composition which does not provoke secondary reactions and which allows, for example, facilitation of the administration of the anti-*Candida* recombinant human antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-*Candida* recombinant human antibody molecule.

In some embodiments, anti-*Candida* recombinant human antibody molecules may be provided in a lyophilised form for reconstitution prior to administration. For example, lyophilised antibody molecules may be re-constituted in sterile water and mixed with saline prior to administration to an individual.

Anti-*Candida* recombinant human antibody molecules will usually be administered in the form of a pharmaceutical composition, which may comprise at least one component in addition to the antibody molecule. Thus pharmaceutical compositions may comprise, in addition to the anti-*Candida* recombinant human antibody molecule, a pharmaceutically acceptable excipient, carrier, buffer, stabiliser or other materials well known to those skilled in the art. Such materials should be non-toxic and should not interfere with the efficacy of the anti-*Candida* recombinant human antibody molecule. The precise nature of the carrier or other material will depend on the route of administration, which may be by bolus, infusion, injection or any other suitable route, as discussed below.

For parenteral, for example sub-cutaneous or intra-venous administration, e.g. by injection, the pharmaceutical composition comprising the anti-*Candida* recombinant human antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilisers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™ PLURONICS™ or polyethylene glycol (PEG).

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody molecules are well known in the art (Ledermann, J. A., Begent, R. H., Massof, C., Kelly, A. M., Adam, T. and Bagshawe, K. D. (1991). A phase-I study of repeated therapy with radiolabelled antibody to carcinoembryonic antigen using intermittent or continuous administration of cyclosporin A to suppress the immune response. *Int. J. Cancer* 47:659-664). Specific dosages may be indicated herein or in the Physician's Desk Reference (2003) as appropriate for the type of medicament being administered may be used. A therapeutically effective amount or suitable dose of an antibody molecule may be determined by comparing it's in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications. An initial higher loading dose, followed by one or more lower doses, may be administered.

Typically, the antibody will be a whole antibody, e.g. the IgG1 isotype, and where a whole antibody is used, dosages at the lower end of the ranges described herein may be preferred. This is a dose for a single treatment of an adult patient, which may be proportionally adjusted for children and infants, and also adjusted for other antibody formats in proportion to molecular weight.

Preferably the antibody or fragment will be dosed at no more than 50 mg/kg or no more than 100 mg/kg in a human patient, for example between 1 and 50, e.g. 5 to 40, 10 to 30, 10 to 20 mg/kg.

Treatments may be repeated at daily, twice-weekly, weekly or monthly intervals, at the discretion of the physician. The treatment schedule for an individual may be dependent on the pharmocokinetic and pharmacodynamic properties of the antibody composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Treatment may be given before, and/or after surgery, and/or may be administered or applied directly at the anatomical site of surgical treatment or invasive procedure. Suitable formulations and routes of administration are described above.

In some embodiments, anti-*Candida* recombinant human antibody molecules as described herein may be administered as sub-cutaneous injections. Sub-cutaneous injections may be administered using an auto-injector, for example for long term prophylaxis/treatment.

In some preferred embodiments, the therapeutic effect of the anti-*Candida* recombinant human antibody molecule may persist for several half-lives, depending on the dose. For example, the therapeutic effect of a single dose of anti-*Candida* recombinant human antibody molecule may persist in an individual for 1 month or more, 2 months or more, 3 months or more, 4 months or more, 5 months or more, or 6 months or more.

Combination Immunotherapy

It will be understood that the term "treatment" as used herein includes combination treatments and therapies, in which two or more treatments, therapies, or agents are combined, for example, sequentially or simultaneously.

The agents (i.e. the anti-*Candida* recombinant human antibody molecules described herein, plus one or more other agents) may be administered simultaneously or sequentially, and may be administered in individually varying dose schedules and via different routes. For example, when administered sequentially, the agents can be administered at closely spaced intervals (e.g., over a period of 5-10 minutes) or at longer intervals (e.g. 1, 2, 3, 4 or more hours apart, or even longer periods apart where required), the precise dosage regimen being commensurate with the properties of the therapeutic agent(s) as described herein, including their synergistic effect.

The agents (i.e. the anti-*Candida* recombinant human antibody molecules described here, plus one or more other agents) may be formulated together in a single dosage form, or alternatively, the individual agents may be formulated separately and presented together in the form of a kit, optionally with instructions for their use.

For example, the compounds described herein may in any aspect and embodiment also be used in combination therapies, e.g. in conjunction with other agents e.g. antifungal agents. The second antifungal agent may be selected from an azole (e.g. fluconazole), a polyene (e.g. amphotericin B), a echinocandin (e.g. caspofungin), an allylamine (e.g. terbinafine), and a flucytosine (also called 5-fluorocytosine). The skilled person will recognise that other antifungal agents may also be used. In some embodiments, the second anti-fungal agent is a second anti-fungal antibody or an antimicrobial peptide. In some embodiments, the anti-*Candida* recombinant human antibody molecule described herein is conjugated to the second antifungal agent.

Preparation of Other Therapeutic Moieties

The anti-*Candida* recombinant human antibody molecules described herein may be utilised to isolate and identify protective antigens for development as fungal vaccines, or prepare or identify other therapeutic moieties.

For example the antigens bound by the anti-whole cell mAbs described herein may be identified by methods known to those skilled in the art. For example they could be screened against protein and carbohydrate mutants to identify those mutants where binding is reduced. Alternatively antigens can be identified more directly by a proteomics-based approach, for example using 2D electrophoresis and immunoblotting, followed by analysis of spots by trypsinization and mass-spectroscopy (see e.g. Silva et al. Mol Biochem Parasitol. 2013 April; 188(2):109-15.). Such antigens will have utility as potential vaccines.

Anti-idiotype anytibodies can be prepared to the antibodies described herein using methods well known to those in the art (see Polonelli, L et al. "Monoclonal Yeast Killer Toxin-like Candidacidal Anti-Idiotypic Antibodies." Clinical and Diagnostic Laboratory Immunology 4.2 (1997): 142-146; also U.S. Pat. No. 5,233,024).

Detection and Diagnosis

Anti-*Candida* recombinant human antibody molecules as described herein may also be useful in in vitro testing, for example in the detection of fungus or a fungal infection, for example in a sample obtained from a patient.

Anti-*Candida* recombinant human antibody molecules as described herein may be useful for identifying *C. albicans*, and/or distinguishing *C. albicans* from other fungi.

The presence or absence of a fungus (e.g. *C. albicans*) may be detected by (i) contacting a sample suspected of containing the fungus with an antibody molecule described herein, and (ii) determining whether the antibody molecule binds to the sample, wherein binding of the antibody molecule to the sample indicates the presence of the fungus.

A fungal infection, e.g. *C. albicans* infection, in an individual may be diagnosed by (i) obtaining a sample from the individual;

(ii) contacting the sample with an antibody molecule as described herein, and (iii) determining whether the antibody molecule binds to the sample, wherein binding of the antibody molecule to the sample indicates the presence of the fungal infection.

Binding of antibodies to a sample may be determined using any of a variety of techniques known in the art, for example ELISA, immunocytochemistry, immunoprecipitation, affinity chromatography, and biochemical or cell-based assays. In some embodiments, the antibody is conjugated to a detectable label or a radioisotope.

Lateral Flow Devices

The invention also provides rapid and highly specific diagnostic tests for detecting fungal pathogens, for example multiple fungal pathogens, in a single test Preferred tests detect not only *C. albicans*, but also one or more other major fungal pathogens e.g. *Aspergillus fumigatus* and *Cryptococcus neoformans* and *Pneumocystis jirovecii*. Other fungal pathogens which it may be desirable to detect include zygomycete fungiand skin dermatophytic (ringworm) fungi. Antibody molecules specific for these other pathogens may be provided in the light of the disclosure herein, for example.

Preferably the test is in the form of a lateral flow device (LFD). Such LFDs are particularly suitable for use as point-of-care fungal diagnostics.

A lateral flow assay device for the analysis of body fluid will comprise at its most basic:

(i) a housing, and (ii) a flow path.

The devices, systems and methods described herein are for measuring analyte levels in body fluids of animals, particularly mammals including humans, or in environmental samples e.g. where it is believed fungal pathogens may exist.

As used anywhere herein, unless context demands otherwise, the term 'body fluid' may be taken to mean any fluid found in the body of which a sample can be taken for analysis. Examples of body fluids suitable for use in the present invention include, but are not limited to blood, urine, sweat and saliva. Preferably, the body fluid is blood. The fluid may be diluted by a pre-determined amount prior to assay, and any quantification indicator on the LFD may reflect that pre-determined dilution.

Some aspects of the LFD will now be discussed in more detail:

Flow Path of LFD

The flow path (e.g. a chromatographic strip) is preferably provided by a carrier, through which the test substance or body fluid can flow by capillary action. In one embodiment, the carrier is a porous carrier, for example a nitrocellulose or nylon membrane.

In a further embodiment, sections or all of the carrier may be non-porous. For example, the non-porous carrier may comprise areas of perpendicular projections (micropillars) around which lateral capillary flow is achieved, as described in for example WO2003/103835, WO2005/089082 and WO2006/137785, incorporated herein by reference.

The flow path will typically have an analyte-detection zone comprising a conjugate release zone and a detection zone where a visible signal reveals the presence (or absence) of the analyte of interest. The test substance can be introduced into the LFD and flows through to the detection zone.

Preferably the carrier material is in the form of a strip, sheet or similar to the material described in WO2006/137785 to which the reagents are applied in spatially distinct zones. The body fluid sample is allowed to permeate through the sheet, strip or other material from one side or end to another.

Analyte Detection Methods

Analyte detection may be based on competitive or sandwich (non-competitive) assays. Such assays may be used to detect analytes (antigens) from *C. albicans*, plus optionally one or more other major fungal pathogens e.g. from *Aspergillus fumigatus, Cryptococcus neoformans* and/or *Pneumocystsis jirovecii*. Other targets include zygomycete fungi and skin dermatophytic fungi.

The conjugate release zone may contain freely mobile antibodies to the analyte of interest. Alternatively, the conjugate release zone may comprise reagents for carrying out a particular assay to enable detection of the analyte, as described herein.

The binding partners may be attached to a mobile and visible label. A "label" is a composition detectable by spectroscopic, photochemical, biochemical, immunochemical, electrical, optical or chemical means. Useful labels in the present invention include magnetic beads (e.g., Dynabeads™), fluorescent dyes, radiolabels, enzymes, and colorimetric labels such as colloidal gold, silver, selenium, or other metals, or coloured glass or plastic (e.g., polystyrene, polypropylene, latex, etc.) beads. Preferred is a gold colloid or latex bead.

If the analyte is present in the sample, it will bind to the labelled binding partners. In preferred embodiments the intensity of the colour may be directly proportional to the amount of analyte. Here the detection zone comprises permanently immobilised unlabelled specific binding reagent for the same analyte. The relative positioning of the labelled binding partner and detection zone being such that a body fluid sample applied to the device can pick up labelled binding partner and thereafter permeate into the detection zone. The amount of bound label can be detected as a visible signal in the detection zone.

The label in the LFD will be quantifiable by conventional means or as described herein.

In one competitive format embodiment, the detection zone contains regions of immobile analyte-protein derivatives. These bind and immobilise any of the labelled binding partners not already bound by the analyte in the sample, producing a coloured line or stripe. In this case the amount of label bound in the detection zone (and hence the intensity of the coloured stripe) will be inversely proportional to the amount of analyte in the sample.

In another competitive format, a labelled analyte or analyte analogue may alternatively be provided and this is detected using immobilized specific binding partner (e. g. immobilized antibody specific for the analyte) in the detection zone.

In another competitive format, a labelled analyte or analyte analogue is provided along with a specific binding partner (e.g. an antibody specific for the analyte). The resulting mixture is conveyed to the detection zone presenting immobilised binding partner of the analyte or analyte analogue. The higher the amount of analyte in the sample, the higher the amount of free labelled analyte which leaves the conjugate release zone to be detected in the detection zone.

Control Zone

Preferably the LFD for use with the present invention contains a control zone, which may be located after the detection zone in the direction of sample flow, in which excess labelled binding partner binds to produce a visible signal showing that the test has been successfully run.

Alternatively or additionally, a control zone may be located before the detection zone in the direction of sample flow, indicating that enough sample has been collected to allow operation of the test.

In one embodiment, the control zone is used as a reference point for a reader (see below).

Multiplex Devices

In various aspects of the invention, the LFD may be capable of detecting two (or more) different analytes e.g. analytes (antigens) from *C. albicans*, plus optionally from one or more or all of *Aspergillus fumigatus, Cryptococcus neoformans* and/or *Pneumocystsis jirovecii*. Other targets include zygomycete fungi and skin dermatophytic fungi.

A number of multiplex formats are known in LFDs.

For example, the flow path may comprise two or more carriers. The carriers may be positioned along the flow path consecutively. In use, body fluid would flow along each carrier sequentially.

In a further embodiment, two or more carriers may be positioned in the flow path in parallel. In use, body fluid would flow along each carrier simultaneously.

In one embodiment, two analytes are analysed using two distinct flow path e.g. the housing of the LFD houses the two flow paths.

In one embodiment, the analyte-detecting means may comprise a first binding reagent that specifically binds the analyte and a second binding reagent that specifically binds the analyte, wherein the first binding reagent is labelled and is movable through a carrier under the influence of a liquid by capillary flow and the second binding reagent is immobilised at a detection site in the flow path. The analyte-detecting means comprises a labelled, mobile antibody, specific for the analyte and an immobilised unlabelled antibody, specific for the analyte.

In one embodiment, the analyte-detecting means for each analyte may be positioned together on the carrier, but the specific analyte-binding reagent for each different analyte may comprise a different label. The different labels will be capable of being distinguished as described herein or by conventional means.

Alternatively, the analyte-detecting means for each analyte may be spatially distinct. The flow path in the 'multiplexed' LFD may incorporate two or more discrete carriers of porous or non-porous solid phase material, e.g. each carrying mobile and immobilised reagents. These discrete bodies can be arranged in parallel, for example, such that a single application of body fluid sample to the device initiates sample flow in the discrete bodies simultaneously. The separate analytical results that can be determined in this way can be used as control results, or if different reagents are used on the different carriers, the simultaneous determination of a plurality of analytes in a single sample can be made. Alternatively, multiple samples can be applied individually to an array of carriers and analysed simultaneously.

Preferably, multiple analyte detection zones may be applied as lines spanning or substantially spanning the width of a test strip or sheet, preferably followed or preceded by one or more control zones in the direction of body fluid travel. However, multiple analyte detection zones may also, for example, be provided as spots, preferably as a series of discrete spots across the width of a test strip or sheet at the same height. In this case, a one or more control zones may again be provided after or before the analyte detection zones in the direction of body fluid travel.

Detection Systems

The presence or intensity of the signal in the detection zone may be determined by eye, optionally by comparison to a reference chart or card.

Where the intensity of the signal in the detection zone is to be converted to a quantitative reading of the concentration of analyte in the sample it will be preferred that the LFD can be used in conjunction with a screening device ('reader'). The reader is preferably a handheld electronic device into which the LFD cartridge can be inserted after the sample has been applied.

The reader comprises a light source such as an LED, light from which illuminates the LFD membrane. The reflected image of the membrane may be detected and digitised, then analysed by a CPU and converted to a result which can be displayed on an LCD screen or other display technology (or output via a conventional interface to further storage or analytical means). A light-dependent resistor, phototransistor, photodiode, CCD or other photo sensor may be used to measure the amount of reflected light. The result may be displayed as positive or negative for a particular analyte of interest or, preferably, the concentration of the particular analyte may be displayed. More specifically the conventional reader comprises: illuminating means for illuminating an immunoassay test; photosensitive detector means for detecting the intensity of light from the illuminating means which is reflected from the immunoassay test; means, coupled to the output of the photosensitive detector means, for representing the intensity of the detected light by a data array; memory means for storing preset data; first data processing means, coupled to the memory means and to the output of the means for representing the intensity of the detected light by a data array, for segmenting the data array according to the preset data into control data, background data and test data; second data processing means, coupled to the first data processing means, for determining whether the test data exhibits a statistically significant result; and output means, coupled to the output of the second data processing means, for outputting the results from the second data processing means.

In embodiments of the present invention where multiple analytes are assessed, the reader may analyse the results to detect a plurality of spatially distinct detection or test zones pertaining to different analytes. The photosensitive detector means (e.g. light dependent resistor, phototransistor, photodiode, CCD or other light sensor) will therefore detect reflected light from all of these (optionally scanning them) and generate a discrete or segmented data stream for each zone. Respective control zonal data and background zonal data may also be gathered for the different analytes.

The colour of the LED or other source may vary dependent on the label or method of detecting the analyte.

For gold-labelled analytes, a white LED may be preferable, and therefore a reader may comprise both a red and white LED.

Unless stated otherwise, or clear from the context, antibody residues, where numbered herein, are numbered in accordance with the Kabat numbering scheme.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

The disclosure of all references cited herein, inasmuch as it may be used by those skilled in the art to carry out the invention, is hereby specifically incorporated herein by cross-reference.

FIGURES

Figure 1:
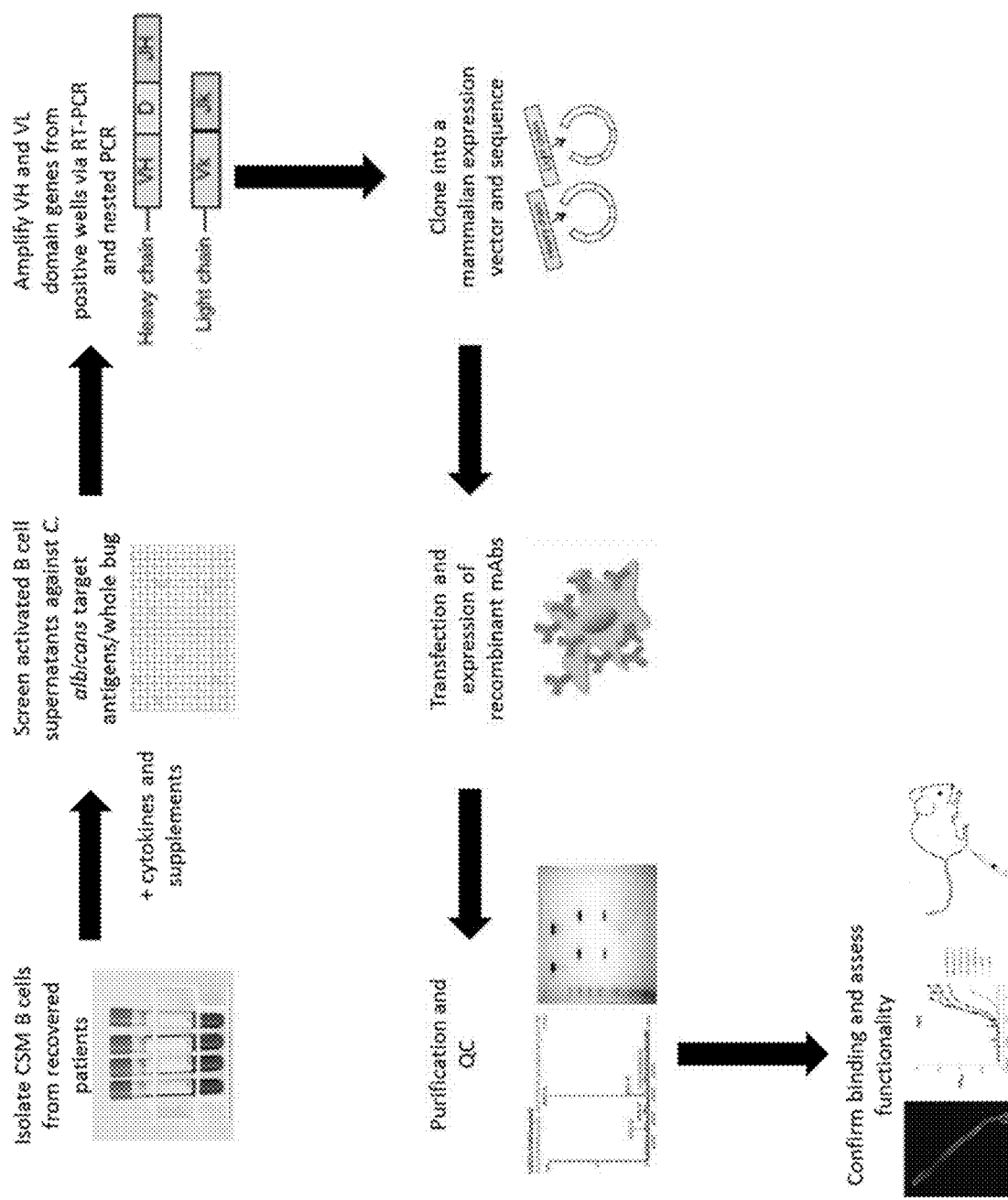

FIG. 1—Workflow for the generation of human monoclonal antibodies from single B cells. Class-switched memory B cells were isolated from individuals and microcultured in activating media to promote IgG secretion for screening against target antigens. VH and VL genes from B cells positive for the target were amplified and cloned into a mammalian expression vector for expression and purification via fast protein liquid chromatography. Following QC, recombinant mAbs were assessed for functional activity in vitro and in vivo. Adapted from Huang et al. 2013 (38).

FIG. 2—Representative images from the process employed to generate fully human anti-*Candida* mAbs. FIG. 2A shows the ELISA screening of purified donor circulating IgG against the target antigens *C. albicans* 'whole cell' yeast and hyphae, and purified Hyr1 protein, to select the donors to take forward for B cell isolation. FIGS. 2B and 2C are representative agarose gel images following RT-PCR and nested PCR of VH and Vk-Ck genes respectively. FIGS. 2D and 2E are analytical mass spectrometry and analytical SEC traces of one of the purified recombinant IgG1 mAbs. Further quality control was carried out by SDS-PAGE gel analysis under non-reducing and reducing conditions as shown in FIGS. 2F and 2G.

Figure 3:
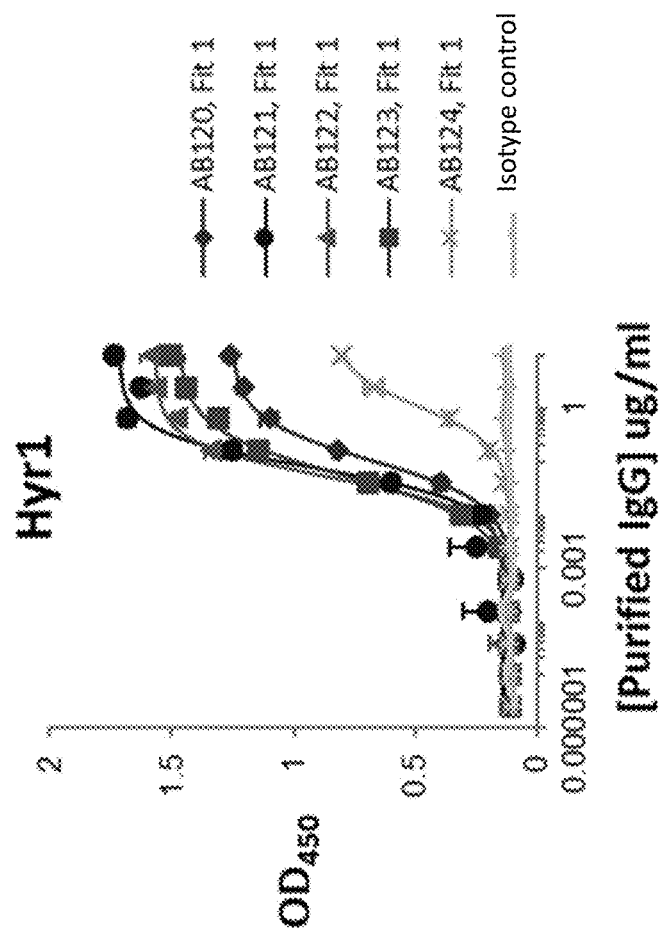
Figure 3:
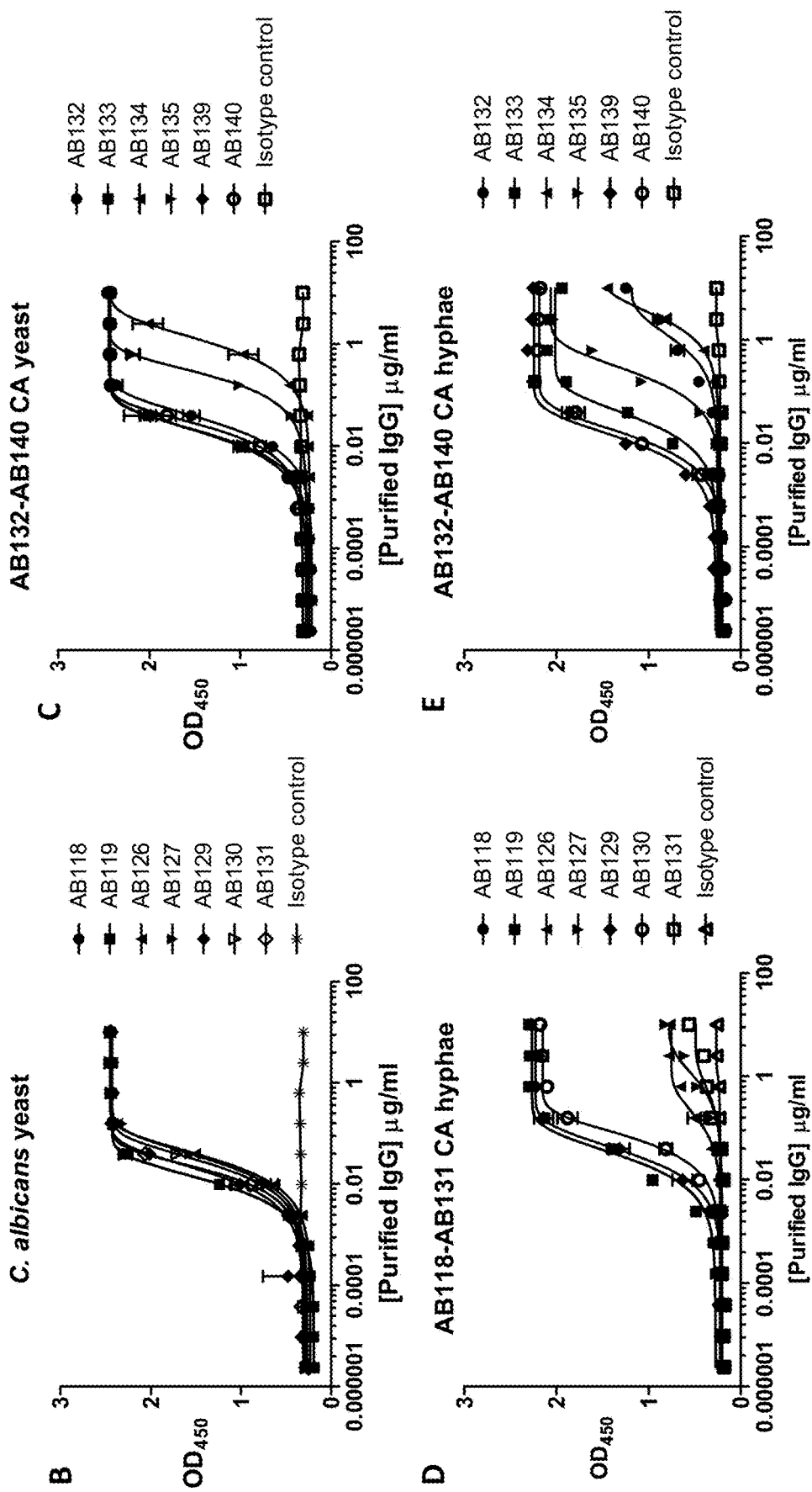

FIG. 3—Concentration response curves showing anti-*Candida* mAbs binding to target antigens. FIG. 3A shows purified anti-Hyr1 mAbs binding to purified recombinant Hyr1 protein in a concentration-dependent manner via ELISA. Binding of purified anti-'whole cell' *Candida* mAbs to *C. albicans* yeast (FIGS. 3B and 3C) and hyphal cells (FIGS. 3D and 3E) via ELISA are also shown. Values represent mean±SEM (n=2-4).

Figure 4:
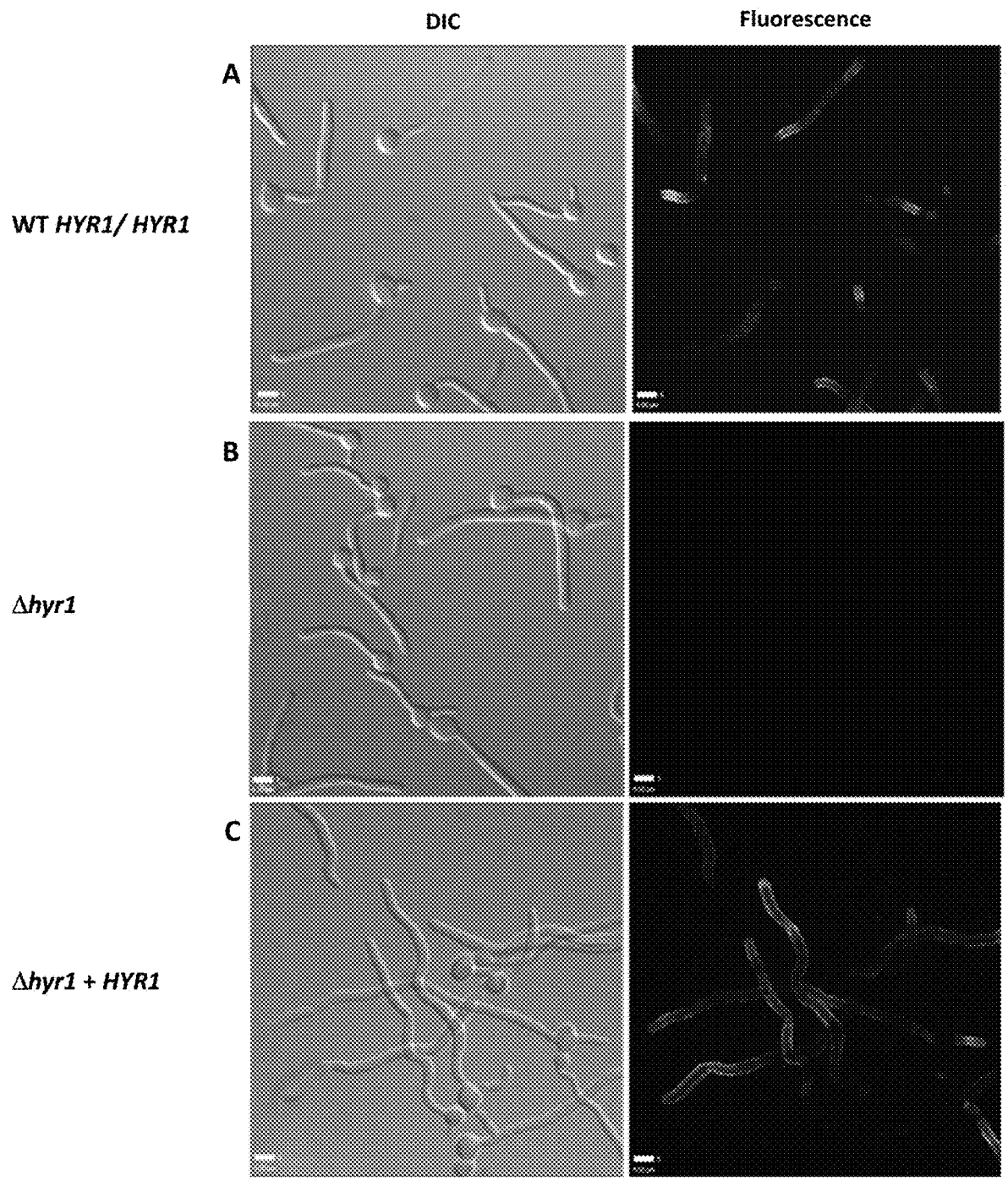

FIG. 4—Indirect immunofluorescence of AB120 binding to Hyr1 protein expressed on *C. albicans* hyphal cells. Indirect immunofluorescence with anti-Hyr1 mAb AB120 against WT CAl4-Clp10 (A), Hyr1 null mutant (B) and a Hyr1 re-integrant strain (C). A fluorescently conjugated secondary goat anti-human IgG antibody was used to detect anti-Hyr1 mAb binding. Scale bars represent 15 μm.

Figure 5:
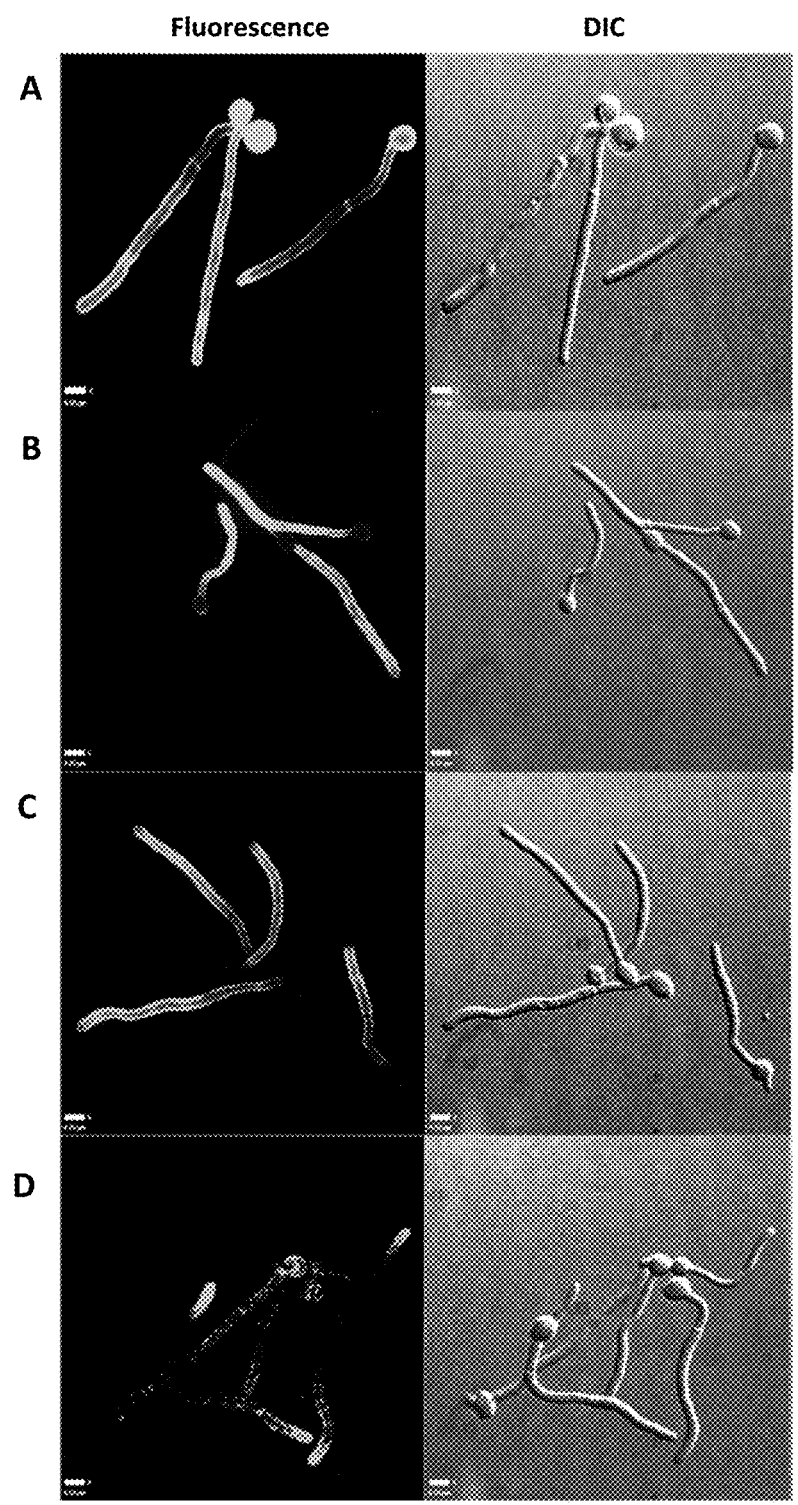

FIG. 5—Indirect immunofluorescence of anti-whole cell mAbs binding to WT CAl4-Clp10. Indirect immunofluorescence demonstrating the distinct binding patterns of the panel of anti-*Candida* mAbs. Shown are representative images of mAbs binding strongly to targets expressed on both CAl4-Clp10 yeast and hyphae (A), mAbs binding primarily to targets expressed on hyphae but with some binding to yeast (B), mAbs binding specifically to hyphae (C) and mAbs binding to yeast and the growing hyphal tip (D). A fluorescently conjugated secondary goat anti-human IgG antibody was used to detect anti-*Candida* mAb binding. Scale bars represent 19 μm.

FIG. 6—Heat-map of anti-*Candida* mAbs binding to *Candida* species and other pathogenic fungi. Immunofluorescence microscopy analysis of (a) anti-Hyr1 mAbs (AB120-AB123) and (b) cell wall mAbs (AB118-AB140) binding to *C. albicans* and other clinically relevant fungal species depicted in a heat map. Binding was graded from red (high) to yellow (none).

Figure 7:
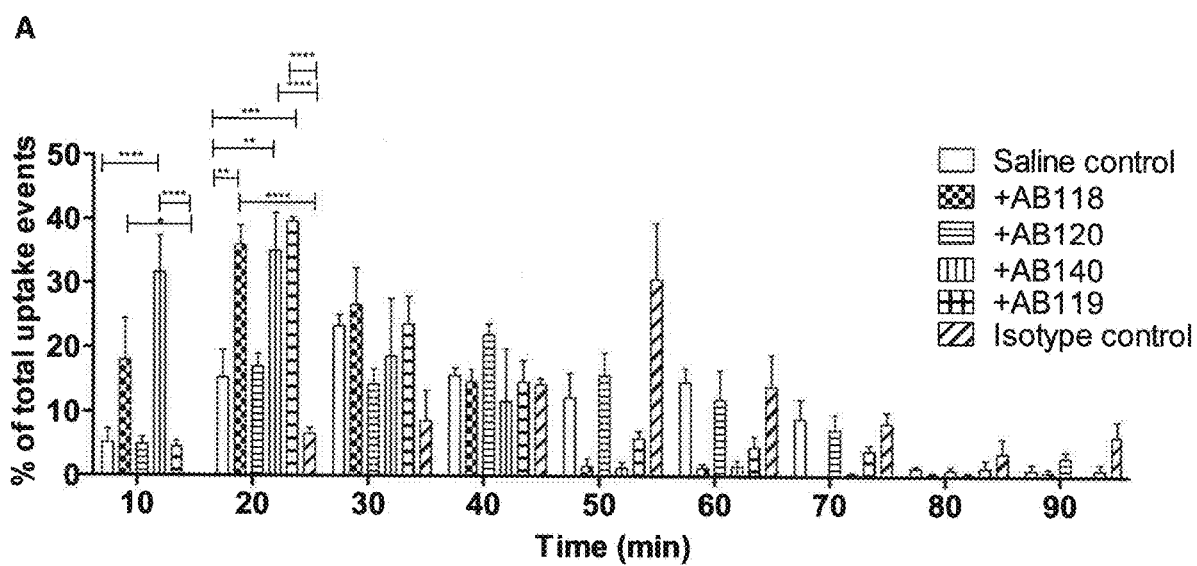
Figure 7:
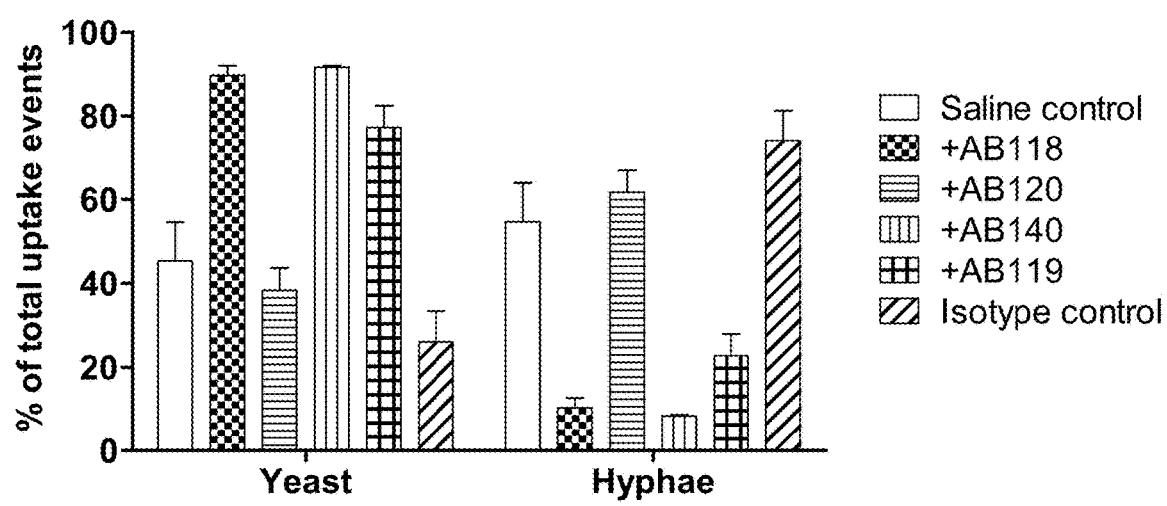

FIG. 7—Macrophage uptake of live *C. albicans* cells pre-incubated with saline, isotype control mAb or anti-*Candida* mAb. FIG. 7A shows the time at which an uptake event occurred over the first 90 min of the assay following *C. albicans* pre-incubation with saline, an IgG1 control antibody, an anti-whole cell mAb (AB118, AB119 and AB140) or an anti-Hyr1 mAb (AB120). FIG. 7B shows the morphology of *C. albicans* cells during each uptake event over the first 90 min of the assay following *C. albicans* pre-incubation with saline, an IgG1 control antibody, an anti-whole cell mAb (AB118, AB119 and AB140) or an anti-Hyr1 mAb (AB120). An uptake event was defined as the complete engulfment of a *C. albicans* cell by a macrophage. Bars represent percentage of uptake events ±SEM (n=3). *p<0.05, p<0.01, **p<0.0001.

Figure 8:
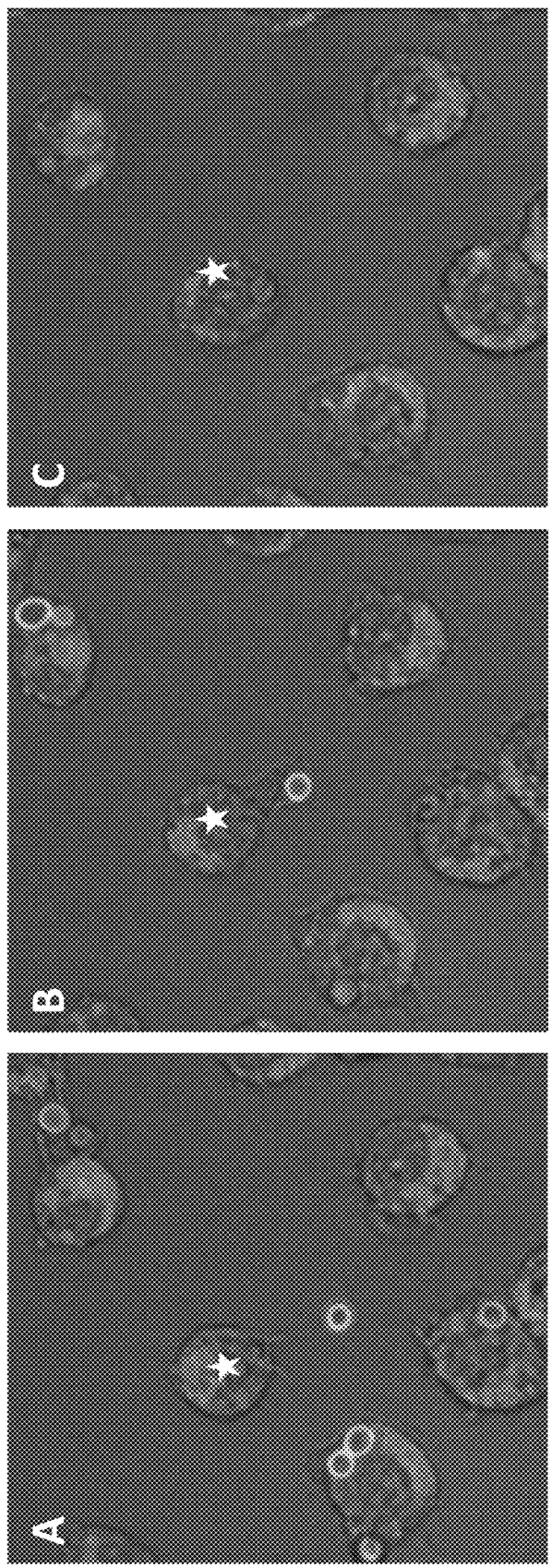
Figure 8:
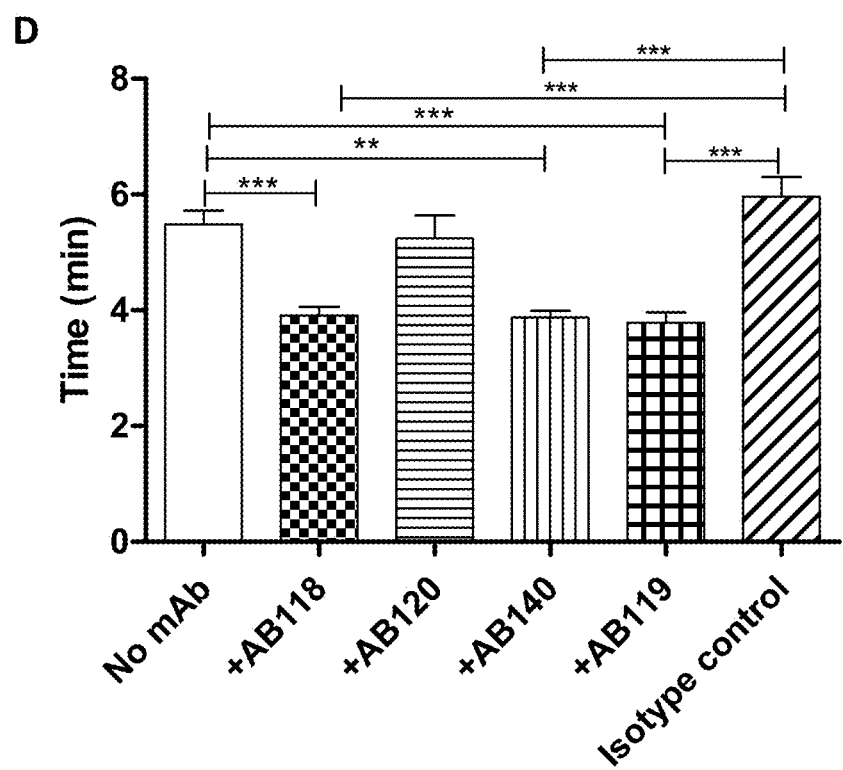
Figure 8:
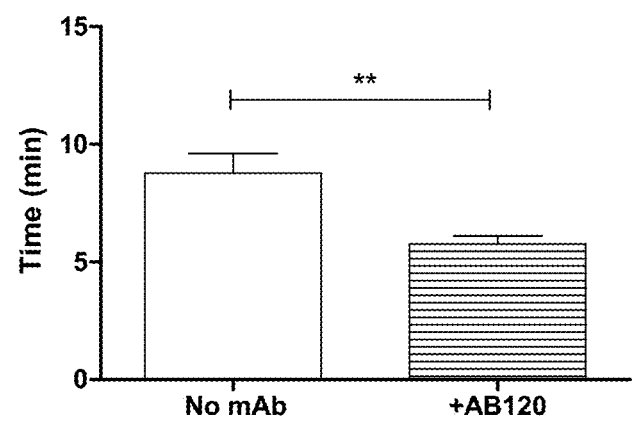

FIG. 8—Macrophage engulfment of live *C. albicans* cells pre-incubated with saline, isotype control mAb or anti-*Candida* mAb. FIGS. 8A-8C are snapshots taken from live cell video microscopy capturing the stages of *C. albicans* engulfment by J774.1 macrophages. FIG. 8A shows the macrophage (red, *) and *C. albicans* (green) prior to cell-cell contact, FIG. 8B shows the cells once cell-cell contact has been established and FIG. 8C shows the *C. albicans* within the phagocyte following ingestion. FIG. 8D shows the average time taken for a macrophage to engulf a live *C. albicans* cell following pre-incubation with saline, an IgG1 control antibody, an anti-whole cell mAb (AB118, AB119 and AB140) or an anti-Hyr1 mAb (AB120). FIG. 8E shows the time taken for a macrophage to ingest a filamentous *C. albicans* cell following pre-incubation of AB120 with hyphal *C. albicans*. Rate of engulfment was defined as the time taken from cell-cell contact to complete ingestion of the *C. albicans* cell inside the macrophage resulting in a loss of green fluorescence. Bars represent average time taken for a macrophage to ingest a *C. albicans* cell ±SEM (n=3) *p<0.01, ***p<0.005.

Figure 9:
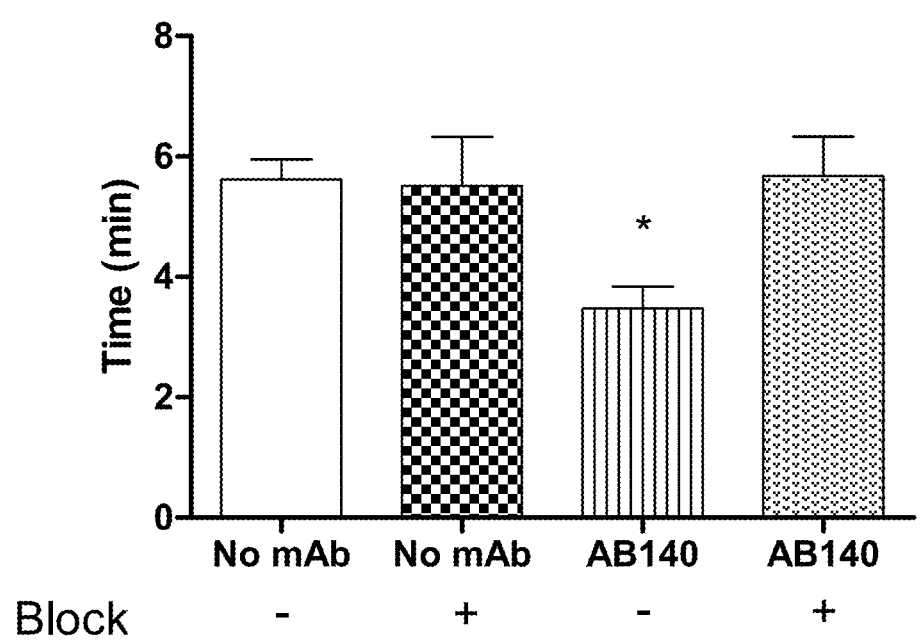

FIG. 9—Macrophage engulfment of opsonized live *C. albicans* cells in the presence and absence of an FcγR blocker. The average time taken for a macrophage to ingest a live *C. albicans* cell following pre-incubation with saline or an anti-whole cell mAb (AB140) in the presence or absence of an FcγR block. Bars represent average time taken for a macrophage to ingest a *C. albicans* cell ±SEM (n=3) *p<0.05.

FIG. 10—Macrophage migration towards *C. albicans* cells following pre-incubation with saline, an isotype control mAb or anti-*Candida* mAb. FIG. 10A shows mean velocity of macrophages as they migrate towards *C. albicans* cells following pre-incubation with saline, an IgG1 control mAb, or an anti-whole cell mAb (AB140). Bars represent macrophage mean track velocity ±SEM (n=3). FIG. 10B shows average distance travelled by a macrophage to engulf a *C. albicans* cell following pre-incubation with saline, an IgG1 control mAb, or an anti-whole cell mAb (AB140). Bars represent average distance travelled ±SEM (n=3). FIGS. 10C, 10D and 10E are tracking diagrams representing macrophage migration towards *C. albicans* cells pre-incubated with saline (blue), AB140 (pink) or IgG1 control mAb (green). Tracks represent the movement of individual macrophages relative to their starting position, up until the first uptake event. $*p<0.05$, $p<0.01$, $*p<0.005$.

FIG. 11—Assessment of anti-*Candida* mAbs in an in vivo model of disseminated candidiasis. *C. albicans* SC5314 was pre-incubated with saline, IgG1 control, anti-whole cell mAb (AB119) or anti-Hyr1 mAb (AB120) and then injected iv into the tail vein of BALB/c mice (n=6 per group). Kidney fungal burdens from each group were determined on day 3 post infection (FIG. 11A) and combined with the change in animal weight during the course of the infection to give an overall outcome score for disease progression (FIG. 11B). Dots represent individual animals; horizontal lines represent mean, $*p<0.05$, $**p<0.01$.

Figure 12:
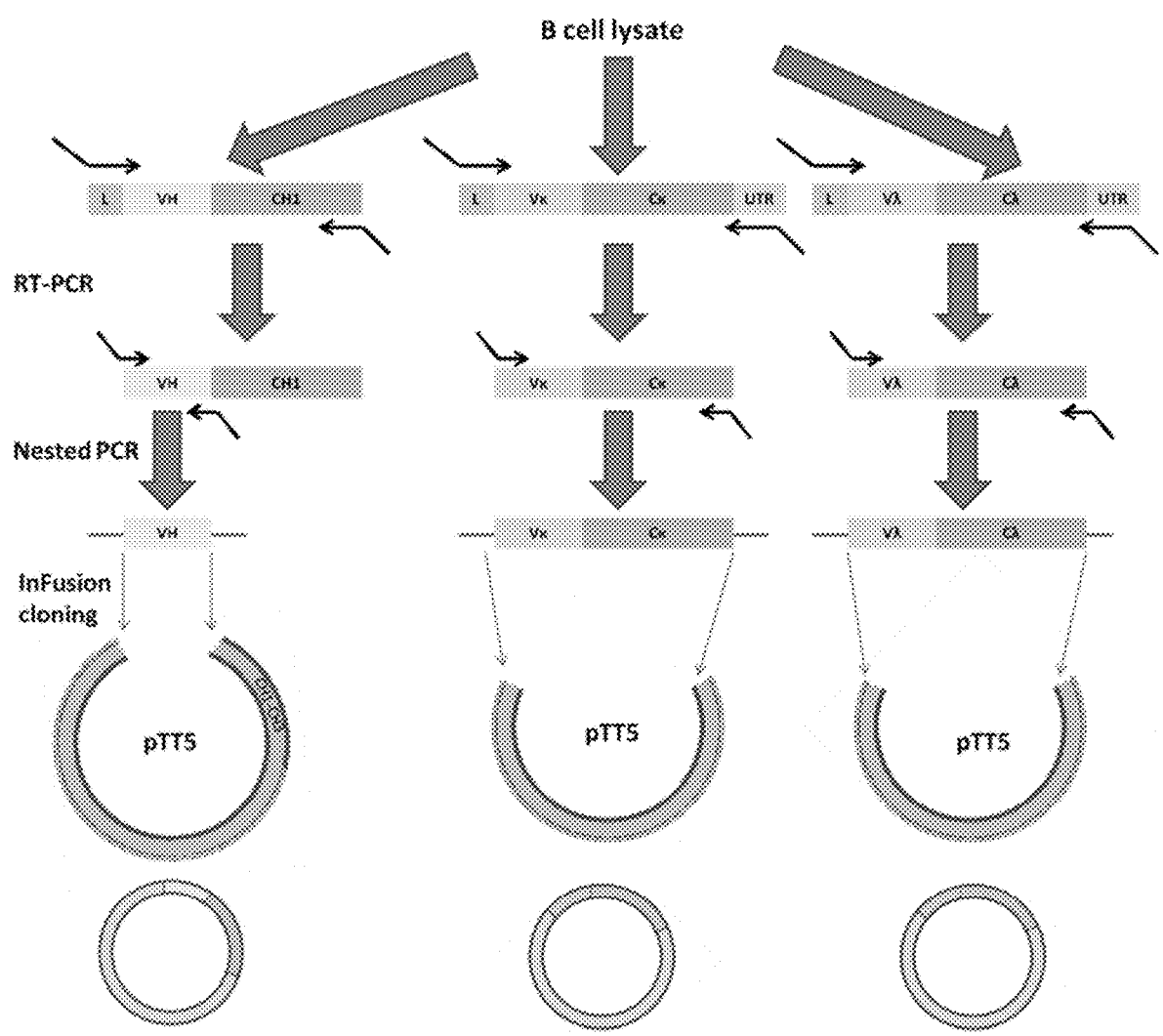

FIG. 12—Schematic of VH, Vκ-Cκ and Vλ-Cλ cloning into pTT5 expression vector. B cells positive for antigen binding in the initial ELISA screen were lysed. mRNA in B cell lysate was used as a template for VH, Vκ-Cκ and Vλ-Cλ gene amplification via RT-PCR. RT-PCR was carried out using forward primers specific to human V domain leader sequences and reverse primers specific for human IgCH1, Cκ or Cλ regions or light chain UTR. To increase the specificity of gene amplification, nested PCR was carried out using RT-PCR products as the template. Forward primers specific for human VH FW1 sequences and reverse primers specific for human VH FW4 sequences were used to amplify VH genes. To capture Vκ-Cκ and Vλ-Cλ genes, forward primers specific to human Vκ and human Vλ FW1 sequences were used in combination with reverse primers specific to the 3' end of the human Cκ or human Cλ regions. Primers used in nested PCR reactions contained 15 bp extensions which were complementary to the pTT5 expression vector to facilitate downstream Infusion cloning. Amplification of VH, Vκ-Cκ and Vλ-Cλ genes were done in separate reactions. RT-PCR—reverse transcriptase polymerase chain reaction; UTR untranslated region; L—leader sequence; $V_H$—heavy chain variable domain; Vκ—kappa chain variable domain; Vλ—lambda chain variable domain; $C_H$—heavy chain constant domain; Cκ—kappa chain constant domain; Cλ—lambda chain constant domain.

Figure 13:
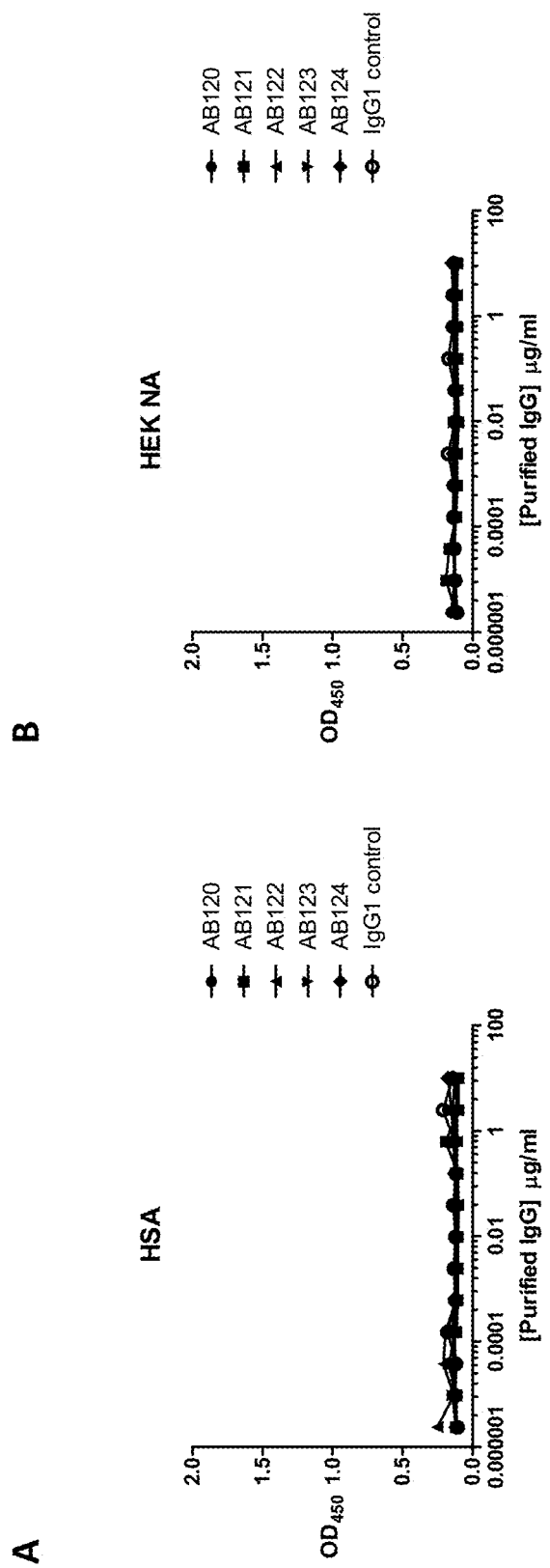

FIG. 13—Concentration response curves of purified anti-Hyr1 mAbs screened for binding to unrelated proteins. (a, b) Purified anti-Hyr1 mAbs screened against HSA and HEK NA respectively via ELISA. Values represent mean (n=2-4).

Figure 14:
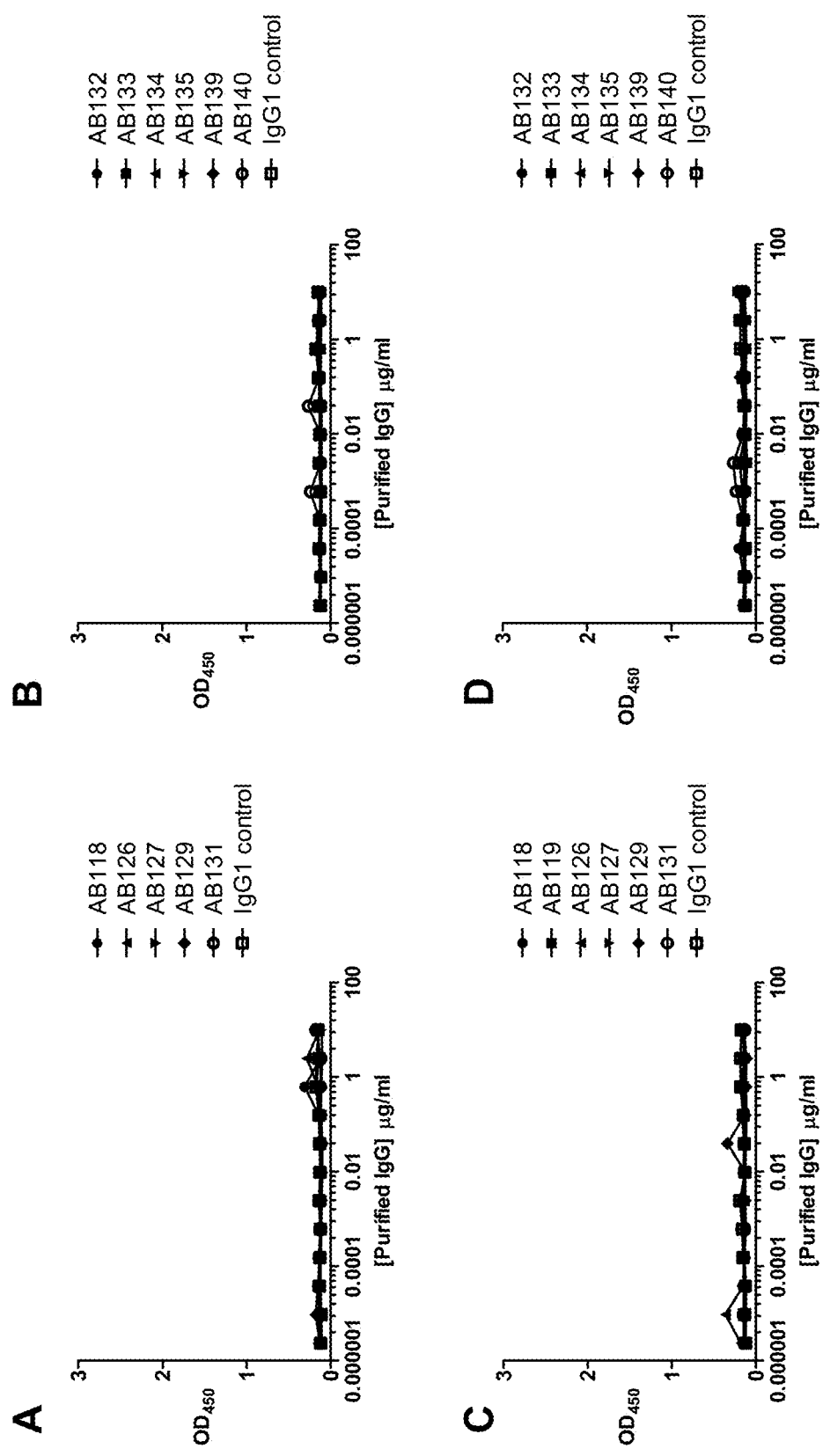

FIG. 14—Concentration response curves showing anti-whole cell mAbs screened for binding to unrelated proteins. (a, b) Purified cell wall mAbs screened against HSA. (c, d) the same mAbs screened against HEK NA via ELISA. Values represent mean (n=2-4).

Figure 15:
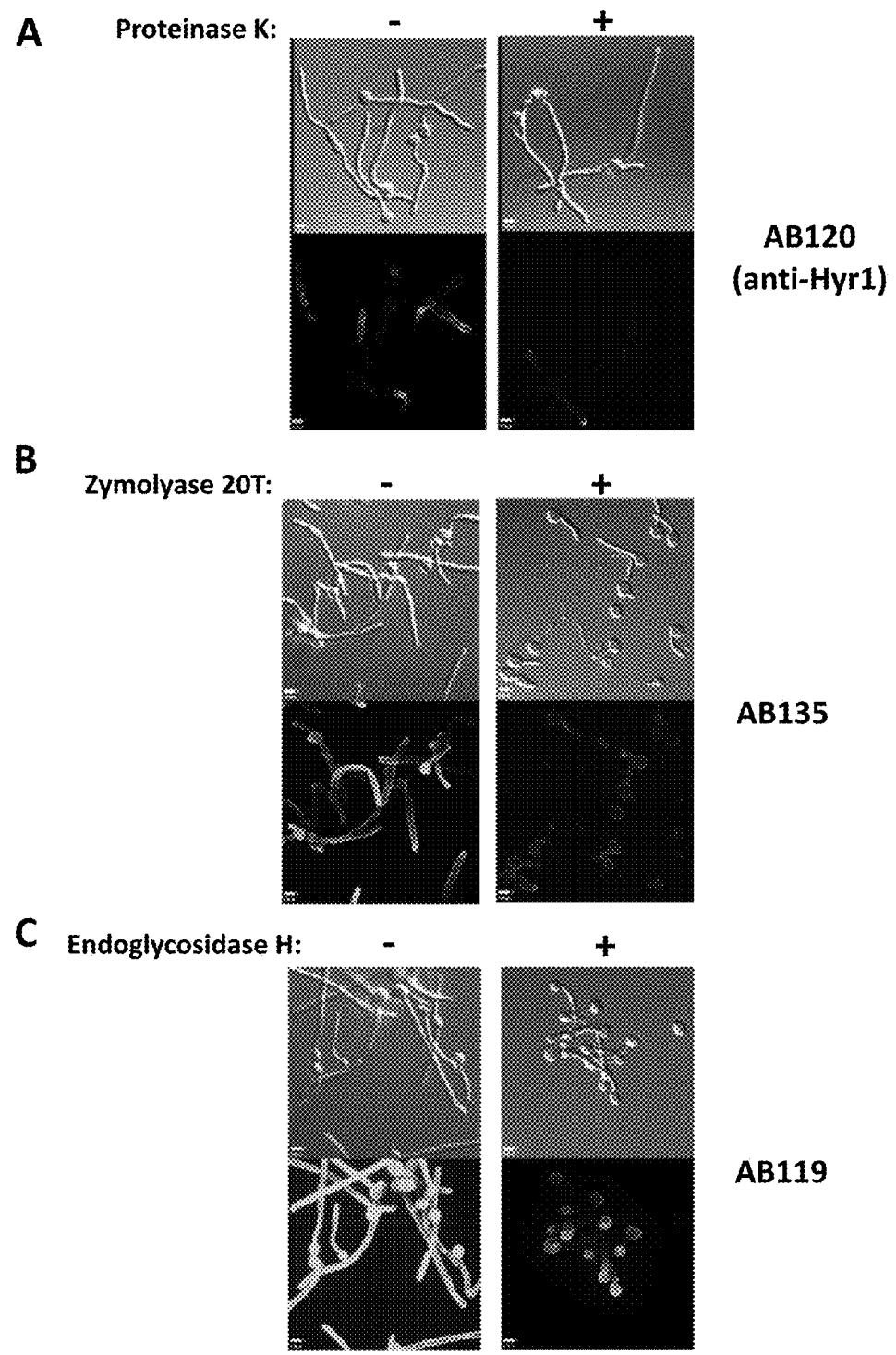

FIG. 15—Indirect immunofluorescence of mAbs binding to WT CAl4-Clp10 before and after enzymatic modification of the cell wall. Proteinase K treatment was used to reduce protein residues; Zymolyase 20T enzyme was used to digest B-1,3-glucans; Endoglycosidase H treatment reduced N-linked glycans on the CAl4-Clp10 cell wall. Decrease in indirect immunofluorescence after enzymatic treatments suggested the nature of the mAb epitopes. A fluorescently conjugated secondary goat anti-human IgG antibody was used to detect anti-*Candida* mAb binding. Scale bars represent 4 μm.

FIG. 16—Human monocyte-derived macrophage phagocytosis of live *C. albicans* cells pre-incubated with saline, isotype control mAb or anti-*Candida* mAb. (a) Time at which an uptake event occurred over the first 90 min of the assay following *C. albicans* pre-incubation with saline, an IgG1 control antibody, an anti-whole cell reactive mAb (AB119 and AB140) or an anti-Hyr1 mAb (AB120). Bars represent percentage of uptake events (n=2). (b) Percentage of these uptake events that occurred within the first 30 min of the assay. Dots represent average from individual experiments, line represents average (n=2) and (c) average time taken for a macrophage to engulf a live *C. albicans* cell following pre-incubation with saline, an IgG1 control antibody, an anti-whole cell mAb (AB119 and AB140) or an anti-Hyr1 mAb (AB120) at a MOI of 3 (n=2).

FIG. 17—Counterimmunoelectrophoresis of anti-*Candida* mAbs with *C. albicans*. Purified anti-*Candida* mAbs AB119, AB140 and AB118C101S reacted with yeast supernatant antigenic preparation and a crude yeast extract (a). AB119, AB140, AB118C101S and AB135 reacted with hyphal supernatant antigenic preparation and a crude hyphal extract (b).

Figure 18:
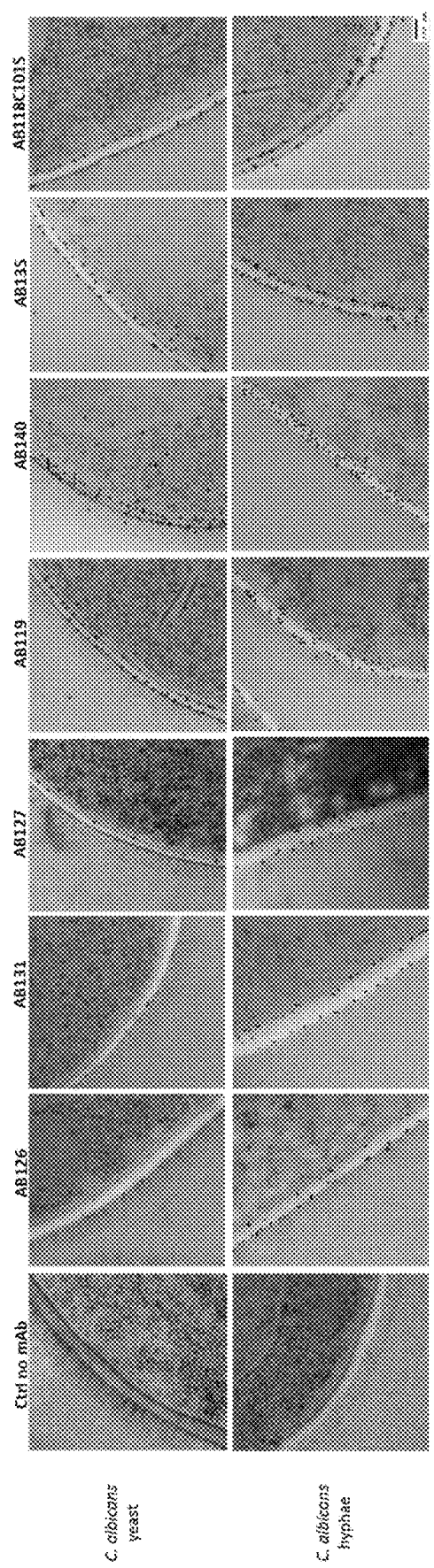

FIG. 18—Immunogold localization of anti-*Candida* mAbs to the cell wall of *C. albicans* yeast (top panel) and hyphal (bottom panel) cell walls.

EXAMPLE 1—GENERATION OF FULLY HUMAN ANTI-*CANDIDA* MABS BY SINGLE B CELL CLONING

The generation of recombinant mAbs through direct amplification of VH and VL genes from single B cells produces fully human, affinity matured mAbs with the native antibody heavy and light chain pairing intact (14). We employed this technology to generate human recombinant anti-*Candida* mAbs to a defined *C. albicans* antigen—the morphogenesis-regulated protein 1 (Hyr1) protein expressed only in the hyphal cell wall (40), and to *C. albicans* whole cell wall preparations. Hyr1 protein was selected based on its role in proposed role in resisting phagocyte killing and pre-clinical data demonstrating that a recombinant N-terminal fragment of Hyr1 confers protection in a murine model of disseminated candidiasis (23, 29, 41). Furthermore, because Hyr1 is expressed solely on *C. albicans* hyphal cells so mAbs generated against this protein would serve as *C. albicans*-specific markers. In addition we used *C. albicans* whole cell wall extracts as a target to screen against allows for the isolation of mAbs that bind to an array of different antigens, anticipating that some of the resulting mAbs would be pan fungal and therefore possess a broad spectrum of therapeutic activity and pan-*Candida* diagnostic specificity.

To enhance the likelihood of isolating *Candida*-related antibodies, the class switched memory (CSM) B cells used in this study were isolated from the blood of individuals who had recovered from a superficial *Candida* infection within a year of sampling. Donors were selected from a panel of volunteers and the levels of target-specific circulating IgG in the donor plasma was assessed via ELISA. In this screen, donor 85 demonstrated the greatest IgG activity against *C. albicans* whole cell and donor 23 had the highest IgG titre against Hyr1 (FIG. 2A). These donors were selected to provide the source of B cells to use for the generation of Candida-specific recombinant antibodies. After the isolation of CSM B cells from a donor, approximately 80000-150000 cells were plated out at 5 cells/well and activated with a cocktail of cytokines and supplements to promote secretion of IgG into the supernatant. A high throughput screening platform was then employed to facilitate the detection of IgG in the B cell supernatant against target antigens by ELISA. Positive ELISA hits enabled identification of wells containing B cells secreting antigen-specific IgG into the supernatant. Typically, approximately 0.05% wells/screen were positive (OD>4×background). Non-specific hits were identified and eliminated by performing an ELISA screen against two unrelated proteins—human serum albumin (HSA) and human embryonic kidney nuclear antigen (HEK NA). CSM B cells from wells that were positive for the antigen screen and negative for the unrelated protein screen were then lysed and used as the source for VH, Vκ-Cκ and Vλ-Cλ gene amplification via RT-PCR and nested PCR (FIGS. 2B, C). VH, Vκ-Cκ and Vλ-Cλ genes were sub cloned into the pTT5 mammalian expression vector and the sequences analysed (data not shown). Corresponding heavy and light chains originating from the same hit well were co-transfected into Expi293F cells for small scale whole IgG1 expression. From these co-transfections, recombinant mAbs that demonstrated binding to the original target were selected for large scale recombinant expression. These were then purified via affinity-based FPLC using a protein A resin and quality control checked via analytical mass spectrometry, SDS-PAGE gel analysis and analytical SEC (FIGS. 2D-G).

In total, 18 purified recombinant IgG1 mAbs were generated using the single B cell technology described above. Five of these mAbs bound to purified Hyr1 protein and 13 bound to C. albicans whole cells (Table S3).

EXAMPLE 2—PURIFIED RECOMBINANT ANTI-CANDIDA MABS EXHIBIT SPECIFIC TARGET BINDING

Purified anti-Hyr1 mAbs were primarily assessed for functionality through binding to the purified recombinant N-terminus of Hyr1 protein via ELISA. Four of the five mAbs demonstrated strong binding to the purified antigen with $EC_{50}$ values of 104 ng/ml, 76.5 ng/ml, 49.6 ng/ml and 53.3 ng/ml for AB120, AB121, AB122 and AB123 (FIG. 3A) respectively. AB124 bound to Hyr1 with a lower affinity with an $EC_{50}$ value of 1050 ng/ml. To examine the specificity of these mAbs for the target protein, all five were tested against the unrelated antigens HSA and HEK nuclear antigen as negative controls and demonstrated no binding (FIG. 13).

The purified recombinant anti-whole cell mAbs were originally screened and isolated against C. albicans overnight culture. As such, the initial QC of these mAbs was to assess their binding to C. albicans whole cells via ELISA. The majority of purified anti-whole cell mAbs bound C. albicans yeast cells with high affinity with $EC_{50}$ values ranging from 2.8 to 31.1 ng/ml (FIGS. 3B, C). AB134 and AB135, which have similar amino acid sequences, both demonstrated slightly lower affinity for the target with $EC_{50}$ values of 1060 and 224 ng/ml respectively (FIG. 3C).

Purified anti-whole cell mAbs exhibited a variety of affinities when binding to C. albicans cells where both yeast and hyphal morphologies were present (FIGS. 3D, E). The majority bound these cells with high affinity with $EC_{50}$ values ranging between 3 and 50 ng/ml. As observed with C. albicans yeast cell binding, AB134 and AB135 demonstrated slightly lower affinities with $EC_{50}$ values of 684 and 69.4 ng/ml. $EC_{50}$ values were used here as a simple comparison to demonstrate the variability in anti-whole cell mAbs binding to C. albicans cell surface antigens. Therefore this methodology generated a panel of mAbs which bound to a variety of specific cell targets. Specificity of the anti-whole cell mAbs for a target C. albicans antigen was assessed through binding to the two unrelated antigens HSA and HEK NA. All mAbs demonstrated no binding to these antigens confirming their specificity for the fungal cells (FIG. 14).

EXAMPLE 3—PURIFIED RECOMBINANT ANTI-CANDIDA MABS SHOW DISTINCT BINDING PATTERNS TO C. albicans and Other Fungal Species The recombinant anti-Hyr1 mAbs generated by single B cell technology were initially isolated by screening against N-terminus of Hyr1 protein and, following purification, demonstrated binding to this recombinant antigen (above). We then visualized binding of these mAbs to Hyr1 protein expressed on the C. albicans cell surface by immunofluorescent staining using a fluorescently labelled secondary anti-human IgG mAb for detection. It was observed that the anti-Hyr1 mAbs bound to the predicted cellular location on the hyphae, and not the WT C. albicans yeast cells grown in different culture conditions (FIG. 4A). We verified that the anti-Hyr1 mAbs did not bind to hyphae of a Δhyr1 null mutant (FIG. 4B) and that binding was restored in a C. albicans strain containing a single reintegrated copy of the deleted HYR1 gene (FIG. 4C).

Next we visualised binding to WT C. albicans for the anti-whole cell mAbs via indirect immunofluorescent staining. The anti-whole cell mAbs demonstrated a range of binding profiles to WT C. albicans (FIG. 5). mAbs AB118, AB119, AB129, AB130, AB133, AB134, AB135, AB139, AB140 bound strongly to both C. albicans yeast and hyphae (FIG. 5A). AB132 bound to both yeast and hyphae but exhibited stronger binding to hyphae (FIG. 5B). AB126 and AB131 appeared to be hypha-specific (FIG. 5C) and AB127 stained the mother yeast cell and the tip of the growing hyphae (FIG. 5D). Therefore the panel of antibodies apparently detected both morphology specific and morphology-independent epitopes.

C. albicans cells were enzymatically treated with proteinase K, endoglycosidase H (endo-H) and zymolyase 20T and assessed for mAb binding. Proteinase K treatment reduced AB120 (anti-Hyr1) but not anti-whole cell mAbs binding to C. albicans confirming that anti-Hyr1 antibody recognised a protein epitope (FIG. 15a). Following zymolyase 20T and endo-H treatments, binding of other anti-whole cell mAbs decreased suggesting that the cognate epitopes might be β-glucan or N-mannan respectively (FIG. 15b, c). Some anti-whole cell mAbs demonstrated increased fluorescence after enzymatic treatment suggesting that their epitopes might be located deeper in the cell wall.

Commensurate with the C. albicans-specific nature of HYR1, anti-Hyr1 mAbs only bound to C. albicans and not to a range of other Candida species (FIG. 6a). In contrast, a range of binding patterns were observed for the binding of anti-whole cell mAbs to other pathogenic fungal species. The majority of mAbs bound strongly to the closely related species C. dubliniensis, C. tropicalis, C. parapsilosis and C. lusitaniae. There was little binding of mAbs to the more distantly related C. glabrata and C. krusei. Only the homologous AB131 and AB132 antibodies demonstrated some weak binding to *C. krusei*(FIG. 6*b*).

To assess for pan-fungal binding activity, all the anti-whole cell mAbs were tested against *A. fumigatus. C. neoformans, C. gattii, P. carinii, M. circinelloides* and *M. dermatis* but no binding was observed (FIG. 6*b*). Therefore the anti-Hyr1 mAbs are *C. albicans*-specific and the anti-whole cell mAbs demonstrate a variety of binding patterns to WT *C. albicans* and other pathogenic *Candida* species, indicating that they target a range of different antigens and the expression levels of these antigens varies from species to species.

In conclusion, all purified recombinant mAbs generated by this single B cell technology bound specifically to their target antigens with high affinity. As expected, the anti-whole cell mAbs demonstrated distinct binding patterns to WT *C. albicans* and other pathogenic fungi, indicating that they target a range of different antigens and the expression levels of these antigens varies from species to species.

EXAMPLE 4—PURIFIED RECOMBINANT ANTI-*CANDIDA* MABS OPSONISE *C. ALBICANS* FOR PHAGOCYTOSIS BY MACROPHAGES

Phagocytic cells of the innate immune system are the first line of defence against fungal pathogens. Antibody binding enhances phagocytic clearance of pathogens. We utilised a live cell phagocytosis assay to examine whether the anti-*Candida* mAbs generated in this study opsonized *C. albicans* for phagocytosis by J774.1 macrophages and human monocyte-derived macrophages. The macrophages were challenged with live, *C. albicans* CAI4-Clp10 which had been pre-incubated with an anti-*Candida* mAb, an isotype control mAb or saline for 1 h. Live cell video microscopy using our standard phagocytosis assay (42, 43) was employed to determine the degree of opsonisation. No significant difference was observed between the saline control and anti-*Candida* mAb groups in terms of the overall number of *C. albicans* cells taken up during the 3 h by macrophages. However, there was a difference in the time by which the majority of uptake events had occurred (FIG. 7A). *C. albicans* cells that had been pre-incubated with either AB118, AB119 or AB140 (anti-whole cell mAbs) were taken more rapidly compared to the saline control-treated fungal cells, the IgG1 control pre-incubated fungal cells or AB120 pre-incubated fungal cells. The percentage of uptake events occurring by 20 min was 21±10, 54±9, 22±5 and 68 2, 44.3±0.6 and 7±2 (mean±SD) for saline control, AB118, AB120, AB140, AB119 and isotype control respectively (FIG. 7A). A majority of *C. albicans* cells pre-incubated with AB118, AB119 or AB140 were taken up as yeast cells and the majority of cells taken up by the saline control group, AB120 group and isotype control group, were hyphal cells (FIG. 7B).

EXAMPLE 5—MACROPHAGES RAPIDLY ENGULF MAB-BOUND *C. ALBICANS* CELLS THROUGH FCγR BINDING

Next we used live cell video microscopy and image analysis to examine whether there was any difference in the rate of engulfment between *C. albicans* cells pre-incubated with saline compared to *C. albicans* cells pre-incubated with selected anti-*Candida* mAbs. As shown previously we defined the rate of engulfment as the time taken from establishment of cell-cell contact to the time at which a *C. albicans* cell had been completely engulfed by a macrophage as indicated by its loss of FITC green fluorescence (42, 43) (FIGS. 8A-C). When *C. albicans* yeast cells were pre-incubated with AB120 (anti-Hyr1 mAb) there was no difference in the rate of engulfment from the saline control or IgG1 control mAb however, in the presence of either AB118, AB119 or AB140 (anti-whole cell mAbs), fungal cells were engulfed at a significantly faster rate compared to the saline control and IgG1 control mAb, (FIG. 8D). The hypha-specific mAb AB120 stimulated faster macrophage engulfment of *C. albicans* hyphal cells by macrophages—taking an average of 5.8±0.3 min to engulf opsonised hyphae compared to 8.8±0.8 min for the control (FIG. 8E).

Similar observations were obtained using human monocyte-derived macrophages (FIG. 16).

Blocking FcγRs on the surface of the macrophage decreased the rate of engulfment of AB140-bound *C. albicans* compared to that of the saline control (FIG. 9) indicating that the increased rate of engulfment of mAb-bound *Candida* cells is, at least in part, due to uptake through the FcγRs.

EXAMPLE 6—MACROPHAGES MIGRATE FURTHER, FASTER AND MORE DIRECT TOWARDS ANTI-*CANDIDA* MAB BOUND *C. ALBICANS* CELLS

We showed that antibody-bound *C. albicans* cells were cleared earlier by macrophages than control cells. To determine the effect of antibody binding on uptake dynamics, we used imaging analysis to digitise the migration of macrophages until their first uptake event, measuring the distance travelled, directionality and velocity of the macrophage towards control or antibody-bound fungal cells. Macrophages travelled further and at a greater velocity towards *C. albicans* yeast cells that had been pre-incubated with a whole-cell mAb (AB140) compared to control fungal cells or those pre-incubated with IgG1 control mAb (FIG. 10 A,B). Furthermore we observed that macrophages moved in a more directional manner towards antibody-bound *C. albicans* cells compared to control cells or those pre-incubated with IgG1 control mAb (FIGS. 10 C, D and E).

EXAMPLE 7—ANTI-WHOLE CELL MAB REDUCES FUNGAL BURDEN IN A MODEL OF DISSEMINATED CANDIDIASIS

To determine whether the anti-*Candida* mAbs possessed therapeutic potential in vivo, their action was assessed in a murine model of systemic candidiasis (44). *C. albicans* SC5314 yeast cells were pre-incubated for 1 h with either saline, an IgG1 isotype control mAb, AB119 (anti-whole cell) or AB120 (anti-Hyr1) before iv injection into the mouse lateral tail vein. Disease progression was monitored by weight change and kidney fungal burdens at day 3 which together generated an overall outcome score for disease progression (44). When SC5314 was pre-incubated with AB120 there was no decrease in fungal burden compared to the saline control or the IgG1 control mAb (FIG. 11A). However, when AB119 was pre-incubated with SC5314, there was a significant decrease in kidney fungal burden compared to the saline control (FIG. 11A, p<0.01). This was also considerably less than the kidney fungal burden for the IgG1 isotype control. By weight change there was no significant difference in disease outcome score between AB120 and the saline control and isotype control (FIG. 11B). However, mice that had been injected with SC5314 pre-incubated with AB119 had a significantly lower disease outcome score than both the saline control group (p<0.01) and the isotype control group (p<0.05) indicating that when AB119 is present, the mice are able to clear infection more quickly and disease progression is limited (FIG. 11B). Therefore exposure to antibody improved the survival of mice in a systemic disease model.

EXAMPLE 8—DISCUSSION OF EXAMPLES 1-7

Monoclonal antibodies (mAbs) have the potential to be used in multiple fungal therapy and disease management situations. Here we describe and use for the first time a novel technology facilitating the isolation of fully human anti-*Candida* mAbs against whole cells and a specific cellular target. These mAbs were derived directly from single B cells from donors with a history of mucosal *Candida* infection and demonstrated distinct binding profiles to *C. albicans* and other pathogenic fungi, as well as the ability to opsonise fungal cells and to enhance phagocytosis and show partial protection in a murine model of disseminated candidiasis.

mAbs-based agents have been identified as an alternative strategy to complement the medical gaps associated with current antifungal treatments and diagnostics (13, 45, 46). In this study we generated 18 fully human recombinant anti-*Candida* mAbs through the direct amplification of mRNA isolated from VH and VL antibody genes produced naturally in vivo in response to a *Candida* infection. By employing this method, the purified, affinity matured recombinant mAbs generated were less likely to be immunogenic, had importantly retained their native antibody heavy and light chain pairings, and therefore are more likely to be of therapeutic benefit (35). IgG1 was selected as the antibody scaffold because this isotype makes up the majority of mAbs in the clinic and so is the best characterised in terms of drug development (47, 48). Thirteen of the mAbs generated bound to *C. albicans* whole cell and 5 bound to recombinant purified Hyr1 protein—a protein which is considered to be important for *C. albicans* resistance to phagocytosis and is currently in development as an experimental vaccine (29, 41) demonstrating that this novel technology can be utilised for screening against a wide range of specific antigens.

An antibody that recognises an antigen expressed across different fungal species could be highly beneficial as a pan-fungal therapeutic. At the same time, one of the major contributors to poor prognosis in the clinic is the lack of accurate and timely diagnostics with a knock on delay in appropriate treatment (6, 7, 49). In this case, it would be more beneficial to have a species-specific antibody which recognises an antigen only expressed on one species. As such, we assessed binding of our panel of mAbs to a number of emerging and resistant pathogenic fungi. We observed that anti-Hyr1 mAbs bound solely to *C. albicans* hyphae, correlating with findings that have reported that Hyr1 is only expressed on *C. albicans* hyphal cells (29, 40, 50). The binding pattern of anti-whole cell mAbs was more varied with the majority of mAbs binding strongly to the species that are closely related to *C. albicans* such as the emerging pathogens *C. tropicalis* and *C. parapsilosis* (51). As expected, little or no binding was observed to the more evolutionarily distinct species *C. glabrata* and *C. krusei*. Altogether this demonstrates that the novel technology employed here can be utilised to generate species-specific as well as pan fungal mAbs, which has great implications in terms of anti-fungal drug discovery and diagnostics. Furthermore, these mAbs could be utilised to isolate and identify protective antigens for development as fungal vaccines.

One of the many ways mAbs exert their protective effects is through opsonizing cells for phagocytosis (15). We have shown previously that by employing live cell imaging we can breakdown this process down into its component parts, thus allowing us to do a more in-depth analysis on the effect of mAbs on the individual stages of phagocytosis (42, 43). Here we observed that when yeast and hyphal cells were coated with an anti-whole cell mAb or a hyphal cell was coated with an anti-Hyr1 mAb, cells were engulfed at a significantly faster rate compared to unopsonized cells, and this was through engagement of the FcγR. Furthermore, macrophages migrated further, faster and in a more direct manner towards opsonized *C. albicans* cells and this contributed to earlier clearance of fungal cells.

A number of invasive infections occur in the immunocompetent patient population as a consequence of severe trauma, and in these situations opsonizing mAbs could be a viable treatment option. The majority of antibody therapeutics in the clinic are hIgG1 so this isotype has been routinely tested pre-clinically in murine models of disease (47). Furthermore, the literature shows that hIgG1 binds to all activating mFcγRs with a similar profile to the most potent IgG isotype in mice, mIgG2a, validating the use of mouse models to assess Fc-mediated effects of hIgG1 mAbs (47). As such, we utilised an established three-day murine model of disseminated candidiasis (44, 52) to assess the efficacy of anti-*Candida* mAbs in vivo and observed a significant decrease in kidney fungal burden and overall disease outcome score when *C. albicans* was pre-incubated with an anti-whole cell mAb.

We have generated fully human antibodies from single B-cells to create reagents that have high specificity for targets with utility in the antifungal diagnostic and therapeutic markets. The antibodies are of high affinity and are and can be synthesised in milligram quantities under defined conditions for heterologous protein expression.

The relative by which these antibodies can be produced means that they could be used singly or in multiplex formats to create novel polyvalent diagnostic tests, as vaccine Candidates or as therapeutic delivery systems to target toxic molecules to specific microbial or cellular targets.

EXAMPLE 9—CIE ANALYSIS

FIG. 17 shows the results of counterimmunoelectrophoresis (CIE) analysis. This shows selected mAbs were able to detect *C. albicans* antigens in a format commonly used for the diagnosis of patients with a *Candida* infection.

EXAMPLE 10—TEM ANALYSIS

FIG. 18 shows transmitting electron microscopy (TEM) images illustrating the binding of a select panel (one mAb from each CDR3 amino acid sequence cluster) of the anti-whole cell mAbs to *C. albicans* yeast and hyphal cell walls via immunogold labelling. The images show that the mAbs are very specific to the cell wall and that there are a variety of binding targets, for example AB126, AB127 and AB131 appear mainly to bind to hypha, whereas AB118C101S, AB119, AB140 and AB135 appear to bind to more abundantly expressed targets in both yeast and hyphal cells.

General Methods

Candida Strains and Growth Conditions

*C. albicans* serotype A strain CA14+Clp10 (NGY152) was used as a control and its parent strain CA14, used to construct the Δhyr1 null mutant *C. albicans* strain (40) and the hyr1 re-integrant strain (unpublished). The clinical isolates *C. albicans* SC5314, *C. glabrata* SC571182B, *C. tropicalis* AM2005/0546, *C. parapsilosis* ATCC22019, *C. lusitaniae* SC5211362H, *C. krusei* SC571987M, *C. dubliniensis* CD36 are shown in Table S1. All strains were obtained from glycerol stocks stored at −80° C. and plated onto YPD plates (2% (w/v) mycological peptone (Oxoid, Cambridge, UK), 1% (w/v) yeast extract (Oxoid), 2% (w/v) glucose (Fisher Scientific, Leicestershire, UK) and 2% (w/v) technical agar (Oxoid)). *Candida* strains tested were routinely grown in YPD (see above without the technical agar) except in the in vivo experiments where strains were grown in NGY medium (0.1% (w/v) Neopeptone (BD Biosciences), 0.4% (w/v) glucose (Fisher Scientific), 0.1% (w/v) yeast extract (Oxoid). *Aspergillus fumigatus* clinical isolate V05-27 was cultured on Potato Dextrose Agar slants for seven days before the spores were harvested by gentle shaking with sterile 0.1% Tween 20 in PBS. Harvested spores were purified, counted and re-suspended at a concentration of $1 \times 10^8$ spores/ml. Swollen spores were generated by incubation in RPMI media for 4 h at 37° C.

*Malassezia dermatis* CBS9169 was cultured on Modified Dixon agar (3.6% (w/v) Malt extract (Oxoid), 1% (w/v) Bacto peptone (BD Biosciences), 2% (w/v) Bile salts (Oxoid), 1% (w/v) Tween40 (Sigma), 0.2% (w/v) Glycerol (Acros Organics), 0.2% (w/v) Oleic acid (Fisher Scientific), 1.5% technical Agar (Oxoid)) supplemented with chloramphenicol (0.05% (w/v) Sigma) and cycloheximide (0.05% (w/v) Sigma)). Overnight culture of *M. dermatis* was grown in Modified Dixon Medium. *Mucor circinelloides* CBS277.49 was grown on Potato Dextrose Agar for 7 days before spores were harvested in PBS and filtered through 40 μm Nylon Cell Strainer (BD Biosciences). *Cryptococcus neoformans* KN99a and *Cryptococcus gattii* R265 were grown in YPD overnight, washed in PBS and $1 \times 10^7$ cells were added to 6 ml RPMI+10% FCS in 6 well-plates. Plates were incubated at 37'C+5% $CO_2$ for 5 days to induce capsule formation. Harvested cells were washed in PBS. Rat lung tissue isolates of *Pneumocystis carinii* M167-6 were washed in PBS and immunostained.

Generation of Recombinant Hyr1 N— Protein

The recombinant N-terminus of the Hyr1 protein (amino acids 63 to 350—Table S2) incorporating an N-terminal 6×His tag was expressed in HEK293F cells and purified by nickel-based affinity chromatography using a nickel NTA superflow column (QIAGEN, USA). Fractions containing the recombinant N-terminus of the Hyr1 protein were pooled and further purified via Analytical Superdex 200 gel filtration chromatography (GE Healthcare, USA) in PBS. QC of the recombinant protein via SDS-PAGE gel analysis, analytical size exclusion chromatography (SEC) and Western blot (using an anti-His antibody for detection) confirmed a protein of 32 kDa (data not shown).

Identification of Human Anti-Hyr1 and Anti-Whole Cell mAbs from Donor B Cells PBMC Isolation In brief, peripheral venous blood from donors who had recovered from a *Candida* infection within the last year was collected in EDTA-coated vacutainers tubes and pooled. PBMCs and plasma were separated from the whole blood suspension via density gradient separation using Accuspin System-Histopaque-1077 kits (Sigma-Aldrich) according to manufacturer's instructions. Following separation, the plasma layer was aspirated and stored at 4° C. for later analysis of antibody titre and the PBMC layer was aspirated and washed in PBS and centrifugation at 250×g for 10 min three times before final resuspension at a concentration of $1 \times 10^7$ cells/ml in R10 media (RPMI 1640 (Gibco, Life Technologies), 10% FCS, 1 mM sodium pyruvate (Sigma), 10 mM HEPES (Gibco, Life Technologies), 4 mM L-glutamine (Sigma), 1×penicillin/streptomycin (Sigma)) containing additional 10% FCS and 10% DMSO. PBMCs were split into 1 ml aliquots and stored in liquid nitrogen until they were required.

Purification of Donor Plasma

IgG was purified from donor plasma using VivaPure MaxiPrepG Spin columns (Sartorius Stedman) according to manufacturer's instructions. In brief, plasma sample was applied to the spin column to facilitate IgG binding. The column was washed twice in PBS and then bound IgG was eluted in an amine buffer, pH 2.5 and neutralized with 1 M Tris buffer, pH8. Eluted IgG concentration was measured by absorbance at 280 nm using a NanoVue Plus Spectrophotometer (GE Healthcare).

Circulating IgG Enzyme-Linked Immunosorbent Assay (ELISA) to Identify Donors with B Cells to Take Forward To identify the donor to use for subsequent class switched memory (CSM) B cell isolation and activation, ELISAs were carried out against the target antigens using IgG purified from donor plasma. NUNC maxisorp 384-well plates (Sigma) were coated with *C. albicans* overnight culture (whole cell) or 1 μg/ml purified, recombinant N-terminus hyr1 protein antigen in 1×PBS and incubated at 4° C. overnight. The next day, wells were washed three times with wash buffer (ixPBS+0.05% Tween) using a Zoom Microplate Washer (Titertek). Wells were then blocked with block buffer (1×PBS+0.05% Tween+0.5% BSA) for 1 h at room temperature with gentle shaking to inhibit non-specific binding. After three washes (as above), titrated purified IgG or IVIG in block buffer was added in duplicate, and the plates were incubated for 2 h at room temperature with gentle shaking. Wells were washed with wash buffer as above before addition of goat anti-human IgG, HRP conjugated (ThermoScientific) secondary antibody at 1:5000 dilution in blocking buffer. Plates were incubated for 45 min at room temperature with gentle shaking. To develop the ELISA, wells were washed three times with wash buffer (as above) before the addition of TMB (Thermo Scientific). Plates were incubated at room temperature for 5 min to allow the blue colour to develop and the reaction was quenched by the addition of 0.18 M sulphuric acid. The plates were then read at an OD of 450 nm on an Envision plate reader (PerkinElmer). Labstats software in Microsoft Excel was used to generate concentration-response curves for $EC_{50}$ determination and donor selection for subsequent CSM B cell isolation and activation.

Isolation of Class Switched Memory B Cells

The PBMCs from donors who displayed a strong IgG response to the antigen of interest in the screening ELISA were taken forward for CSM B cell isolation and activation. The process of generating recombinant mAbs from a single donor's B cells to one particular antigen, beginning with the isolation of CSM B cells all the way through to expression and purification of recombinant mAbs, was termed an 'Activation'. For each Activation, $5 \times 10^7$ PBMCs were removed from the liquid nitrogen store and thawed by adding pre-warmed R10 media drop wise to the cells. The diluted cell suspension was then transferred into a fresh polypropylene tube containing pre-warmed R10, resulting in a final cell dilution of approximately 1:10. Benzonase nuclease HC, purity >99% (Novagen) was added at a 1:10000 dilution (to ensure any lysed cells and their components didn't interfere with the live cells), and the cells were centrifuged at 300×g for 10 min at room temperature and the supernatant removed. PBMCs were then washed again in R10 before final resuspension in 1 ml R10 for PBMC cell number and viability determination.

Isolation of class switched memory B cells from PBMCs was carried out by magnetic bead separation using a Switched Memory B cell isolation kit with Pre-Separation Filters and LS columns (MACS Miltenyi Biotec) according to manufacturer's instructions. In brief, counted PBMCs were incubated with a cocktail of biotin-conjugated antibodies against CD2, CD14, CD16, CD36, CD43, CD235a (glycophorin A), IgM and IgD. Cells were then washed and incubated with anti-biotin microbeads. Following another wash step, the suspension was passed through a Pre-Separation Filter (to remove cell aggregates) before applying it to an LS column where the magnetically labelled cells were retained in the column and the unlabelled CSM B cells passed through and could be collected in the flow-through for determination of cell number and viability.

Activation of CSM B Cells

To activate CSM B cells and promote antibody secretion into the supernatant, a mixture of cytokines, mAb, TLR agonist and a supplement were added to the R10 media (see above) to make complete R10 media. CSM B cells were resuspended in complete R10 media at 56 cells/ml and then plated out at 90 µl/well (5 cells/well) in ThermoFisher Matrix 384 well plates using a Biomek FX (Beckman Coulter). Cells were incubated at 37° C., 5% $CO_2$ for seven days. On day 7, 30 µl/well of supernatant was removed and replaced with 30 µl fresh complete R10. On day 13, all the supernatant was harvested from all plates and screened against the antigen of interest via ELISA. B cell activation and culturing was monitored by measuring IgG1 concentrations in B cell supernatants at day 7 and day 13.

B Cell Supernatant Screen Against Target Antigens Via ELISA

For B cell supernatant screening against target antigens, NUNC maxisorp 384-well plates (Sigma) were coated with *C. albicans* overnight culture (whole cell) or 1 µg/ml purified, recombinant N-terminus hyr1 protein antigen in 1×PBS and incubated at 4° C. overnight. Wells were washed three times with wash buffer using a Zoom Microplate Washer (Titertek) as above before incubation with blocking buffer for 1 h at room temperature with gentle shaking. After another three washes (as above), B cell supernatant was added and the plates incubated for 2 h at room temperature with gentle shaking. Wells were washed with wash buffer as above before addition of goat anti-human IgG, HRP conjugated (ThermoScientific) secondary antibody at 1:5000 dilution in blocking buffer and incubation for 45 min at room temperature with gentle shaking. ELISAs were developed and plates read at an OD of 450 nm on an Envision plate reader (PerkinElmer).

Positive hits were defined as wells with an $OD_{450}$ reading >4× background. B cells in 'positive hit' wells were resuspended in lysis buffer (ml DEPC-treated H2O (Life Technologies), 10 µl 1 M Tris pH 8, 25 µl RNAsin Plus RNAse Inhibitor (Promega)) and stored at −80° C.

Generation of Recombinant Anti-Hyr1 and Anti-Whole Cell IgG1 mAbs: Amplification of VH, Vκ-Cκ and Vλ-Cλ Genes—cDNA Synthesis and PCR A schematic of the cloning protocol is shown in FIG. 12. Primers used for the RT-PCR reaction were based on those used by Smith et. al., (36). To ensure all possible VH germline families were captured during the amplification, four forward primers specific to the leader sequences encompassing the different human VH germline families (VH1-7) were used in combination with two reverse primers; both placed in the human CgCH1 region. For the RT-PCR of human Vκ-Cκ genes, three forward primers specific to the leader sequences for the different human Vκ germline families (Vκ1-4) were used with a reverse primer specific to the human kappa constant region (Cκ) and two further reverse primers which were specific to the C- and N-terminal ends of the 3' untranslated region (UTR). To capture the repertoire of human Vλ genes, 7 forward primers capturing the leader sequences for the different human Vλ germline families (Vλ1-8) were used in a mixture with two reverse primers which were complementary to the C- and N-terminal ends of the 3' UTR and another reverse primer specific to the human lambda constant region (Cλ).

Prior to cDNA synthesis, B cell lysates were thawed and diluted 1:5, 1:15 and 1:25 in nuclease-free $H_2O$ (Life Technologies) before addition of $oligodT_{20}$ (50 µM) (Invitrogen, Life Technologies) and incubation at 70° C. for 5 min. Reverse transcription and the first PCR reaction (RT-PCR) were done sequentially using the QIAGEN OneStep RT-PCR kit according to manufacturer's instructions. For this step and the subsequent nested PCR step, amplification of the variable domain of human Ig heavy chain genes (VH), the variable and constant domains of human Ig kappa light chain genes (Vκ-Cκ) and the variable and constant domains of human Ig lambda light chain genes (Vλ-Cλ), were done in separate reactions. In brief, a reaction mixture was prepared containing QIAGEN OneStep RT-PCR Buffer 5×, dNTPs (10 mM), gene-specific forward and reverse primer mixes (10 µM), QIAGEN OneStep RT-PCR Enzyme Mix and nuclease-free $H_2O$. Reaction mixture was then added to wells of a 96-well PCR plate before addition of neat or diluted (1:5, 1:15, 1:25) B cell lysate as the template, resulting in a final reaction volume of 50 µl/well. The following cycling conditions were used for the RT-PCR reaction; 50° C. for 30 min, 95° C. for 15 min then 35-40 cycles of (94° C. for 1 min, 55° C. for 1 min and 72° C. for 1 min) with a final extension at 72° C. for 10 min.

Amplification of VH, Vκ-Cκ and Vλ-Cλ Genes—Nested PCR Reaction

Nested PCR reactions were carried out using the PCR products from the RT-PCR reaction as the template, nested gene-specific primers based on Smith et al. (36) and Platinum PCR SuperMix High-Fidelity (Invitrogen, Life Technologies). A total of 27 forward primers specific for the VH framework 1 (FW1) sequence were used together with two reverse primers specific for the framework 4 (FW4) region of the VH gene. For nested PCR of the Vκ-Cκ gene, a mixture of 18 forward primers specific for human Vκ FW1 sequence were used with a reverse primer specific to the human kappa constant region 3' end. For amplification of the Vλ-Cλ gene, a mixture of 31 forward primers specific for human Vλ FW1 sequences were used together with a reverse primer that was placed at the 3' end of the human lambda constant region. The primers used to generate the PCR fragments in these nested PCR reactions contained 15 bp extensions which were complementary to the target downstream pTT5 expression vector. Reaction mixtures containing Platinum PCR SuperMix High Fidelity, gene-specific forward primer mix (10 µM) and gene specific reverse primer mix (10 µM) was added to wells in a 96-well PCR plate before addition of cDNA template. Amplification of VH genes, Vκ-Cκ genes and Vλ-Cλ genes, were done in separate reactions. After the nested PCR reaction, samples were analysed via agarose gel electrophoresis and positive hits identified and taken forward for downstream InFusion cloning with pTT5 mammalian expression vector.

pTT5 Mammalian Expression Vector Preparation

The pTT5mammalian expression used for mAb expression (licensed from the National Research Council of Canada (NRCC)) (53). The pTT5 vector plasmid contained an IgG1 heavy chain gene in the multiple cloning site so digestion to generate the heavy chain (HC) backbone for downstream sub cloning of VH was done by double digestion using FastDigest Restriction enzymes (Thermo Scientific) with BssHII before the leader sequence of the VH region and SaA restriction after the FW4 of the VH domain. This yielded the heavy chain constant region in the vector backbone. For double digestion of the vector to generate the light chain (LC) backbone, the whole IgG1 heavy chain gene was with BssHII and BamHI astDigest Restriction enzymes (Thermo Scientific) to generate the vector ready for insertion of either κ-Cκ or Vλ-Cλ. Digestion reactions to generate HC and LC backbones were carried out separately. Following confirmation of digestion, samples were run on a 1% agarose gel and bands were excised from the gel and purified using the QIAquick Gel Extraction kit (QIAGEN). DNA was quantified on a NanoVue Plus Spectrophotometer (GE Healthcare). To prevent vector self-ligation, the 3'- and 5'-termini of the linearized plasmids were dephosphorylated using FastAP Thermosensitive Alkaline phosphatase (Thermo Scientific). Reaction mixtures were cleaned up using the MinElute Reaction Cleanup Kit (QIAGEN) and then run on a 1% agarose gel. Bands corresponding to dephosphorylated HC and LC backbones were excised from the gel and purified using the QIAQuick Gel Extraction kit (QIAGEN) as above. Dephosphorylated linearized vector DNA was quantified on a NanoVue Plus spectrophotometer (GE Healthcare).

In-Fusion Cloning

The In-Fusion HD Cloning Kit (Clontech, USA) was used to clone the IgG VH, Vκ-Cκ and Vλ-Cλ genes into a pTT5 mammalian expression vector. To avoid the need for nested PCR product purification before cloning, cloning enhancer (Clontech, USA) was added to each nested PCR product in a 96-well PCR plate and incubated at 37° C. for 15 min, then 80° C. for 15 min. The cloning enhancer-treated PCR product was then added to the In-Fusion Enzyme Premix and linearized vector DNA (~5-10 ng). Reactions were made up to 10 µl with nuclease-free H$_2$O and incubated for 15 min at 50° C. Samples were then either stored at −20° C. or placed on ice before transformation of Stellar Competent cells (Clontech). For transformation, 2 µl of each In-Fusion reaction mixture was added to cells in a 96-well plate format, and left on ice for 30 min before heat shock at 42° C. for 40 sec and then returning to ice for 2 min. Cells were then recovered in SOC medium (Clontech, USA) with gentle shaking at 37° C. for 45-60 min before plating out onto LB agar plates (1% (w/v) tryptone, 0.5% (w/v) yeast extract, 1% (w/v) NaCl, 1.5% (w/v) agar) containing 100 µg/ml ampicillin. Plates were incubated at 37° C. overnight and single colonies picked the next day.

Plasmid DNA Generation for Transfection

Following transformation, 8-16 single colonies per initial hit well for VH, Vκ and Vλ were picked and used to inoculate 2×TY media containing 100 µg/ml ampicillin in a Greiner deep well, 96-well plate (Sigma). VH, Vκ and Vλ plates were set up separately with the same plate layout to facilitate visual screening. Cells were grown at 370° C., 200 rpm overnight, and glycerol stocks were made the following day and stored at −80° C. To ensure accurate tracking of DNA sequences for downstream sequencing and transfections, each well inoculated by a single colony was given a unique ID based on the colony's original hit well and its position in the deep well 96 well plate following transformations. To obtain plasmid DNA for gene sequencing and small scale mammalian transfections, DNA minipreps from the overnight cultures were carried out in a 96-well plate format using the EPmotion (Eppendorf), according to manufacturer's instructions. DNA not taken for gene sequencing was stored at −20° C. until required for small scale transfections. Sequence data was analysed for CDR diversity and comparisons to germline sequences and used to identify clones to take forward for small scale transfection.

Small Scale Expression of Recombinant mAbs

Following VH, Vκ and Vλ gene sequencing, a file was generated containing all possible VH and Vκ/Vλ combinations resulting from the original hit wells from the primary ELISA screen. Automated mixing of the native heavy and light chain DNA pairing combinations (1.5 µg of HC plasmid DNA and 1.5 µg of LC plasmid DNA) into a new 96-well plate was facilitated through a HAMILTON MICROLAB® Starline liquid handling platform (Life Science robotics, Hamilton Robotics). Subsequent mixed DNA was used for small scale transient transfection of 3 ml of suspension cultured Expi293F cells (Life Technologies, USA) at a density of 2.5×10$^6$ cells/ml in 24-well tissue culture plates using the Expifectamine 293 Transfection kit (Life Technologies, USA) in accordance with manufacturer's instructions. Expi293F cells were maintained in pre-warmed (37° C.) sterile Expi293 expression media (Invitrogen) without antibiotics at 37° C., 7% CO$_2$, 120 rpm shaking. Supernatants were harvested on day 6 and recombinant mAb expression was quantified using anti-human IgG Fc sensors on an Octet QK$^e$ (ForteBio, Cλ, USA) for identification of mAbs to upscale.

Large Scale Expression, Purification and QC of Recombinant mAbs

For downstream large scale mammalian transfections, where a greater amount of DNA was required, DNA was prepared using a QIAGEN Plasmid Maxi Kit (QIAGEN, USA) according to manufacturer's instructions with typical yields of 1.5 µg/µl.

For large scale mAb expression, 100 µg of total DNA (50 µg of HC plasmid DNA and 50 µg LC plasmid DNA) was used to transiently transfect 100 ml of suspension cultured Expi293F cells (Life Technologies, USA) at a density of 2.5×10$^6$ cells/ml using the Expifectamine 293 Transfection Kit (Life Technologies, USA) in accordance with the manufacturer's instructions. Supernatants were harvested on day 6 and recombinant mAb expression was quantified as above using an Octet QK$^e$ (ForteBio). Recombinant mAbs were purified via affinity based Fast Protein Liquid Chromatography using HiTrap Protein A HP columns on an ÄKTA (GE Healthcare) and eluted in 20 mM citric acid, 150 nM NaCl (pH2.5) before neutralisation with 1 M Tris buffer (pH8). Purified mAbs were dialysed in PBS overnight and IgG concentration was quantified on a NanoVue Spectrophotometer (GE Healthcare). All purified recombinant mAbs were quality control checked via SDS-PAGE gel analysis using 4-12% Bis-Tris SDS-PAGE gels under reducing and non-reducing conditions to confirm mass, analytical size exclusion chromatography (SEC) to check for protein aggregation/degradation and analytical mass spectrometry to confirm the amino acid sequence identity of each mAb. Purified recombinant mAbs were also tested for functionality by binding to target antigen/whole cell via ELISA.

ELISA with Purified Recombinant mAbs

For confirmation of binding to target as purified recombinant mAbs an ELISA was carried out using the protocol for B cell supernatant screen. The only change was that titrated purified recombinant mAb was added in place of B cell supernatant.

Immunofluorescence Imaging of Anti-Hyr1 and Anti-Whole Cell mAbs Binding to Fungal Cells Indirect immunofluorescence was performed using purified recombinant mAbs. A single Candida colony was used to inoculate 10 ml YPD medium and incubated at 30° C., 200 rpm overnight. Overnight cultures were diluted 1:1333 in milliQ water and then added to a poly-L-lysine coated glass slide (Thermo Scientific, Menzel-Glaser) and incubated for 30 min at room temperature to allow for adherence of yeast cells to the slide. To induce filamentation, cells were incubated in pre-warmed RPMI+10% FCS at 37° C. for 90 min-2 h (this step was omitted for staining of yeast cells), after which they were washed in Dulbecco's Phosphate Buffered Saline (DPBS) and fixed with 4% paraformaldehyde. Cells were washed again and blocked with 1.5% normal goat serum (Life Technologies) before staining with an anti-Candida mAb at 1-10 µg/ml for 1 h at room temperature. After three PBS washes, cells were stained with Alexa Fluor@ 488 goat anti-human IgG antibody (Life Technologies) at a 1:400 dilution and incubated at room temperature for 1 h in the dark. For additional staining of fungal cell wall chitin, Calcofluor White (CFW) was added at 25 µg/ml and cells were incubated for 10 min at room temperature in the dark and washed with DPBS. Slides were left to air dry before adding one drop of Vectashield mounting medium (Vector Labs) and applying a 20 mm×20 mm coverslip to the slide. Cells were imaged in 3D on an UltraVIEW® VoX spinning disk confocal microscope (Nikon, Surrey, UK).

Preparation of Human Monocyte-Derived Macrophages

Human monocyte-derived macrophages were isolated from the blood of healthy volunteers. In brief, the PBMC layer was isolated as described above and was then washed and re-suspended in DMEM medium (Lonza, Slough, UK) supplemented with 200 U/ml penicillin/streptomycin antibiotics (Invitrogen, Paisley, UK) and 2 mM L-glutamine (Invitrogen, Paisley, UK). Serum was separated from blood using standard methods and heat-inactivated at 56° C. for 20 min before use. Monocytes were isolated from PBMCs via positive selection using CD14 microbeads (MACS, Miltenyi Biotec) according to manufacturer's instructions. PBMCs were incubated with MicroBeads conjugated to monoclonal anti-human CD14 antibodies. Cells were then washed and run through an LS column in a magnetic field causing the $CD14^+$ cells to be retained in the column and the unlabelled cells to run through. The $CD14^+$ cells were then eluted and resuspended in supplemented DMEM containing 10% donor-specific serum, for determination of cell count and viability. Monocytes were then plated out at a density of $1.2\times10^5$ cells/well in an 8-well glass based imaging dish (Ibidi, Munich, Germany) and incubated at 37°, 5% $CO_2$ for 7 days. Cells were used in imaging experiments on day 7. Immediately prior to phagocytosis experiments, supplemented DMEM was replaced with pre-warmed supplemented $CO_2$-independent media (Gibco, Invitrogen, Paisley, UK) containing 1 µM LysoTracker Red DND-99 (Invitrogen, Paisley, UK). LysoTracker Red is a fluorescent dye that stains acidic compartments in live cells, enabling tracking of these cells during phagocytosis and phagolysosome maturation.

Preparation of J774.1 Mouse Macrophage Cell Line

J774.1 macrophages (ECACC, HPA, Salisbury, UK) were maintained in tissue culture flasks in DMEM medium (Lonza, Slough, UK) supplemented with 10% (v/v) FCS (Biosera, Ringmer, UK), 200 U/ml penicillin/streptomycin antibiotics (Invitrogen, Paisley, UK) and 2 mM L-glutamine (Invitrogen, Paisley, UK) and incubated at 37° C., 5% $CO_2$. For phagocytosis assays, macrophages were seeded in 300 µl supplemented DMEM at a density of $1\times10^5$ cells/well in an 8-well glass based imaging dish (Ibidi, Munich, Germany) and incubated overnight at 37° C., 5% $CO_2$. Immediately prior to phagocytosis experiments, supplemented DMEM was replaced with 300 µl pre-warmed supplemented $CO_2$-independent media (Gibco, Invitrogen, Paisley, UK) containing 1 µM LysoTracker Red DND-99 (Invitrogen, Paisley, UK).

Preparation of Fluorescein Isothiocyanate (FITC)-Stained C. albicans

C. albicans colonies were grown in YPD medium and incubated at 30'C, 200 rpm overnight. Live C. albicans cells were stained for 10 min at room temperature in the dark with 1 mg/ml FITC (Sigma, Dorset, UK) in 0.05 M carbonate-bicarbonate buffer (pH 9.6) (BDH Chemicals, VWR International, Leicestershire, UK). Following the 10 min incubation, in phagocytosis assays using C. albicans FITC-labelled yeast, the cells were washed three times in 1×PBS to remove any residual FITC and finally re-suspended in 1×PBS or 1×PBS containing purified anti-Candida mAb at 1-50 µg/ml. For assays where pre-germinated C. albicans was to be added to immune cells, cells were washed and re-suspended in supplemented $CO_2$-independent media with or without anti-Candida mAb at 1-50 ag/ml and incubated at 37° C. with gentle shaking for 45 min.

Live Cell Video Microscopy Phagocytosis Assays

Phagocytosis assays were performed using our standard protocol with modifications (42, 43, 54). Following pre-incubation with/without anti-Candida mAb, live FITC-stained wild type C. albicans (Cλ14-Clp10) yeast or hyphal cells were added to LysoTracker Red DND-99-stained J774.1 murine macrophages or human monocyte-derived macrophages in an 8-well glass based imaging dish (Ibidi) at a multiplicity of infection (MOI) of 3. Video microscopy was performed using an UltraVIEW® VoX spinning disk confocal microscope (Nikon, Surrey, UK) in a 37° C. chamber and images were captured at 1 min intervals over a 3 h period. At least three independent experiments were performed for each antibody and at least 2 videos were analysed from each experiment using Volocity 6.3 imaging analysis software (Improvision, PerkinElmer, Coventry, UK). Twenty five macrophages were selected at random from each experiment and analysed individually at 1 min intervals over a 3 h period. Measurements taken included: C. albicans uptake—defined as the number of C. albicans cells taken up by an individual phagocyte over the 3 h period; C. albicans rate of engulfment—defined as the time point at which cell-cell contact was established until the time point at which C. albicans was fully engulfed (a fungal cell was considered to have been fully ingested when its FITC-fluorescent signal was lost, indicating that the fungal cell was now inside the phagocyte and not merely bound to the phagocyte cell surface) and finally Volocity 6.3 imaging analysis software was used to measure the distance travelled, directionality and velocity of macrophages at 1 min intervals during the first hour of the assay which provided a detailed overview of macrophage migration towards C. albicans cells.

Mean values and standard deviations were calculated. One- or two-way ANOVA followed by Bonferroni multiple comparison tests or unpaired, two-tailed t tests were used to determine statistical significance.

Systemic Candidiasis Infection Model

A well-established three-day model of disseminated candidiasis was employed to assess the efficacy of anti-*Candida* mAbs in vivo (44, 52). On day 0, ~$3.2 \times 10^5$ *C. albicans* SC5314 yeast cells were pre-incubated at RT with 7.5 mg/kg purified recombinant anti-*Candida* mAb for 60 min to allow binding of the antibody to the *Candida* cell surface before administration intravenously via the lateral tail vein. Assessment of disease progression was carried out by observation and weighing on successive days from day 0 up to and including day 3, at which point the animals were culled and the kidneys harvested for analysis of fungal burden. Fungal burdens were quantitated by homogenising the organ, and plating out serial dilutions on Sabouraud dextrose agar plates (1% mycological peptone (w/v), 4% glucose (w/v), 2% agar (w/v)) before incubation at 35° C. overnight. Colonies were counted the next day and fungal burden expressed as log CFU per gram of infected organ. An overall disease outcome score devised from the combination of 3-day weight loss and kidney burden data was also generated to assess disease progression.

Enzymatic Modification of *Candida albicans* Cell Wall

For proteinase K treatment, single colonies of *Candida* were inoculated into 10 ml YPD medium and incubated at 30° C., 200 rpm overnight. Cultures were diluted in milliQ water and then adhered on poly-L-lysine coated glass slides. To induce filamentation, cells were incubated in pre-warmed RPMI+10% FCS at 37° C. for 90 min-2 h. Slides were washed with DPBS and cells were treated with 50 μg/ml proteinase K at 37° C. for 1 h. For Endo-H and zymolyase 20T treatments, *C. albicans* overnight yeast cells were washed and resuspended in DPBS. Filamentous cells were induced as above. Cells were washed in DPBS and resuspended in Glycobuffer and Endoglycosidase H (10 U/μl; NEB) or Buffer S and Zymolyase 20T (50 U/g wet cells; MPBIO) at 37° C. for 2 h. Cells were then washed in DPBS and fixed with 4% paraformaldehyde, washed and blocked with 1.5% normal goat serum (Life Technologies) before staining with an anti-*Candida* mAb at 1 μg/ml for 1 h at room temperature. After 3 washes with DPBS, cells were stained with Alexa Fluor® 488 goat anti-human IgG antibody (Life Technologies) at a 1:400 dilution and incubated at room temperature for 1 h prior to imaging in 3D on an UltraVIEW® VoX spinning disk confocal microscope (Nikon, Surrey, UK).

Preparation of Human Monocyte-Derived Macrophages

Human macrophages were derived from monocytes isolated from the blood of healthy volunteers. PBMCs were resuspended in Dulbecco's Modified Eagle's Medium (DMEM) (Lonza, Slough, UK) supplemented with 200 U/ml penicillin/streptomycin antibiotics (Invitrogen, Paisley, UK) and 2 mM L-glutamine (Invitrogen, Paisley, UK). Serum isolated from blood was heat inactivated for 20 min at 56° C. PBMCs were seeded at $6 \times 10^5$ in 300 μl/well supplemented DMEM medium containing 10% autologous human serum, onto an 8-well glass based imaging dish (Ibidi, Munich, Germany) and incubated at 37° C. with 5% $CO_2$ for 1 h 45 min to facilitate monocyte adherence to the glass surface. Floating lymphocytes in the supernatant were aspirated and the same volume of fresh pre-warmed supplemented DMEM containing 10% autologous human serum added to the well. Cells were incubated at 37° C., 5% $CO_2$ for 7 days with media changed on days 3 and 6. Cells were used in imaging experiments on day 7. Supplemented DMEM was replaced with pre-warmed supplemented $CO_2$-independent media containing 1 μM LysoTracker Red DND-99 (Invitrogen) immediately prior to phagocytosis experiments.

Counterimmunoelectrophoresis

Agar gels were prepared (Veronal buffer+0.5% (w/v) purified agar+0.5% (w/v) LSA agarose+0.05% (w/v) sodium azide, pH 8.2) and wells were cut out using a cutter. Into one column of wells, 10 μl of neat anti-*Candida* mAb was added. The same volume of antigen (crude *C. albicans* yeast or hyphal preparation (following glass bead disruption of cells and 1 min centrifugation at 13000 rpm to generate disrupted cell wall/glass bead slurry and cell supernatant antigenic preparations)) was added to the second column of wells and gels were placed into an electrophoresis tank containing veronal buffer. Gels were oriented so that the antibody wells were lined up alongside the anode and the antigen wells alongside the cathode due to antibody migration towards the cathode via electroendosmosis and antigen migration towards the anode due to lower isoelectric points than the buffer pH. The gels were run at 100V for 90 min before removal and immersion in saline-trisodium citrate overnight. The following day the gels were rinsed with water and covered with moistened filter paper and left to dry in an oven for 2 h. Once dried, the filter paper was moistened and removed and the gels put back into the oven for a further 15 min to dry completely. Gels were then immersed in Buffalo black solution (0.05% (v/v) Buffalo black, 50% (v/v) distilled water, 40% (v/v) methylated spirit, 10% (v/v) acetic acid) for 10 min before destaining in destaining solution (45% (v/v) industrial methylated spirits, 10% (v/v) acetic acid, 45% (v/v) distilled water) for 10 min. Gels were then dried and examined for the formation of precipitin lines. The results are shown in FIG. 17.

High-Pressure Freezing (HPF) of Samples for Immunogold Labelling of *C. albicans* Cells with Anti-*Candida* mAbs for Transmission Electron Microscopy (TEM).

*C. albicans* yeast and hyphal cell samples were prepared by high-pressure freezing using an EMPACT2 high-pressure freezer and rapid transport system (Leica Microsystems Ltd., Milton Keynes, United Kingdom). Using a Leica EMAFS2, cells were freeze-substituted in substitution reagent (1% (w/v) OsO4 in acetone) before embedding in Spurr resin and polymerizing at 60° C. for 48 h. A Diatome diamond knife on a Leica UC6 ultramicrotome was used to cut ultrathin sections which were then mounted onto nickel grids. Sections on nickel grids were blocked in blocking buffer (PBS+1% (w/v) BSA and 0.5% (v/v) Tween20) for 20 min before incubation in incubation buffer (PBS+0.1% (w/v) BSA) for 5 min×3. Sections were then incubated with anti-*Candida* mAb (5 μg/ml) for 90 min before incubation in incubation buffer for 5 min a total of 6 times. mAb binding was detected by incubation with Protein A gold 10 nm conjugate (Aurion) (diluted 1:40 in incubation buffer) for 60 min before another six 5 min washes in incubation buffer followed by three 5 min washes in PBS and three 5 min washes in water. Sections were then stained with uranyl acetate for 1 min before three 2 min washes in water and then left to dry. TEM images were taken using a JEM-1400 Plus using an AMT UltraVUE camera. The results are shown in FIG. 18.

TABLE S1

Clinical isolates and strains

| Strain name | Genotype | Reference |
|---|---|---|
| CAI4 + Clp10 (NGY152) | ura3Δ::λimm434/ura3Δ::λimm434 RPS1/rps1::URA3 | Brand et al. 2004 |
| hyr1Δ | hyr1Δ::hisG/hyr1Δ:hisG-URA-3-hisG | Bailey et al. 1996 |
| hyr1Δ + HYR1 | hyr1::hisG/hyr1::hisG/RPS1/rps1::HYR1 | Belmonte (unpublished) |
| tup1Δ | tup1Δ::hisG/tup1Δ::hisG-URA3-hisG | Fonzi & Irwin 1993 |
| C. albicans SC5314 | Clinical isolate | Gillum et al. 1984 |
| C. glabrata SCS71182B | Clinical isolate | Odds et al. 2007 |
| C. tropicalis AM2005/0546 | Clinical isolate | Clinical isolate from Aberdeen |
| C. lusitaniae SCS211362H | Clinical isolate | Odds et al. 2007 |
| C. krusei SCS71987M | Clinical isolate | Odds et al. 2007 |
| C. parapsilosis ATCC22019 | Clinical isolate | Rudek 1978 |
| C. dubliniensis CD36 | Clinical isolate | Moran et al. 1998 |
| A. fumigatus V05-27 | Clinical isolate | Netea et al. 2003 |
| C. auris CBS 10913T | Clinical isolate | Satoh et al. 2009 |
| C. haemulonii CBS 5149T | Clinical isolate | Khan et al. 2007 |
| C. neoformans KN99α | H99 mating type α | Nielsen et al. 2003 |
| C. gattii R265 | Clinical isolate | Fyfe et al. 2002 |
| P. carinii M167-6 | Isolated from rat lung tissue | — |
| M. dermatis CBS 9169 | CBS | Sugita et al. 2002 |
| M. circinefioides CBS 277.49 | CBS | Li et al. 2011 |

TABLE S2

Recombinant Hyr1 protein amino acid sequence. The leader sequence is underlined and the 6xHis tag is in italics, and is followed by the linker 'G'. Hyr1 protein amino acids 63-350 make up the remainder of the sequence.

| Recombinant protein antigen name | Amino acid sequence (amino acids 63-350) | SEQ ID NO: |
|---|---|---|
| Recombinant Hyr1 N-terminus fragment | METDTLLLWVLLLWVPGSTGGSG*HHHHHH*GEVEKGASLFIKSDNGPVLALNVALSTLVRPVINNGVISLNSKSSTSFSNFDIGGSSFTNNGEIYLASSGLVKSTAYLYAREWTNNGLIVAYQNQKAAGNIAFGTAYQTITNNGQICLRHQDFVPATKIKGTGCVTADEDTWIKLGNTILSVEPTHNFYLKDSKSSLIVHAVSSNQTFTVHGFGNGNKLGLTLPLTGNRDHFRFEYYPDTGILQLRAAALPQYFKIGKGYDSKLFRIVNSRGLKNAVTYDGPVPNNEIPAVCLIPCTNGPSAPESESDLNTPTTSSIGT | 1 |

TABLE S3

Purified recombinant human IgG1 mAbs generated using the single B cell technology.

| Antibody | Yield (mg) | Target |
|---|---|---|
| AB-120 | 12 | Hyr1 protein |
| AB-121 | 28.5 | Hyr1 protein |
| AB-122 | 67.9 | Hyr1 protein |
| AB-123 | 67.3 | Hyr1 protein |
| AB-124 | 38.9 | Hyr1 protein |
| AB-118 | 7.5 | C. albicans 'whole cell' |
| AB-119 | 13.5 | C. albicans 'whole cell' |
| AB-126 | 60.9 | C. albicans 'whole cell' |
| AB-127 | 24.5 | C. albicans 'whole cell' |
| AB-129 | 2.3 | C. albicans 'whole cell' |
| AB-130 | 1.1 | C. albicans 'whole cell' |
| AB-131 | 24.1 | C. albicans 'whole cell' |
| AB-132 | 9.3 | C. albicans 'whole cell' |
| AB-133 | 19 | C. albicans 'whole cell' |
| AB-134 | 7.7 | C. albicans 'whole cell' |
| AB-135 | 16.5 | C. albicans 'whole cell' |
| AB-139 | 12.2 | C. albicans 'whole cell' |
| AB-140 | 19.5 | C. albicans 'whole cell' |

TABLE VH

| AB name | | VH FW1 | VH CDR1 | VH FW2 | VH CDR2 | VH FW3 | VH CDR3 | VH FW4 | SEQ ID NO: |
|---|---|---|---|---|---|---|---|---|---|
| 06-AB-119 | VH3 | QVTLKESGGGLVQPGGSLRLSCVASGFTF | RTYWMH | WVRQDPGKGLVWVS | RLDEVGRLTSYADSVNG | RFTISRDNAKNILYLQMNSLRAEDTGVYYCAR | DLSGSADY | WGQGTLVTVSS | 2 |
| 06-AB-118 | VH3 | EVQLVESGGGLVQPGGSLRLSCSASQFIL | SNYWVH | WVRQVPGEGLVWVS | RINEDGSVTSYADSVKG | RFTISRDNAKNTLYLQMNSLRVDDTAVYYCVR | DLCGERDD | WGQGTLVSVSS | 3 |
| 06-AB-120 | VH3 | EVQLVQSGGGLVQPGGSLGLSCAASGFIF | TSYAMT | WVRQAPGKGLEWVS | VITGNVGTSYYADSVKG | RFTISRDNSKKTVSLQMNSLRAEDTAIYYCVK | TRYDFSSGYYFDD | WGQGTLVSVSS | 4 |

TABLE VH-continued

| AB name | | VH FW1 | VH CDR1 | VH FW2 | VH CDR2 | VH FW3 | VH CDR3 | VH FW4 | SEQ ID NO: |
|---|---|---|---|---|---|---|---|---|---|
| 06-AB-121 | VH3 | EVQLVESGGTLVQPGGSLRLSCAASGFTF | SDYWMN | WVRQAPGKGLEWVA | NIKQDGSEKYYVDSLRG | RVTISRDNAQNSVFLQMHSLSVEDTAVYYCAR | DGYTFGPATTELDH | WGRGTLVSVSS | 5 |
| 06-AB-122 | VH3 | EVQLVQSGGGLAQPPGRSLRLSCAASGFGF | DDFAMH | WVRQPPGKGLEWVS | GLIVVNGGSIDYAGSVRG | RFTISRDNAKNSLFLQMNSLRAEDTALYYCAK | GLSGGTMAPFDI | WGQGTMVSVSS | 6 |
| 06-AB-123 | VH3 | EVQLLESGGGVVQPGRSLRLSCAASGFTF | SNYGMH | WVRQAPGKGLEWVA | VVWFDGSYKYYTDSVKG | RFTISRDNSKSTLYLQMNSLRAEDTAVYYCVS | PIMTSAFDI | WGPGTMVSVSS | 7 |
| 06-AB-124 | VH3 | EVQLVESGGGVVQPGRSLRLSCAASGFTF | SNYGMH | WVRQAPGKGLEWVA | VVWLDGSYKYYTGSVKG | RFTISRDNSKSTLYLQMNSLRAEDTAAYYCVS | PIMTSAFDI | WGPGTMVTVSS | 8 |
| 06-AB-126 | VH3 | EVQLVESGGGLAQPGGSLRLSCEASGFHL | AGNAMA | WVRQAPGKGLEWVA | AIGGSDDRTDYADSVKG | RFTISRDKSKNTLSLQMNSLRVEDTAVYYCAK | DIWRWAFDY | WGQGTLVSVSS | 9 |
| 06-AB-127 | VH3 | EVQLVESGGGLVNPGGSLRLSCAASGFTF | SNYAMN | WVRQAPGKGLEWVS | SISRSGDYIYYADSLKG | RSTISRDNAKNSLFLQMNSLRAEDSAVYYCAR | DWGRLGYCSSNNCPDAFDV | WGQGTRVSVSS | 10 |
| 06-AB-129 | VH3 | QVQLVESGGGLVQPGGSLRLSCSASQFIL | SNYWVH | WVRQVPGEGLVWVS | RINEDGSVTSYADSVKG | RFTISRDNAKNTLYLQMNSLRVDDTAVYYCVR | DLCGERDD | WGQGTLVTVSS | 11 |
| 06-AB-130 | VH3 | QLQLQESGGGLVQPGGSLRLSCSASQFIL | SNYWVH | WVRQVPGEGLVWVS | RINEDGSVTSYADSVKG | RFTISRDNAKNTLYLQMNSLRVDDTAVYYCVR | DLCWERDD | WGQGTLVSVSS | 12 |
| 06-AB-131 | VH3 | QVQLVQSGGGVVQPGGSLRLSCAASPFTF | KISILH | WVRQAPGKGLEWVS | AMSYDGFSKYYADSVKG | RLTISRDSSTNTLYLEMNSLRFEDTALYFCAR | EAYTSGRAGCFNP | WGQGVLVSVSS | 13 |
| 06-AB-132 | VH3 | QVLKESGGGVVQPGGSLRLSCAASPFTF | ETSILH | WVRQAPGKGLEWVS | AMSYDGFSKYYADSVKG | RLTISRDSSTNTLYLEMNSLRFEDTALYFCAR | EAYTSGRAGCFDP | WGQGVLVSVSS | 14 |
| 06-AB-133 | VH3 | EVQLVESGGGLVQPGGSLRVSCAASGFTL | NTYWMH | WVRQAPGKGLVWVS | RINEDGTTISYADSVRG | RFTISRDNAENTLYLQMHSLRAEDTGVYYCAR | DFTGPFDS | WGQGTLVSVSS | 15 |
| 06-AB-134 | VH3 | QLQLQESGGGLVQPGGSLRLSCVVSGFTF | SSHAMS | WVRQAPGKGLEWVS | SISISGGDTFYADSVRG | RFTIFRDNSKNTVYLQMNSLRAEDTAVYYCAT | ETSPNDY | WGQGTLVSVSS | 16 |
| 06-AB-135 | VH3 | EVQLVETGGGLVQPGGSLRLSCVVSGFTF | SSHAMS | WVRQAPGKGLEWVS | SISISGGDTFYADSVRG | RFTIFRDNSKNTVYLQMNSLRAEDTAVYYCAT | ETSPNDY | WGQGTLVTVSS | 17 |
| 06-AB-139 | VH3 | EVQLVESGGGLVQPGGSLRVSCAASGFTL | NTYWMH | WVRQAPGKGLVWVS | RINEDGTTISYADSVRG | RFTISRDNAENTLYLQMHSLRAEDTGVYYCAR | DFTGPFDS | WGQGTLVSVSS | 18 |
| 06-AB-140 | VH3 | EVQLVESGGGLVQPGGSLRVSCAASGFTL | NTYWMH | WVRQAPGKGLVWVS | RINEDGTTISYADSVRG | RFTISRDNAENTLYLQMHSLRAEDTGVYYCAR | DFTGPFDS | WGQGTLVSVSS | 19 |

TABLE VL

| AB name | | VL FW1 | VL CDR1 | VL FW2 | VL CDR2 | VL FW3 | VL CDR3 | VL FW4 | SEQ ID NO: |
|---|---|---|---|---|---|---|---|---|---|
| 06-AB-119 | VK2 | DVVLTQSPLFLPVTPGEPASISC | RSSQSLLHSRGHTSLH | WYLQKPGQSPHLLIY | SVFNRAS | GVPDRFSGSGSGTDFTLKISRVEAEDVGVYYC | MQALEPPYT | FGQGTKLEIK | 20 |
| 06-AB-118 | VK2 | DIVMTQSPLSLPVTPGEAASISC | RSSQSLLHRNGKTFFA | WYLQKPGQSPQILIY | LGSNRAS | GVPDRFSGSGSGTDFTLKISRVEAEDVGIYYC | MQGLQTPYT | FGQGTKLEIK | 21 |

TABLE VL-continued

| AB name | | VL FW1 | VL CDR1 | VL FW2 | VL CDR2 | VL FW3 | VL CDR3 | VL FW4 | SEQ ID NO: |
|---|---|---|---|---|---|---|---|---|---|
| 06-AB-120 | VK2 | DIVMTQSPSSVSASVGDKVTITC | RASQGISRWLA | WYQQKPGEAPELLIY | AASSLOS | GVPSRFSGSGSGTDFTLTISSLQPEDFATYYC | QQANSFPIT | FGQGTRLQIK | 22 |
| 06-AB-121 | VL3 | QLVLTQPPSVSVSPGQTASITC | SGDELRNKYTS | WYQQKSGQSPVLVIY | QDNNRPS | GIPERFSGSQSGDTATLTISGTQAVDEADYYC | QAWVSQTLV | FGGGTKLTVL | 23 |
| 06-AB-122 | VL3 | QAGLTQPPSVSVAPGQTATIPC | GGNNIGSKHVH | WYQQKPGQAPVAVVY | DDSDRPS | GVPERFSGSNSGNTATLTISSVEAGDEADYYC | QVWDRSSDHFWL | FGGGTRLTVL | 24 |
| 06-AB-123 | VL2 | QLVLTQPPSASGSPGQSVTISC | TGTSSDVGGSNFVS | WYQHHPGKAPKLMIY | EVSQRPS | GVPDRFSGSKSGNTASLTVSGLQADDEADYYC | SSYAGSVVL | FGGGTKLTVL | 25 |
| 06-AB-124 | VL2 | QLVLTQPPSASGSPGQSVTISC | TGTSSDVGGSNFVS | WYQHHPGKAPKLMIY | EVSQRPS | GVPDRFSGSKSGNTASLTVSGLQADDEADYYC | SSYAGSVVL | FGGGTKLTVL | 26 |
| 06-AB-126 | VK3 | DIVMTQSPATLSLSPGERATLSC | WASQYINTYVN | WYQHKPGQAPRLLIY | DASKRAT | GIPARFSGSGSGTDFTLTISSLEPEDFAVYYC | QQGSNWPLT | FGQGTRLEIK | 27 |
| 06-AB-127 | VK1 | EIVMTQSPSFVSASVGDRVTITC | RASQDISNWLV | WYQQKPGAPKLLIY | ASSNLOS | GVPSRFSGSGSGTDFALTIISLQPEDFATYYC | QQENSFPYT | FGQGTKLEIK | 28 |
| 06-AB-129 | VK2 | VIWMTQSPLSLPVTPGEAASISC | RSSQSLLHRNGRTFFA | WYLQKPGQSPQILIY | LGSNRAF | GVPDRFSGSGSGTDFTLKISRVEAEDVGIYYC | MQGLQTPYT | FGQGTKLEIK | 29 |
| 06-AB-130 | VK2 | VIWMTQSPLSLPVTPGEAASISC | RSSQSLLHRNGRTFFA | WYLQKPGQSPQILIY | LGSNRAF | GVPDRFSGSGSGTDFTLKISRVEAEDVGIYYC | MQGLQTPYT | FGQGTKLEIK | 30 |
| 06-AB-131 | VK1 | DIVMTQTPSTQSASVGDRVTITC | RASQSISIWLA | WYQQKPGKAPKLLIH | DASTLES | GVPSRFSGSGSGTEFTLTISSLQPDDSATYYC | QRYNDYPPT | FGPGTKVEIK | 31 |
| 06-AB-132 | VK1 | EIVMTQSPSTQSASVGDRVTITC | RASQSISIWLA | WYQQKPGKAPKLLIH | DASTLES | GVPSRFSGSGSGTEFTLTISSLQPDDSATYYC | QRYNDYPPT | FGPGTKVEIK | 32 |
| 06-AB-133 | VL1 | QSVLTQPPSVSGTPGQRVTISC | SGSNSNAGRDYVS | WYQQVPGTAPKLLIY | KNNQRPS | GVPDRFSGSKSGTSASLAISGLRSEDDGDYYC | IVWDGSLSGYV | FGTGTKVTVL | 33 |
| 06-AB-134 | VL7 | SYELTQPSSLTVSPGGTVTLTC | GLSSGAVTSGHYPY | WFQQKPGQAPKTLIF | DTSRKHS | WTPARFSGSLLGGKAALTLSGAQPEDDADYYC | LLACNGACV | FGGGTKLTVL | 34 |
| 06-AB-135 | VL7 | SYELTQPSSLTVSPGGTVTLTC | GLSSGAVTSGHYPY | WFQQKPGQAPKTLIF | DTSRKHS | WTPARFSGSLLGGKAALTLSGAQPEDDADYYC | LLACNGACV | FGGGTKLTVL | 35 |
| 06-AB-139 | VL1 | QSVLTQPPSVSGTPGQRVTISC | SGSNSNVGRDYVS | WYQQVPGTAPKLLIY | KNNRRPS | GVPDRFSGSKSGTSASLAISGLRSEDDGDYYC | IVWDGSLSGYV | FGTGTKVTVL | 36 |
| 06-AB-140 | VL1 | QLVLTQPPSVSGTPGQRVTISC | SGSNSNVGRDYVS | WYQQVPGTAPKLLIY | KNNQRPS | GVPDRFSGSKSGTSASLAISGLRSEDDGDYYC | IVWDGSLSGYV | FGTGTKVTVL | 37 |

Antibody Sequences and Seq ID No.s

TABLE A

Antibody AB119

| 06-AB-119 | Sequence | SEQ ID NO: |
|---|---|---|
| VH FW1 | QVTLKESGGGLVQPGGSLRLSCVASGFTF | 38 |
| VH CDR1 | RTYWMH | 39 |
| VH FW2 | WVRQDPGKGLVWVS | 40 |
| VH CDR2 | RLDEVGRLTSYADSVNG | 41 |
| VH FW3 | RFTISRDNAKNILYLQMNSLRAEDTGVYYCAR | 42 |
| VH CDR3 | DLSGSADY | 43 |
| VH FW4 | WGQGTLVTVSS | 44 |
| VL FW1 | DVVLTQSPLFLPVTPGEPASISC | 45 |
| VL CDR1 | RSSQSLLHSRGHTSLH | 46 |
| VL FW2 | WYLQKPGQSPHLLIY | 47 |
| VL CDR2 | SVFNRAS | 48 |
| VL FW3 | GVPDRFSGSGSGTDFTLKISRVEAEDVGVYYC | 49 |

TABLE A-continued

Antibody AB119

| 06-AB-119 | Sequence | SEQ ID NO: |
|---|---|---|
| VL CDR3 | MQALEPPYT | 50 |
| VL FW4 | FGQGTKLEIK | 51 |

TABLE B

Antibody AB118

| 06-AB-118 | Sequence | SEQ ID NO: |
|---|---|---|
| VH FW1 | EVQLVESGGGLVQPGGSLRLSCSASQFIL | 52 |
| VH CDR1 | SNYWVH | 53 |
| VH FW2 | WVRQVPGEGLVWVS | 54 |
| VH CDR2 | RINEDGSVTSYADSVKG | 55 |
| VH FW3 | RFTISRDNAKNTLYLQMNSLRVDDTAVYYCVR | 56 |

TABLE B-continued

Antibody AB118

| 06-AB-118 | Sequence | SEQ ID NO: |
|---|---|---|
| VH CDR3 | DLCGERDD | 57 |
| VH FW4 | WGQGTLVSVSS | 58 |
| VL FW1 | DIVMTQSPLSLPVTPGEAASISC | 59 |
| VL CDR1 | RSSQSLLHRNGKTFFA | 60 |
| VL FW2 | WYLQKPGQSPQILIY | 61 |
| VL CDR2 | LGSNRAS | 62 |
| VL FW3 | GVPDRFSGSGSGTDFTLKISRVEAEDVGIYYC | 63 |
| VL CDR3 | MQGLQTPYT | 64 |
| VL FW4 | FGQGTKLEIK | 65 |

TABLE C

Antibody AB120

| 06-AB-120 | Sequence | SEQ ID NO: |
|---|---|---|
| VH FW1 | EVQLVQSGGGLVQPGGSLGLSCAASGFIF | 66 |
| VH CDR1 | TSYAMT | 67 |
| VH FW2 | WVRQAPGKGLEWVS | 68 |
| VH CDR2 | VITGNVGTSYYADSVKG | 69 |
| VH FW3 | RFTISRDNSKKTVSLQMNSLRAEDTAIYYCVK | 70 |
| VH CDR3 | TRYDFSSGYYFDD | 71 |
| VH FW4 | WGQGTLVSVSS | 72 |
| VL FW1 | DIVMTQSPSSVSASVGDKVTITC | 73 |
| VL CDR1 | RASQGISRWLA | 74 |
| VL FW2 | WYQQKPGEAPELLIY | 75 |
| VL CDR2 | AASSLQS | 76 |
| VL FW3 | GVPSRFSGSGSGTDFTLTISSLQPEDFATYYC | 77 |
| VL CDR3 | QQANSFPIT | 78 |
| VL FW4 | FGQGTRLQIK | 79 |

TABLE D

Antibody AB121

| 06-AB-121 | Sequence | SEQ ID NO: |
|---|---|---|
| VH FW1 | EVQLVESGGTLVQPGGSLRLSCAASGFTF | 80 |
| VH CDR1 | SDYWMN | 81 |
| VH FW2 | WVRQAPGKGLEWVA | 82 |
| VH CDR2 | NIKQDGSEKYYVDSLRG | 83 |
| VH FW3 | RVTISRDNAQNSVFLQMHSLSVEDTAVYYCAR | 84 |
| VH CDR3 | DGYTFGPATTELDH | 85 |
| VH FW4 | WGRGTLVSVSS | 86 |
| VL FW1 | QLVLTQPPSVSVSPGQTASITC | 87 |
| VL CDR1 | SGDELRNKYTS | 88 |
| VL FW2 | WYQQKSGQSPVLVIY | 89 |
| VL CDR2 | QDNNRPS | 90 |
| VL FW3 | GIPERFSGSQSGDTATLTISGTQAVDEADYYC | 91 |
| VL CDR3 | QAWVSQTLV | 92 |
| VL FW4 | FGGGTKLTVL | 93 |

TABLE E

Antibody AB122

| 06-AB-122 | Sequence | SEQ ID NO: |
|---|---|---|
| VH FW1 | EVQLVQSGGGLAQPGRSLRLSCAASGFGF | 94 |
| VH CDR1 | DDFAMH | 95 |
| VH FW2 | WVRQPPKGLEWVS | 96 |
| VH CDR2 | GLTWNGGSIDYAGSVRG | 97 |

TABLE E-continued

Antibody AB122

| 06-AB-122 | Sequence | SEQ ID NO: |
|---|---|---|
| VH FW3 | RFTISRDNAKNSLFLQMNSLRAEDTALYYCAK | 98 |
| VH CDR3 | GLSGGTMAPFDI | 99 |
| VH FW4 | WGQGTMVSVSS | 100 |
| VL FW1 | QAGLTQPPSVSVAPGQTATIPC | 101 |
| VL CDR1 | GGNNIGSKHVH | 102 |
| VL FW2 | WYQQKPGQAPVAVVY | 103 |
| VL CDR2 | DDSDRPS | 104 |
| VL FW3 | GVPERFSGSNSGNTATLTISSVEAGDEADYYC | 105 |
| VL CDR3 | QVWDRSSDHFWL | 106 |
| VL FW4 | FGGGTRLTVL | 107 |

TABLE F

Antibody AB123

| 06-AB-123 | Sequence | SEQ ID NO: |
|---|---|---|
| VH FW1 | EVQLLESGGGVVQPGRSLRLSCAASGFTF | 108 |
| VH CDR1 | SNYGMH | 109 |
| VH FW2 | WVRQAPGKGLEWVA | 110 |
| VH CDR2 | VVWFDGSYKYYTDSVKG | 111 |
| VH FW3 | RFTISRDNSKSTLYLQMNSLRAEDTAVYYCVS | 112 |
| VH CDR3 | PIMTSAFDI | 113 |
| VH FW4 | WGPGTMVSVSS | 114 |
| VL FW1 | QLVLTQPPSASGSPGQSVTISC | 115 |
| VL CDR1 | TGTSSDVGGSNFVS | 116 |
| VL FW2 | WYQHHPGKAPKLMIY | 117 |
| VL CDR2 | EVSQRPS | 118 |
| VL FW3 | GVPDRFSGSKSGNTASLTVSGLQADDEADYYC | 119 |
| VL CDR3 | SSYAGSVVL | 120 |
| VL FW4 | FGGGTKLTVL | 121 |

TABLE G

Antibody AB124

| 06-AB-124 | Sequence | SEQ ID NO: |
|---|---|---|
| VH FW1 | EVQLVESGGGVVQPGRSLRLSCAASGFTF | 122 |
| VH CDR1 | SNYGMH | 123 |
| VH FW2 | WVRQAPGKGLEWVA | 124 |
| VH CDR2 | VVWLDGSYKYYTGSVKG | 125 |
| VH FW3 | RFTISRDNSKSTLYLQMNSLRAEDTAAYYCVS | 126 |
| VH CDR3 | PIMTSAFDI | 127 |
| VH FW4 | WGPGTMVTVSS | 128 |
| VL FW1 | QLVLTQPPSASGSPGQSVTISC | 129 |
| VL CDR1 | TGTSSDVGGSNFVS | 130 |
| VL FW2 | WYQHHPGKAPKLMIY | 131 |
| VL CDR2 | EVSQRPS | 132 |
| VL FW3 | GVPDRFSGSKSGNTASLTVSGLQADDEADYYC | 133 |
| VL CDR3 | SSYAGSVVL | 134 |
| VL FW4 | FGGGTKLTVL | 135 |

TABLE H

Antibody AB126

| 06-AB-126 | Sequence | SEQ ID NO: |
|---|---|---|
| VH FW1 | EVQLVESGGGLAQPGGSLRLSCEASGFHL | 136 |
| VH CDR1 | AGNAMA | 137 |
| VH FW2 | WVRQAPGKGLEWVA | 138 |

TABLE H-continued

Antibody AB126

| 06-AB-126 | Sequence | SEQ ID NO: |
|---|---|---|
| VH CDR2 | AIGGSDDRTDYADSVKG | 139 |
| VH FW3 | RFTISRDKSNTLSLQMNSLRVEDTAVYYCAK | 140 |
| VH CDR3 | DIWRWAFDY | 141 |
| VH FW4 | WGQGTLVSVSS | 142 |
| VL FW1 | DIVMTQSPATLSLSPGERATLSC | 143 |
| VL CDR1 | WASQYINTYVN | 144 |
| VL FW2 | WYQHKPGQAPRLLIY | 145 |
| VL CDR2 | DASKRAT | 146 |
| VL FW3 | GIPARFSGSGSGTDFTLTISSLEPEDFAVYYC | 147 |
| VL CDR3 | QQGSNWPLT | 148 |
| VL FW4 | FGQGTRLEIK | 149 |

TABLE I

Antibody AB127

| 06-AB-127 | Sequence | SEQ ID NO: |
|---|---|---|
| VH FW1 | EVQLVESGGGLVNPGGSLRLSCAASGFTF | 150 |
| VH CDR1 | SNYAMN | 151 |
| VH FW2 | WVRQAPGKGLEWVS | 152 |
| VH CDR2 | SISRSGDYIYYADSLKG | 153 |
| VH FW3 | RSTISRDNAKNSLFLQMNSLRAEDSAVYYCAR | 154 |
| VH CDR3 | DWGRLGYCSSNNCPDAFDV | 155 |
| VH FW4 | WGQGTRVSVSS | 156 |
| VL FW1 | EIVMTQSPSFVSASVGDRVTITC | 157 |
| VL CDR1 | RASQDISNWLV | 158 |
| VL FW2 | WYQQKPGKAPKLLIY | 159 |
| VL CDR2 | ASSNLQS | 160 |
| VL FW3 | GVPSRFSGSGSGTDFALTIISLQPEDFATYYC | 161 |
| VL CDR3 | QQENSFPYT | 162 |
| VL FW4 | FGQGTKLEIK | 163 |

TABLE J

Antibody AB129

| 06-AB-129 | Sequence | SEQ ID NO: |
|---|---|---|
| VH FW1 | QVQLVESGGGLVQPGGSLRLSCSASQFIL | 164 |
| VH CDR1 | SNYWVH | 165 |
| VH FW2 | WVRQVPGEGLVWVS | 166 |
| VH CDR2 | RINEDGSVTSYADSVKG | 167 |
| VH FW3 | RFTISRDNAKNTLYLQMNSLRVDDTAVYYCVR | 168 |
| VH CDR3 | DLCGERDD | 169 |
| VH FW4 | WGQGTLVTVSS | 170 |
| VL FW1 | VIWMTQSPLSLPVTPGEAASISC | 171 |
| VL CDR1 | RSSQSLLHRNGRTFFA | 172 |
| VL FW2 | WYLQKPGQSPQILIY | 173 |
| VL CDR2 | LGSNRAF | 174 |
| VL FW3 | GVPDRFSGSGSGTDFTLKISRVEAEDVGIYYC | 175 |
| VL CDR3 | MQGLQTPYT | 176 |
| VL FW4 | FGQGTKLEIK | 177 |

TABLE K

Antibody AB130

| 06-AB-130 | Sequence | SEQ ID NO: |
|---|---|---|
| VH FW1 | QLQLQESGGGLVQPGGSLRLSCSASQFIL | 178 |
| VH CDR1 | SNYWVH | 179 |

TABLE K-continued

Antibody AB130

| 06-AB-130 | Sequence | SEQ ID NO: |
|---|---|---|
| VH FW2 | WVRQVPGEGLVWVS | 180 |
| VH CDR2 | RINEDGSVTSYADSVKG | 181 |
| VH FW3 | RFTISRDNAKNTLYLQMNSLRVDDTAVYYCVR | 182 |
| VH CDR3 | DLCWERDD | 183 |
| VH FW4 | WGQGTLVSVSS | 184 |
| VL FW1 | VIWMTQSPLSLPVTPGEAASISC | 185 |
| VL CDR1 | RSSQSLLHRNGRTFFA | 186 |
| VL FW2 | WYLQKPGQSPQILIY | 187 |
| VL CDR2 | LGSNRAF | 188 |
| VL FW3 | GVPDRFSGSGSGTDFTLKISRVEAEDVGIYYC | 189 |
| VL CDR3 | MQGLQTPYT | 190 |
| VL FW4 | FGQGTKLEIK | 191 |

TABLE L

Antibody AB131

| 06-AB-131 | Sequence | SEQ ID NO: |
|---|---|---|
| VH FW1 | QVQLVQSGGGVVQPGGSLRLSCAASPFTF | 192 |
| VH CDR1 | KTSILH | 193 |
| VH FW2 | WVRQAPGKGLEWVS | 194 |
| VH CDR2 | AMSYDGFSKYYADSVKG | 195 |
| VH FW3 | RLTISRDSSTNTLYLEMNSLRFEDTALYFCAR | 196 |
| VH CDR3 | EAYTSGRAGCFNP | 197 |
| VH FW4 | WGQGVLVSVSS | 198 |
| VL FW1 | DIVMTQTPSQSASVGDRVTITC | 199 |
| VL CDR1 | RASQSISIWLA | 200 |
| VL FW2 | WYQQKPGKAPKLLIH | 201 |
| VL CDR2 | DASTLES | 202 |
| VL FW3 | GVPSRFSGSGSGTEFTLTISSLQPDDSATYYC | 203 |
| VL CDR3 | QRYNDYPPT | 204 |
| VL FW4 | FGPGTKVEIK | 205 |

TABLE M

Antibody AB132

| 06-AB-132 | Sequence | SEQ ID NO: |
|---|---|---|
| VH FW1 | QVLKESGGGVVQPGGSLRLSCAASPFTF | 206 |
| VH CDR1 | ETSILH | 207 |
| VH FW2 | WVRQAPGKGLEWVS | 208 |
| VH CDR2 | AMSYDGFSKYYADSVKG | 209 |
| VH FW3 | RLTISRDSSTNTLYLEMNSLRFEDTALYFCAR | 210 |
| VH CDR3 | EAYTSGRAGCFDP | 211 |
| VH FW4 | WGQGVLVSVSS | 212 |
| VL FW1 | EIVMTQSPSTQSASVGDRVTITC | 213 |
| VL CDR1 | RASQSISIWLA | 214 |
| VL FW2 | WYQQKPGKAPKLLIH | 215 |
| VL CDR2 | DASTLES | 216 |
| VL FW3 | GVPSRFSGSGSGTEFTLTISSLQPDDSATYYC | 217 |
| VL CDR3 | QRYNDYPPT | 218 |
| VL FW4 | FGPGTKVEIK | 219 |

TABLE N

Antibody AB133

| 06-AB-133 | Sequence | SEQ ID NO: |
|---|---|---|
| VH FW1 | EVQLVESGGGLVQPGGSLRVSCAASGFTL | 220 |
| VH CDR1 | NTYWMH | 221 |
| VH FW2 | WVRQAPGKGLVWVS | 222 |
| VH CDR2 | RINEDGTTISYADSVRG | 223 |
| VH FW3 | RFTISRDNAENTLYLQMHSLRAEDTGVYYCAR | 224 |
| VH CDR3 | DFTGPFDS | 225 |
| VH FW4 | WGQGTLVSVSS | 226 |
| VL FW1 | QSVLTQPPSVSGTPGQRVTISC | 227 |
| VL CDR1 | SGSNSNAGRDYVS | 228 |
| VL FW2 | WYQQVPGTAPKLLIY | 229 |
| VL CDR2 | KNNQRPS | 230 |
| VL FW3 | GVPDRFSGSKSGTSASLAISGLRSEDDGDYYC | 231 |
| VL CDR3 | IVWDGSLSGYV | 232 |
| VL FW4 | FGTGTKVTVL | 233 |

TABLE O

Antibody AB134

| 06-AB-134 | Sequence | SEQ ID NO: |
|---|---|---|
| VH FW1 | QLQLQESGGGLVQPGGSLRLSCVVSGFTF | 234 |
| VH CDR1 | SSHAMS | 235 |
| VH FW2 | WVRQAPGKGLEWVS | 236 |
| VH CDR2 | SISISGGDTFYADSVRG | 237 |
| VH FW3 | RFTIFRDNSKNTVYLQMNSLRAEDTAVYYCAT | 238 |
| VH CDR3 | ETSPNDY | 239 |
| VH FW4 | WGQGTLVSVSS | 240 |
| VL FW1 | SYELTQPSSLTVSPGGTVTLTC | 241 |
| VL CDR1 | GLSSGAVTSGHYPY | 242 |
| VL FW2 | WFQQKPGQAPKTLIF | 243 |
| VL CDR2 | DTSRKHS | 244 |
| VL FW3 | WTPARFSGSLLGGKAALTLSGAQPEDDADYYC | 245 |
| VL CDR3 | LLACNGACV | 246 |
| VL FW4 | FGGGTKLTVL | 247 |

TABLE P

Antibody AB135

| 06-AB-135 | Sequence | SEQ ID NO: |
|---|---|---|
| VH FW1 | EVQLVETGGGLVQPGGSLRLSCVVSGFTF | 248 |
| VH CDR1 | SSHAMS | 249 |
| VH FW2 | WVRQAPGKGLEWVS | 250 |
| VH CDR2 | SISISGGDTFYADSVRG | 251 |
| VH FW3 | RFTIFRDNSKNTVYLQMNSLRAEDTAVYYCAT | 252 |
| VH CDR3 | ETSPNDY | 253 |
| VH FW4 | WGQGTLVTVSS | 254 |
| VL FW1 | SYELTQPSSLTVSPGGTVTLTC | 255 |
| VL CDR1 | GLSSGAVTSGHYPY | 256 |
| VL FW2 | WFQQKPGQAPKTLIF | 257 |
| VL CDR2 | DTSRKHS | 258 |
| VL FW3 | WTPARFSGSLLGGKAALTLSGAQPEDDADYYC | 259 |
| VL CDR3 | LLACNGACV | 260 |
| VL FW4 | FGGGTKLTVL | 261 |

TABLE Q

Antibody AB139

| 06-AB-139 | Sequence | SEQ ID NO: |
|---|---|---|
| VH FW1 | EVQLVESGGGLVQPGGSLRVSCAASGFTL | 262 |
| VH CDR1 | NTYWMH | 263 |
| VH FW2 | WVRQAPGKGLVWVS | 264 |
| VH CDR2 | RINEDGTTISYADSVRG | 265 |
| VH FW3 | RFTISRDNAENTLYLQMHSLRAEDTGVYYCAR | 266 |
| VH CDR3 | DFTGPFDS | 267 |
| VH FW4 | WGQGTLVSVSS | 268 |
| VL FW1 | QSVLTQPPSVSGTPGQRVTISC | 269 |
| VL CDR1 | SGSNSNVGRDYVS | 270 |
| VL FW2 | WYQQVPGTAPKLLIY | 271 |
| VL CDR2 | KNNRRPS | 272 |
| VL FW3 | GVPDRFSGSKSGTSASLAISGLRSEDDGDYYC | 273 |
| VL CDR3 | IVWDGSLSGYV | 274 |
| VL FW4 | FGTGTKVTVL | 275 |

TABLE R

Antibody AB140

| 06-AB-140 | Sequence | SEQ ID NO: |
|---|---|---|
| VH FW1 | EVQLVESGGGLVQPGGSLRVSCAASGFTL | 276 |
| VH CDR1 | NTYWMH | 277 |
| VH FW2 | WVRQAPGKGLVWVS | 278 |
| VH CDR2 | RINEDGTTISYADSVRG | 279 |
| VH FW3 | RFTISRDNAENTLYLQMHSLRAEDTGVYYCAR | 280 |
| VH CDR3 | DFTGPFDS | 281 |
| VH FW4 | WGQGTLVSVSS | 282 |
| VL FW1 | QLVLTQPPSVSGTPGQRVTISC | 283 |
| VL CDR1 | SGSNSNVGRDYVS | 284 |
| VL FW2 | WYQQVPGTAPKLLIY | 285 |
| VL CDR2 | KNNQRPS | 286 |
| VL FW3 | GVPDRFSGSKSGTSASLAISGLRSEDDGDYYC | 287 |
| VL CDR3 | IVWDGSLSGYV | 288 |
| VL FW4 | FGTGTKVTVL | 289 |

TABLE VH-CDR3-mod

| | Light or Heavy CDR3 | SEQ ID NO: | (Variant of SEQ ID NO:) |
|---|---|---|---|
| 06-AB-118.Heavy C101A | DLAGERDD | 290 | 57 |
| 06-AB-118.Heavy C101S | DLSGERDD | 291 | 57 |
| 06-AB-127.HeavyWY | DWGRLGYWSSNNYPDAFDV | 292 | 155 |
| 06-AB-127.HeavyAA | DWGRLGYASSNNAPDAFDV | 293 | 155 |
| 06-AB-131.HeavyW | EAYTSGRAGWFNP | 294 | 197 |
| 06-AB-131.HeavyA | EAYTSGRAGAFNP | 295 | 197 |
| 06-AB-132.HeavyW | EAYTSGRAGWFDP | 296 | 211 |
| 06-AB-132.HeavyA | EAYTSGRAGAFDP | 297 | 211 |
| 06-AB-129.HeavyW | DLWGERDD | 298 | 169 |
| 06-AB-129.HeavyA | DLAGERDD | 299 | 169 |

TABLE VL-CDR3-mod

| | | | |
|---|---|---|---|
| 06-AB-134.LightYW | LLAYNGAWV | 300 | 246 |
| 06-AB-134.LightAA | LLAANGAAV | 301 | 246 |
| 06-AB-135.LightYW | LLAYNGAWV | 302 | 260 |
| 06-AB-135.LightAA | LLAANGAAV | 303 | 260 |

REFERENCES

1. Brown G D. Innate antifungal immunity: The key role of phagocytes. *Annu. Rev. Immuol.* 29, 1-21 (2011).
2. Lockhart S R. Current epidemiology of *Candida* infection. *Clin. Microbiol. Newsl.* 36, 131-136 (2014).
3. Kim J, Sudbery P. *Candida albicans*, a major human fungal pathogen. *J. Microbiol.* 49, 171-177 (2011).
4. Gow N A R, Van De Veerdonk F L, Brown A J P, Netea M G. *Candida albicans* morphogenesis and host defence: Discriminating invasion from colonization. *Nat. Rev. Microbiol.* 10, 112-122 (2012).
5. Ellepola A N B, Morrison C J. Laboratory diagnosis of invasive candidiasis. *J. Microbiol.* 43, 65-84 (2005).
6. Ostrosky-Zeichner L. Invasive mycoses: Diagnostic challenges. *Am. J. Med.* 125, S14-24 (2012).
7. Perfect J R. Fungal diagnosis: How do we do it and can we do better? *Curr. Med. Res. Opin.* 29, 3-11 (2013).
8. Pfaller M A. Antifungal drug resistance: mechanisms, epidemiology, and consequences for treatment. *Am. J. Med.* 125(1 SUPPL.), S3-S13 (2012).
9. Rader C. Chemically programmed antibodies. *Trends. Biotechnol.* 32, 186-97 (2014).
10. Yoon S, Kim Y-, Shim H, Chung J. Current perspectives on therapeutic antibodies. *Biotechnol. Bioprocess Eng.* 15, 709-15 (2010).
11. Carter P J. Introduction to current and future protein therapeutics: a protein engineering perspective. *Exp. Cell Res.* 317, 1261-1269 (2011).
12. Berry J D, Gaudet R G. Antibodies in infectious diseases: polyclonals, monoclonals and niche biotechnology. *New Biotech.* 28, 489-501 (2011).
13. Saylor C, Dadachova E, Casadevall A. Monoclonal antibody-based therapies for microbial diseases. *Vaccine.* 27, G38-46 (2009).
14. Wilson P C, Andrews S F. Tools to therapeutically harness the human antibody response. *Nat. Rev. Immunol.* 12, 709-19 (2012).
15. Casadevall A, Pirofski L A. Immunoglobulins in defense, pathogenesis, and therapy of fungal diseases. *Cell Host Microbe.* 11, 447-56 (2012).
16. Dromer F, Salamero J, Contrepois A, Carbon C, Yeni P. Production, characterization, and antibody specificity of a mouse monoclonal antibody reactive with *cryptococcus neoformans* capsular polysaccharide. *Infect. Immun.* 55, 742-748 (1987).
17. Gigliotti F, Hughes W T. Passive immunoprophylaxis with specific monoclonal antibody confers partial protection against *Pneumocystis carinii* pneumonitis in animal models. *J. Clin. Invest.* 81, 1666-1668 (1988).
18. Brena S, Cabezas-Olcoz J, Moragues M D, Fernandez De Larrinoa I, Domínguez A, Quindós G, et al. Fungicidal monoclonal antibody C7 interferes with iron acquisition in *Candida albicans. Antimicrob. Agents Chemother.* 55, 3156-3163 (2011).
19. Moragues M D, Omaetxebarria M J, Elguezabal N, Sevilla M J, Conti S, Polonelli L, et al. A monoclonal antibody directed against a *Candida albicans* cell wall mannoprotein exerts three anti-*C. albicans* activities. *Infect. Immun.* 71, 5273-5279 (2003).
20. Torosantucci A, Bromuro C, Chiani P, De Bernardis F, Berti F, Galli C, et al. A novel glyco-conjugate vaccine against fungal pathogens. *J. Exp. Med.* 202, 597-606 (2005).
21. Torosantucci A, Chiani P, Bromuro C, De Bernardis F, Palma A S, Liu Y, et al. Protection by anti-3-glucan antibodies is associated with restricted 3-1,3 glucan binding specificity and inhibition of fungal growth and adherence. *PLoS ONE.* 4, e5392 (2009).
22. Xin H, Cutler J E. Vaccine and monoclonal antibody that enhance mouse resistance to candidiasis. *Clin. Vaccine Immunol.* 18, 1656-1667 (2011).
23. Cassone A. Vulvovaginal *Candida albicans* infections: Pathogenesis, immunity and vaccine prospects. BJOG. doi: 10.1111/1471-0528.12994. (2014).
24. Cassone A. Development of vaccines for *Candida albicans*:fighting a skilled transformer. *Nat. Rev. Microbiol.* 11, 884-91 (2013).
25. Bromuro C, Romano M, Chiani P, Berti F, Tontini M, Proietti D, et al. Beta-glucan-CRM197 conjugates as Candidates antifungal vaccines. *Vaccine.* 28, 2615-23 (2010).
26. Schmidt C S, White C J, Ibrahim A S, Filler S G, Fu Y, Yeaman M R, et al. NDV-3, a recombinant alum-adjuvanted vaccine for *Candida* and *Staphylococcus aureus*, is safe and immunogenic in healthy adults. *Vaccine.* 30, 7594-7600 (2012).
27. Han Y, Morrison R P, Cutler J E. A vaccine and monoclonal antibodies that enhance mouse resistance to *Candida albicans* vaginal infection. *Infect. Immun.* 66, 5771-5776 (1998).
28. Ibrahim A S, Luo G, Gebremariam T, Lee H, Schmidt C S, Hennessey J P, et al. NDV-3 protects mice from vulvovaginal candidiasis through T- and B-cell immune response. *Vaccine.* 31, 5549-56 (2013).
29. Luo G, Ibrahim A S, French S W, Edwards Jr. J E, Fu Y. Active and passive immunization with rHyrip-N protects mice against hematogenously disseminated candidiasis. *PLoS ONE.* 6, e25909. (2011).
30. Thornton C, Johnson G, Agrawal S. Detection of invasive pulmonary aspergillosis in haematological malignancy patients by using lateral-flow technology. *J. Vis. Exp.* 61, pii: 3721. doi: 10.3791/3721 (2012).
31. Thornton C R. Development of an immunochromatographic lateral-flow device for rapid serodiagnosis of invasive aspergillosis. *Clin. Vaccine Immunol.* 15, 1095-1105 (2008).
32. Martinez-Jiménez M C, Muñoz P, Guinea J, Valerio M, Alonso R, Escribano P, et al. Potential role of *Candida albicans* germ tube antibody in the diagnosis of deep-seated candidemia. *Med. Mycol.* 52, 270-275 (2014).
33. Jarvis J N, Percival A, Bauman S, Pelfrey J, Meintjes G, Williams G N, et al. Evaluation of a novel point-of-care cryptococcal antigen test on serum, plasma, and urine from patients with HIV-associated cryptococcal meningitis. *Clin. Infect. Dis.* 53, 1019-1023 (2011).
34. Carter P J. Potent antibody therapeutics by design. *Nat. Rev. Immunol.* 6, 343-357 (2006).
35. Tiller T. Single B cell antibody technologies. *N. Biotechnol.* 28, 453-457 (2011).
36. Smith K, Garman L, Wrammert J, Zheng N Y, Capra J D, Ahmed R, et al. Rapid generation of fully human monoclonal antibodies specific to a vaccinating antigen. *Nat. Protoc.* 4, 372-384 (2009).

37. Liao H X, Levesque M C, Nagel A, Dixon A, Zhang R, Walter E, et al. High-throughput isolation of immunoglobulin genes from single human B cells and expression as monoclonal antibodies. *J. Virol. Methods.* 158, 171-179 (2009).
38. Huang J, Doria-Rose N A, Longo N S, Laub L, Lin C-, Turk E, et al. Isolation of human monoclonal antibodies from peripheral blood B cells. *Nat. Protoc.* 8, 1907-1915 (2013).
39. Jiang X, Suzuki H, Hanai Y, Wada F, Hitomi K, Yamane T, et al. A novel strategy for generation of monoclonal antibodies from single B cells using R T-PCR technique and in vitro expression. *Biotechnol. Prog.* 22, 979-88 (2006).
40. Bailey D A, Feldmann P J F, Bovey M, Gow N A R, Brown A J P. The *Candida albicans* HYR1 gene, which is activated in response to hyphal development, belongs to a gene family encoding yeast cell wall proteins. *J. Bacteriol.* 178, 5353-5360 (1996).
41. Luo G, Ibrahim A S, Spellberg B, Nobile C J, Mitchell A P, Fu Y. *Candida albicans* Hyrip confers resistance to neutrophil killing and is a potential vaccine target. *J. Infect. Dis.* 201, 1718-1728 (2010).
42. Lewis L E, Bain J M, Lowes C, Gillespie C, Rudkin F M, Gow N A R, et al. Stage specific assessment of *Candida albicans* phagocytosis by macrophages identifies cell wall composition and morphogenesis as key determinants. *PLoS Pathog.* 8, e1002578 (2012).
43. Rudkin F M, Bain J M, Walls C, Lewis L E, Gow N A R, Erwig L P. Altered dynamics of *Candida albicans* phagocytosis by macrophages and PMNs when both phagocyte subsets are present. *mBio.* 4, e00810-13. doi: 10.1128/mBio.00810-13 (2013).
44. MacCallum D M, Coste A, Ischer F, Jacobsen M D, Odds F C, Sanglard D. Genetic dissection of azole resistance mechanisms in *Candida albicans* and their validation in a mouse model of disseminated infection. *Antimicrob. Agents Chemother.* 54, 1476-1483 (2010).
45. Chames P, Van Regenmortel M, Weiss E, Baty D. Therapeutic antibodies: successes, limitations and hopes for the future. *Br. J. Pharmacol.* 157, 220-233 (2009).
46. Beyda N D, Regen S, Lewis R E, Garey K W. Immunomodulatory agents as adjunctive therapy for the treatment of resistant *Candida* species. *Curr. Fungal Infect. Rep.* 7, 119-125 (2013).
47. Overdijk M B, Verploegen S, Buijsse A O, Vink T, Leusen J H W, Bleeker W K, et al. Crosstalk between human IgG isotypes and murine effector cells. *J. Immunol.* 189, 3430-3438 (2012).
48. Reichert J M. Marketed therapeutic antibodies compendium. *mAbs.* 4, 413-415 (2012).
49. Brown G D, Denning D W, Gow N A R, Levitz S M, Netea M G, White T C. Hidden killers: human fungal infections. *Sci. Transl. Med.* 4, 165rv13 (2012).
50. d'Enfert C, Goyard S, Rodriguez-Arnaveilhe S, Frangeul L, Jones L, Tekaia F, et al. CandidaDB: A genome database for *Candida albicans* pathogenomics. *Nucleic Acids Res.* 33(DATABASE ISS.), D353-357 (2005).
51. Yapar N. Epidemiology and risk factors for invasive candidiasis. *Ther. Clin. Risk Manag.* 10, 95-105 (2014).
52. MacCallum D M. Hosting infection: experimental models to assay *Candida* virulence. *Int. J. Microbiol.* 2012, 363764 (2012).
53. Durocher Y, Perret S, Kamen A. High-level and high-throughput recombinant protein production by transient transfection of suspension-growing human 293-EBNA1 cells. *Nucleic Acids Res.* 30, e9 (2002).
54. McKenzie C G J, Koser U, Lewis L E, Bain J M, Mora-Montes H M, Barker R N, et al. Contribution of *Candida albicans* cell wall components to recognition by and escape from murine macrophages. *Infect. Immun.* 78, 1650-1658 (2010).

ADDITIONAL REFERENCES FOR TABLE S1

Brand A, MacCallum D M, Brown A J, Gow N A, Odds F C. Ectopic expression of URA3 can influence the virulence phenotypes and proteome of *Candida albicans* but can be overcome by targeted reintegration of URA3 at the RPS10 locus. *Eukaryot Cell* 3: 900-909. doi: 10.1128/ec.3.4.900-909.2004 (2004).

Bailey D A, Feldmann P J F, Bovey M, Gow N A R, Brown A J P. The *Candida albicans* HYR1 gene, which is activated in response to hyphal development, belongs to a gene family encoding yeast cell wall proteins. *J. Bacteriol.* 178, 5353-5360 (1996).

Fonzi, W. A., Irwin M. Y. Isogenic strain construction and gene mapping in *Candida albicans*. *Genetics* 134, 717-728 (1993).

Gillum A M, Tsay E Y, Kirsch D R. Isolation of the *Candida albicans* gene for orotidine-5'-phosphate decarboxylase by complementation of *S. cerevisiae* ura3 and *E. coli* pyrF mutations. *Mol Gen Genet.* 198:179-8 (1984).

Odds F C, Hanson M F, Davidson A D, Jacobsen M D, Wright P, Whyte J A, Gow N A, Jones B L. One year prospective survey of *Candida* bloodstream infections in Scotland. *J Med Microbiol.* 56: 1066-1075 (2007).

Rudek W. Esterase activity in *Candida* species. *J. Clin. Microbiol.* 8: 756-759 (1978). Moran G P, Sanglard D, Donnelly S M, Shanley D B, Sullivan D J, Coleman D C. Identification and expression of multidrug transporters responsible for fluconazole resistance in *Candida dubliniensis*. *Antimicrob. Agents Chemother.* 42:1819-1830 (1998).

Moran, G. P., Sanglard, D., Donnelly S. M., Shanley D. B., Sullivan D. J., Coleman D. C. Identification and expression of multidrug transporters responsible for fluconazole resistance in *Candida dubliniensis*. *Antimicrob. Agents Chemother.* 42, 1819-1830 (1998).

Netea, M. G. et al. *Aspergillus fumigatus* evades immune recognition during germination through loss of toll-like receptor-4-mediated signal transduction. *J. Infect. Dis.* 188, 320-326 (2003).

Satoh, K., Makimura K., Hasumi Y., Nishiyama Y., Uchida K., Yamaguchi H. *Candida auris* sp. nov., a novel ascomycetous yeast isolated from the external ear canal of an inpatient in a Japanese hospital. *Microbiol. Immunol.* 53, 41-44 (2009).

Khan, Z. U. et al. Outbreak of fungemia among neonates caused by *Candida haemulonii* resistant to amphotericin B, itraconazole, and fluconazole. *J. Clin. Microbiol.* 45, 2025-2027 (2007).

Nielsen, K., Cox G. M., Wang P., Toffaletti D. L., Perfect J. R., Heitman J. Sexual cycle of *Cryptococcus neoformans* var. grubii and Virulence of congenic a and a isolates. *Infect. Immun.* 71, 4831-4841 (2003).

Fyfe, M., W. Black and M. Romney. Unprecedented outbreak of *Cryptococcus neoformans* var. gattil infections in British Columbia, Canada. Abstracts of the 5th International Conference on *Cryptococcus* and Cryptococcosis (2002).

Sugita, T. et al. New yeast species, *Malassezia* dermatis, isolated from patients with atopic dermatitis. *J. Clin. Microbiol.* 40, 1363-1367 (2002).

Li, C. H. et al. Sporangiospore size dimorphism is linked to virulence of *Mucor circinelloides*. *PLoS Pathogens* 7, e1002086 (2011).

The invention claimed is:

1. A method comprising contacting a *Candida* cell with an anti-*Candida* antibody molecule, wherein the anti-*Candida* antibody molecule is a whole antibody comprising a VH domain comprising:
   (i) a HCDR1 having the amino acid sequence of SEQ ID NO: 39;
   (ii) a HCDR2 having the amino acid sequence of SEQ ID NO: 41; and
   (iii) a HCDR3 having the amino acid sequence of SEQ ID NO: 43;
   and a VL domain comprising:
   (i) a LCDR1 having the amino acid sequence of SEQ ID NO: 46;
   (ii) a LCDR2 having the amino acid sequence of SEQ ID NO: 48; and
   (iii) a LCDR3 having the amino acid sequence of SEQ ID NO: 50, wherein the binding of the anti-*Candida* antibody to the *Candida* cell
   (i) opsonises, or increases the rate of opsonisation of the *Candida* cell; or
   (ii) increases the rate of macrophage engulfment of the *Candida* cell; or
   (iii]) increases the rate of macrophage attraction to the *Candida* cell.

2. A method of treatment of a *Candida* infection comprising administering an anti-*Candida* antibody molecule to an individual in need thereof, wherein the antibody molecule is a whole antibody comprising a VH domain comprising:
   (i) a HCDR1 having the amino acid sequence of SEQ ID NO: 39;
   (ii) a HCDR2 having the amino acid sequence of SEQ ID NO: 41; and
   (iii) a HCDR3 having the amino acid sequence of SEQ ID NO: 43;
   and a VL domain comprising:
   (i) a LCDR1 having the amino acid sequence of SEQ ID NO: 46;
   (ii) a LCDR2 having the amino acid sequence of SEQ ID NO: 48; and
   (iii) a LCDR3 having the amino acid sequence of SEQ ID NO: 50.

3. A method according to claim 2 wherein the fungal infection is caused by *C. albicans* and wherein the infection is in a hyphal or yeast phase.

4. A method according to claim 2, wherein the treatment further comprises administering an additional antifungal agent.

5. A method for detecting the presence or absence of a fungus which is a *Candida* spp, the method comprising
   (i) contacting a sample suspected of containing the fungus with an anti-*Candida* antibody molecule, and
   (ii) determining whether the anti-*Candida* antibody molecule binds to the sample, binding of the antibody molecule to the sample indicates the presence of the fungus, and wherein the anti-*Candida* antibody molecule comprises a VH domain comprising:
   (i) a HCDR1 having the amino acid sequence of SEQ ID NO: 39;
   (ii) a HCDR2 having the amino acid sequence of SEQ ID NO: 41; and
   (iii) a HCDR3 having the amino acid sequence of SEQ ID NO: 43;
   and a VL domain comprising
   (i) a LCDR1 having the amino acid sequence of SEQ ID NO: 46;
   (ii) a LCDR2 having the amino acid sequence of SEQ ID NO: 48; and
   (iii) a LCDR3 having the amino acid sequence of SEQ ID NO: 50.

6. A lateral flow device (LFD) for detecting the presence of an analyte which is a fungal pathogen in a sample fluid, wherein said LFD comprises:
   (i) a housing, and
   ii) at least one flow path leading from a sample well to a viewing window, wherein said flow path comprises one or more carriers along which the sample fluid is capable of flowing by capillary action, and wherein the one or more carriers comprise an analyte-detecting means;
      wherein the presence of analyte produces a line in the viewing window which indicates the presence of the fungal pathogen,
   wherein the fungal pathogen is a *Candida* spp. and the at least one analyte-detecting means is an anti-*Candida* antibody molecule comprising a VH domain comprising:
   (i) a HCDR1 having the amino acid sequence of SEQ ID NO: 39;
   (ii) a HCDR2 having the amino acid sequence of SEQ ID NO: 41; and
   (iii) a HCDR3 having the amino acid sequence of SEQ ID NO: 43;
   and a VL domain comprising:
   (i) a LCDR1 having the amino acid sequence of SEQ ID NO: 46;
   (ii) a LCDR2 having the amino acid sequence of SEQ ID NO: 48; and
   (iii) a LCDR3 having the amino acid sequence of SEQ ID NO: 50.

7. The device as claimed in claim 6, wherein the one or more carriers comprises a plurality of analyte-detecting means, each analyte-detecting means is specific for a different fungal pathogen, and wherein the plurality of analyte-detecting means are capable of distinguishing between multiple fungal pathogens.

8. The device as claimed in claim 7 wherein the multiple fungal pathogens comprise *C. albicans*, and at least one fungus selected from the group consisting of *Aspergillus fumigatus, Cryptococcus neoformans, Pneumocystis jirovecii*, a zygomycete fungus, and a skin dermatophytic fungus.

9. The method according to claim 2, wherein the VH domain comprises at least one sequence selected from the following:
   (i) a FW1 having the amino acid sequence of SEQ ID NO: 38;
   (ii) a FW2 having the amino acid sequence of SEQ ID NO: 40;
   (iii) a FW3 having the amino acid sequence of SEQ ID NO: 42; and
   (iv) a FW4 having the amino acid sequence of SEQ ID NO: 44.

10. The method according to claim 2, wherein the VL domain comprises at least one sequence selected from the following:
   (i) a FW1 having the amino acid sequence of SEQ ID NO: 45;
   (ii) a FW2 having the amino acid sequence of SEQ ID NO: 47;
   (iii) a FW3 having the amino acid sequence of SEQ ID NO: 49; and
   (iv) a FW4 having the amino acid sequence of SEQ ID NO: 51.

11. The method according to claim 2, wherein the VH domain and the VL domain have amino acid sequences of SEQ ID NO: 2 and SEQ ID NO: 20, respectively.

12. The method of claim 2, wherein the fungal infection is caused by a species selected from the group consisting of *C. albicans, C. dubliniensis, C. tropicalis, C. parapsilosis* and *C. lusitaniae*.

13. The method of claim 4, wherein the additional anti-fungal agent is an azole, a polyene or an echinocandin.

14. A method comprising contacting a *Candida* cell with an anti-*Candida* antibody molecule, wherein the anti-*Candida* antibody molecule comprises a VH domain comprising:
   (i) a HCDR1 having the amino acid sequence of SEQ ID NO: 39;
   (ii) a HCDR2 having the amino acid sequence of SEQ ID NO: 41; and
   (iii) a HCDR3 having the amino acid sequence of SEQ ID NO: 43;

and a VL domain comprising:
   (i) a LCDR1 having the amino acid sequence of SEQ ID NO: 46;
   (ii) a LCDR2 having the amino acid sequence of SEQ ID NO: 48; and
   (iii) a LCDR3 having the amino acid sequence of SEQ ID NO: 50, wherein the anti-*Candida* antibody molecule binds to the *Candida* cell or a hyphae of the cell, and wherein the method further comprises detecting the bound anti-*Candida* antibody to identify or detect the *Candida* cell or a hyphae of the *Candida* cell.

* * * * *

SEQUENCE LISTING

<160> NUMBER OF SEQ ID NOS: 303

<210> SEQ ID NO 1
<211> LENGTH: 318
<212> TYPE: PRT
<213> ORGANISM: Artificial sequence
<220> FEATURE:
<223> OTHER INFORMATION: Recombinant Hyr1 protein amino acid sequence

<400> SEQUENCE: 1

Met Glu Thr Asp Thr Leu Leu Leu Trp Val Leu Leu Trp Val Pro
1               5                   10                  15

Gly Ser Thr Gly Gly Ser Gly His His His His His Gly Glu Val
                20              25                  30

Glu Lys Gly Ala Ser Leu Phe Ile Lys Ser Asp Asn Gly Pro Val Leu
            35                  40                  45

Ala Leu Asn Val Ala Leu Ser Thr Leu Val Arg Pro Val Ile Asn Asn
        50                  55                  60

Gly Val Ile Ser Leu Asn Ser Lys Ser Ser Thr Ser Phe Ser Asn Phe
65                  70                  75                  80

Asp Ile Gly Gly Ser Phe Thr Asn Asn Gly Glu Ile Tyr Leu Ala
                85                  90                  95

Ser Ser Gly Leu Val Lys Ser Thr Ala Tyr Leu Tyr Ala Arg Glu Trp
            100                 105                 110

Thr Asn Asn Gly Leu Ile Val Ala Tyr Gln Asn Gln Lys Ala Ala Gly
        115                 120                 125

Asn Ile Ala Phe Gly Thr Ala Tyr Gln Thr Ile Thr Asn Asn Gly Gln
    130                 135                 140

Ile Cys Leu Arg His Gln Asp Phe Val Pro Ala Thr Lys Ile Lys Gly
145                 150                 155                 160

Thr Gly Cys Val Thr Ala Asp Glu Asp Thr Trp Ile Lys Leu Gly Asn
                165                 170                 175

Thr Ile Leu Ser Val Glu Pro Thr His Asn Phe Tyr Leu Lys Asp Ser
            180                 185                 190

Lys Ser Ser Leu Ile Val His Ala Val Ser Ser Asn Gln Thr Phe Thr
        195                 200                 205

Val His Gly Phe Gly Asn Gly Asn Lys Leu Gly Leu Thr Leu Pro Leu
    210                 215                 220

Thr Gly Asn Arg Asp His Phe Arg Phe Glu Tyr Tyr Pro Asp Thr Gly
225                 230                 235                 240

Ile Leu Gln Leu Arg Ala Ala Ala Leu Pro Gln Tyr Phe Lys Ile Gly
                245                 250                 255

Lys Gly Tyr Asp Ser Lys Leu Phe Arg Ile Val Asn Ser Arg Gly Leu
            260                 265                 270

Lys Asn Ala Val Thr Tyr Asp Gly Pro Val Pro Asn Asn Glu Ile Pro
        275                 280                 285

Ala Val Cys Leu Ile Pro Cys Thr Asn Gly Pro Ser Ala Pro Glu Ser
    290                 295                 300

Glu Ser Asp Leu Asn Thr Pro Thr Thr Ser Ser Ile Gly Thr
305                 310                 315

<210> SEQ ID NO 2
<211> LENGTH: 117
<212> TYPE: PRT
<213> ORGANISM: Homo sapiens

<400> SEQUENCE: 2

```
Gln Val Thr Leu Lys Glu Ser Gly Gly Gly Leu Val Gln Pro Gly Gly
1               5                   10                  15

Ser Leu Arg Leu Ser Cys Val Ala Ser Gly Phe Thr Phe Arg Thr Tyr
            20                  25                  30

Trp Met His Trp Val Arg Gln Asp Pro Gly Lys Gly Leu Val Trp Val
        35                  40                  45

Ser Arg Leu Asp Glu Val Gly Arg Leu Thr Ser Tyr Ala Asp Ser Val
50                  55                  60

Asn Gly Arg Phe Thr Ile Ser Arg Asp Asn Ala Lys Asn Ile Leu Tyr
65                  70                  75                  80

Leu Gln Met Asn Ser Leu Arg Ala Glu Asp Thr Gly Val Tyr Tyr Cys
                85                  90                  95

Ala Arg Asp Leu Ser Gly Ser Ala Asp Tyr Trp Gly Gln Gly Thr Leu
            100                 105                 110

Val Thr Val Ser Ser
            115

<210> SEQ ID NO 3
<211> LENGTH: 117
<212> TYPE: PRT
<213> ORGANISM: Homo sapiens

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ser Ala Ser Gln Phe Ile Leu Ser Asn Tyr
            20                  25                  30

Trp Val His Trp Val Arg Gln Val Pro Gly Glu Gly Leu Val Trp Val
        35                  40                  45

Ser Arg Ile Asn Glu Asp Gly Ser Val Thr Ser Tyr Ala Asp Ser Val
50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Val Asp Asp Thr Ala Val Tyr Tyr Cys
                85                  90                  95

Val Arg Asp Leu Cys Gly Glu Arg Asp Asp Trp Gly Gln Gly Thr Leu
            100                 105                 110

Val Ser Val Ser Ser
            115

<210> SEQ ID NO 4
<211> LENGTH: 122
<212> TYPE: PRT
<213> ORGANISM: Homo sapiens

<400> SEQUENCE: 4

Glu Val Gln Leu Val Gln Ser Gly Gly Gly Leu Val Gln Pro Gly Gly
1               5                   10                  15

Ser Leu Gly Leu Ser Cys Ala Ala Ser Gly Phe Ile Phe Thr Ser Tyr
            20                  25                  30

Ala Met Thr Trp Val Arg Gln Ala Pro Gly Lys Gly Leu Glu Trp Val
        35                  40                  45

Ser Val Ile Thr Gly Asn Val Gly Thr Ser Tyr Tyr Ala Asp Ser Val
50                  55                  60

Lys Gly Arg Phe Thr Ile Ser Arg Asp Asn Ser Lys Lys Thr Val Ser
65                  70                  75                  80
```

```
Leu Gln Met Asn Ser Leu Arg Ala Glu Asp Thr Ala Ile Tyr Tyr Cys
                85                  90                  95

Val Lys Thr Arg Tyr Asp Phe Ser Gly Tyr Tyr Phe Asp Asp Trp
            100                 105                 110

Gly Gln Gly Thr Leu Val Ser Val Ser Ser
        115                 120

<210> SEQ ID NO 5
<211> LENGTH: 123
<212> TYPE: PRT
<213> ORGANISM: Homo sapiens

<400> SEQUENCE: 5

Glu Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Asn Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Leu
    50                  55                  60

Arg Gly Arg Val Thr Ile Ser Arg Asp Asn Ala Gln Asn Ser Val Phe
65                  70                  75                  80

Leu Gln Met His Ser Leu Ser Val Glu Asp Thr Ala Val Tyr Tyr Cys
                85                  90                  95

Ala Arg Asp Gly Tyr Thr Phe Gly Pro Ala Thr Thr Glu Leu Asp His
            100                 105                 110

Trp Gly Arg Gly Thr Leu Val Ser Val Ser Ser
        115                 120

<210> SEQ ID NO 6
<211> LENGTH: 121
<212> TYPE: PRT
<213> ORGANISM: Homo sapiens

<400> SEQUENCE: 6

Glu Val Gln Leu Val Gln Ser Gly Gly Gly Leu Ala Gln Pro Gly Arg
1               5                   10                  15

Ser Leu Arg Leu Ser Cys Ala Ala Ser Gly Phe Gly Phe Asp Asp Phe
            20                  25                  30

Ala Met His Trp Val Arg Gln Pro Pro Gly Lys Gly Leu Glu Trp Val
        35                  40                  45

Ser Gly Leu Thr Trp Asn Gly Gly Ser Ile Asp Tyr Ala Gly Ser Val
    50                  55                  60

Arg Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Leu Tyr Tyr Cys
                85                  90                  95

Ala Lys Gly Leu Ser Gly Gly Thr Met Ala Pro Phe Asp Ile Trp Gly
            100                 105                 110

Gln Gly Thr Met Val Ser Val Ser Ser
        115                 120

<210> SEQ ID NO 7
<211> LENGTH: 118
<212> TYPE: PRT
<213> ORGANISM: Homo sapiens
```

<400> SEQUENCE: 7

```
Glu Val Gln Leu Leu Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Val Trp Phe Asp Gly Ser Tyr Lys Tyr Tyr Thr Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Val Ser Pro Ile Met Thr Ser Ala Phe Asp Ile Trp Gly Pro Gly Thr
            100                 105                 110

Met Val Ser Val Ser Ser
            115
```

<210> SEQ ID NO 8
<211> LENGTH: 118
<212> TYPE: PRT
<213> ORGANISM: Homo sapiens

<400> SEQUENCE: 8

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Val Trp Leu Asp Gly Ser Tyr Lys Tyr Tyr Thr Gly Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Ala Tyr Tyr Cys
                85                  90                  95

Val Ser Pro Ile Met Thr Ser Ala Phe Asp Ile Trp Gly Pro Gly Thr
            100                 105                 110

Met Val Thr Val Ser Ser
            115
```

<210> SEQ ID NO 9
<211> LENGTH: 118
<212> TYPE: PRT
<213> ORGANISM: Homo sapiens

<400> SEQUENCE: 9

```
Glu Val Gln Leu Val Glu Ser Gly Gly Gly Leu Ala Gln Pro Gly Gly
1               5                   10                  15

Ser Leu Arg Leu Ser Cys Glu Ala Ser Gly Phe His Leu Ala Gly Asn
            20                  25                  30

Ala Met Ala Trp Val Arg Gln Ala Pro Gly Lys Gly Leu Glu Trp Val
        35                  40                  45

Ala Ala Ile Gly Gly Ser Asp Asp Arg Thr Asp Tyr Ala Asp Ser Val
    50                  55                  60
```

```
Lys Gly Arg Phe Thr Ile Ser Arg Asp Lys Ser Lys Asn Thr Leu Ser
 65                  70                  75                  80

Leu Gln Met Asn Ser Leu Arg Val Glu Asp Thr Ala Val Tyr Tyr Cys
                 85                  90                  95

Ala Lys Asp Ile Trp Arg Trp Ala Phe Asp Tyr Trp Gly Gln Gly Thr
            100                 105                 110

Leu Val Ser Val Ser Ser
            115

<210> SEQ ID NO 10
<211> LENGTH: 128
<212> TYPE: PRT
<213> ORGANISM: Homo sapiens

<400> SEQUENCE: 10

Glu Val Gln Leu Val Glu Ser Gly Gly Gly Leu Val Asn Pro Gly Gly
 1               5                  10                  15

Ser Leu Arg Leu Ser Cys Ala Ala Ser Gly Phe Thr Phe Ser Asn Tyr
                20                  25                  30

Ala Met Asn Trp Val Arg Gln Ala Pro Gly Lys Gly Leu Glu Trp Val
             35                  40                  45

Ser Ser Ile Ser Arg Ser Gly Asp Tyr Ile Tyr Tyr Ala Asp Ser Leu
 50                  55                  60

Lys Gly Arg Ser Thr Ile Ser Arg Asp Asn Ala Lys Asn Ser Leu Phe
 65                  70                  75                  80

Leu Gln Met Asn Ser Leu Arg Ala Glu Asp Ser Ala Val Tyr Tyr Cys
                 85                  90                  95

Ala Arg Asp Trp Gly Arg Leu Gly Tyr Cys Ser Ser Asn Asn Cys Pro
            100                 105                 110

Asp Ala Phe Asp Val Trp Gly Gln Gly Thr Arg Val Ser Val Ser Ser
            115                 120                 125

<210> SEQ ID NO 11
<211> LENGTH: 117
<212> TYPE: PRT
<213> ORGANISM: Homo sapiens

<400> SEQUENCE: 11

Gln Val Gln Leu Val Glu Ser Gly Gly Gly Leu Val Gln Pro Gly Gly
 1               5                  10                  15

Ser Leu Arg Leu Ser Cys Ser Ala Ser Gln Phe Ile Leu Ser Asn Tyr
                20                  25                  30

Trp Val His Trp Val Arg Gln Val Pro Gly Glu Gly Leu Val Trp Val
             35                  40                  45

Ser Arg Ile Asn Glu Asp Gly Ser Val Thr Ser Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Val Asp Thr Ala Val Tyr Tyr Cys
                 85                  90                  95

Val Arg Asp Leu Cys Gly Glu Arg Asp Asp Trp Gly Gln Gly Thr Leu
            100                 105                 110

Val Thr Val Ser Ser
            115

<210> SEQ ID NO 12
<211> LENGTH: 117
```

<212> TYPE: PRT
<213> ORGANISM: Homo sapiens

<400> SEQUENCE: 12

Gln Leu Gln Leu Gln Glu Ser Gly Gly Gly Leu Val Gln Pro Gly Gly
1               5                   10                  15

Ser Leu Arg Leu Ser Cys Ser Ala Ser Gln Phe Ile Leu Ser Asn Tyr
            20                  25                  30

Trp Val His Trp Val Arg Gln Val Pro Gly Glu Gly Leu Val Trp Val
            35                  40                  45

Ser Arg Ile Asn Glu Asp Gly Ser Val Thr Ser Tyr Ala Asp Ser Val
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Val Asp Asp Thr Ala Val Tyr Tyr Cys
                85                  90                  95

Val Arg Asp Leu Cys Trp Glu Arg Asp Asp Trp Gly Gln Gly Thr Leu
            100                 105                 110

Val Ser Val Ser Ser
        115

<210> SEQ ID NO 13
<211> LENGTH: 122
<212> TYPE: PRT
<213> ORGANISM: Homo sapiens

<400> SEQUENCE: 13

Gln Val Gln Leu Val Gln Ser Gly Gly Gly Val Val Gln Pro Gly Gly
1               5                   10                  15

Ser Leu Arg Leu Ser Cys Ala Ala Ser Pro Phe Thr Phe Lys Thr Ser
            20                  25                  30

Ile Leu His Trp Val Arg Gln Ala Pro Gly Lys Gly Leu Glu Trp Val
            35                  40                  45

Ser Ala Met Ser Tyr Asp Gly Phe Ser Lys Tyr Tyr Ala Asp Ser Val
        50                  55                  60

Lys Gly Arg Leu Thr Ile Ser Arg Asp Ser Ser Thr Asn Thr Leu Tyr
65                  70                  75                  80

Leu Glu Met Asn Ser Leu Arg Phe Glu Asp Thr Ala Leu Tyr Phe Cys
                85                  90                  95

Ala Arg Glu Ala Tyr Thr Ser Gly Arg Ala Gly Cys Phe Asn Pro Trp
            100                 105                 110

Gly Gln Gly Val Leu Val Ser Val Ser Ser
        115                 120

<210> SEQ ID NO 14
<211> LENGTH: 121
<212> TYPE: PRT
<213> ORGANISM: Homo sapiens

<400> SEQUENCE: 14

Gln Val Leu Lys Glu Ser Gly Gly Val Val Gln Pro Gly Gly Ser
1               5                   10                  15

Leu Arg Leu Ser Cys Ala Ala Ser Pro Phe Thr Phe Glu Thr Ser Ile
            20                  25                  30

Leu His Trp Val Arg Gln Ala Pro Gly Lys Gly Leu Glu Trp Val Ser
            35                  40                  45

Ala Met Ser Tyr Asp Gly Phe Ser Lys Tyr Tyr Ala Asp Ser Val Lys

```
                    50                  55                  60
Gly Arg Leu Thr Ile Ser Arg Asp Ser Thr Asn Thr Leu Tyr Leu
 65                  70                  75                  80

Glu Met Asn Ser Leu Arg Phe Glu Asp Thr Ala Leu Tyr Phe Cys Ala
                     85                  90                  95

Arg Glu Ala Tyr Thr Ser Gly Arg Ala Gly Cys Phe Asp Pro Trp Gly
                100                 105                 110

Gln Gly Val Leu Val Ser Val Ser Ser
            115                 120

<210> SEQ ID NO 15
<211> LENGTH: 117
<212> TYPE: PRT
<213> ORGANISM: Homo sapiens

<400> SEQUENCE: 15

Glu Val Gln Leu Val Glu Ser Gly Gly Gly Leu Val Gln Pro Gly Gly
  1               5                  10                  15

Ser Leu Arg Val Ser Cys Ala Ala Ser Gly Phe Thr Leu Asn Thr Tyr
             20                  25                  30

Trp Met His Trp Val Arg Gln Ala Pro Gly Lys Gly Leu Val Trp Val
         35                  40                  45

Ser Arg Ile Asn Glu Asp Gly Thr Thr Ile Ser Tyr Ala Asp Ser Val
     50                  55                  60

Arg Gly Arg Phe Thr Ile Ser Arg Asp Asn Ala Glu Asn Thr Leu Tyr
 65                  70                  75                  80

Leu Gln Met His Ser Leu Arg Ala Glu Asp Thr Gly Val Tyr Tyr Cys
                 85                  90                  95

Ala Arg Asp Phe Thr Gly Pro Phe Asp Ser Trp Gly Gln Gly Thr Leu
                100                 105                 110

Val Ser Val Ser Ser
            115

<210> SEQ ID NO 16
<211> LENGTH: 116
<212> TYPE: PRT
<213> ORGANISM: Homo sapiens

<400> SEQUENCE: 16

Gln Leu Gln Leu Gln Glu Ser Gly Gly Gly Leu Val Gln Pro Gly Gly
  1               5                  10                  15

Ser Leu Arg Leu Ser Cys Val Val Ser Gly Phe Thr Phe Ser Ser His
             20                  25                  30

Ala Met Ser Trp Val Arg Gln Ala Pro Gly Lys Gly Leu Glu Trp Val
         35                  40                  45

Ser Ser Ile Ser Ile Ser Gly Gly Asp Thr Phe Tyr Ala Asp Ser Val
     50                  55                  60

Arg Gly Arg Phe Thr Ile Phe Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Thr Glu Thr Ser Pro Asn Asp Tyr Trp Gly Gln Gly Thr Leu Val
                100                 105                 110

Ser Val Ser Ser
            115
```

```
<210> SEQ ID NO 17
<211> LENGTH: 116
<212> TYPE: PRT
<213> ORGANISM: Homo sapiens

<400> SEQUENCE: 17

Glu Val Gln Leu Val Glu Thr Gly Gly Gly Leu Val Gln Pro Gly Gly
1               5                   10                  15

Ser Leu Arg Leu Ser Cys Val Val Ser Gly Phe Thr Phe Ser Ser His
            20                  25                  30

Ala Met Ser Trp Val Arg Gln Ala Pro Gly Lys Gly Leu Glu Trp Val
        35                  40                  45

Ser Ser Ile Ser Ile Ser Gly Gly Asp Thr Phe Tyr Ala Asp Ser Val
    50                  55                  60

Arg Gly Arg Phe Thr Ile Phe Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Thr Glu Thr Ser Pro Asn Asp Tyr Trp Gly Gln Gly Thr Leu Val
            100                 105                 110

Thr Val Ser Ser
        115

<210> SEQ ID NO 18
<211> LENGTH: 117
<212> TYPE: PRT
<213> ORGANISM: Homo sapiens

<400> SEQUENCE: 18

Glu Val Gln Leu Val Glu Ser Gly Gly Gly Leu Val Gln Pro Gly Gly
1               5                   10                  15

Ser Leu Arg Val Ser Cys Ala Ala Ser Gly Phe Thr Leu Asn Thr Tyr
            20                  25                  30

Trp Met His Trp Val Arg Gln Ala Pro Gly Lys Gly Leu Val Trp Val
        35                  40                  45

Ser Arg Ile Asn Glu Asp Gly Thr Thr Ile Ser Tyr Ala Asp Ser Val
    50                  55                  60

Arg Gly Arg Phe Thr Ile Ser Arg Asp Asn Ala Glu Asn Thr Leu Tyr
65                  70                  75                  80

Leu Gln Met His Ser Leu Arg Ala Glu Asp Thr Gly Val Tyr Tyr Cys
                85                  90                  95

Ala Arg Asp Phe Thr Gly Pro Phe Asp Ser Trp Gly Gln Gly Thr Leu
            100                 105                 110

Val Ser Val Ser Ser
        115

<210> SEQ ID NO 19
<211> LENGTH: 117
<212> TYPE: PRT
<213> ORGANISM: Homo sapiens

<400> SEQUENCE: 19

Glu Val Gln Leu Val Glu Ser Gly Gly Gly Leu Val Gln Pro Gly Gly
1               5                   10                  15

Ser Leu Arg Val Ser Cys Ala Ala Ser Gly Phe Thr Leu Asn Thr Tyr
            20                  25                  30

Trp Met His Trp Val Arg Gln Ala Pro Gly Lys Gly Leu Val Trp Val
        35                  40                  45
```

```
Ser Arg Ile Asn Glu Asp Gly Thr Thr Ile Ser Tyr Ala Asp Ser Val
    50                  55                  60

Arg Gly Arg Phe Thr Ile Ser Arg Asp Asn Ala Glu Asn Thr Leu Tyr
65                  70                  75                  80

Leu Gln Met His Ser Leu Arg Ala Glu Asp Thr Gly Val Tyr Tyr Cys
                85                  90                  95

Ala Arg Asp Phe Thr Gly Pro Phe Asp Ser Trp Gly Gln Gly Thr Leu
                100                 105                 110

Val Ser Val Ser Ser
            115

<210> SEQ ID NO 20
<211> LENGTH: 112
<212> TYPE: PRT
<213> ORGANISM: Homo sapiens

<400> SEQUENCE: 20

Asp Val Val Leu Thr Gln Ser Pro Leu Phe Leu Pro Val Thr Pro Gly
1               5                   10                  15

Glu Pro Ala Ser Ile Ser Cys Arg Ser Ser Gln Ser Leu Leu His Ser
                20                  25                  30

Arg Gly His Thr Ser Leu His Trp Tyr Leu Gln Lys Pro Gly Gln Ser
            35                  40                  45

Pro His Leu Leu Ile Tyr Ser Val Phe Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Glu Pro Pro Tyr Thr Phe Gly Gln Gly Thr Lys Leu Glu Ile Lys
                100                 105                 110

<210> SEQ ID NO 21
<211> LENGTH: 112
<212> TYPE: PRT
<213> ORGANISM: Homo sapiens

<400> SEQUENCE: 21

Asp Ile Val Met Thr Gln Ser Pro Leu Ser Leu Pro Val Thr Pro Gly
1               5                   10                  15

Glu Ala Ala Ser Ile Ser Cys Arg Ser Ser Gln Ser Leu Leu His Arg
                20                  25                  30

Asn Gly Lys Thr Phe Phe Ala Trp Tyr Leu Gln Lys Pro Gly Gln Ser
            35                  40                  45

Pro Gln Ile Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Leu Gln Thr Pro Tyr Thr Phe Gly Gln Gly Thr Lys Leu Glu Ile Lys
                100                 105                 110

<210> SEQ ID NO 22
<211> LENGTH: 107
<212> TYPE: PRT
<213> ORGANISM: Homo sapiens
```

<400> SEQUENCE: 22

Asp Ile Val Met Thr Gln Ser Pro Ser Ser Val Ser Ala Ser Val Gly
1               5                   10                  15

Asp Lys Val Thr Ile Thr Cys Arg Ala Ser Gln Gly Ile Ser Arg Trp
            20                  25                  30

Leu Ala Trp Tyr Gln Gln Lys Pro Gly Glu Ala Pro Glu Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Ile
                85                  90                  95

Thr Phe Gly Gln Gly Thr Arg Leu Gln Ile Lys
            100                 105

<210> SEQ ID NO 23
<211> LENGTH: 106
<212> TYPE: PRT
<213> ORGANISM: Homo sapiens

<400> SEQUENCE: 23

Gln Leu Val Leu Thr Gln Pro Pro Ser Val Ser Val Ser Pro Gly Gln
1               5                   10                  15

Thr Ala Ser Ile Thr Cys Ser Gly Asp Glu Leu Arg Asn Lys Tyr Thr
            20                  25                  30

Ser Trp Tyr Gln Gln Lys Ser Gly Gln Ser Pro Val Leu Val Ile Tyr
        35                  40                  45

Gln Asp Asn Asn Arg Pro Ser Gly Ile Pro Glu Arg Phe Ser Gly Ser
50                  55                  60

Gln Ser Gly Asp Thr Ala Thr Leu Thr Ile Ser Gly Thr Gln Ala Val
65                  70                  75                  80

Asp Glu Ala Asp Tyr Tyr Cys Gln Ala Trp Val Ser Gln Thr Leu Val
                85                  90                  95

Phe Gly Gly Gly Thr Lys Leu Thr Val Leu
            100                 105

<210> SEQ ID NO 24
<211> LENGTH: 109
<212> TYPE: PRT
<213> ORGANISM: Homo sapiens

<400> SEQUENCE: 24

Gln Ala Gly Leu Thr Gln Pro Pro Ser Val Ser Val Ala Pro Gly Gln
1               5                   10                  15

Thr Ala Thr Ile Pro Cys Gly Gly Asn Asn Ile Gly Ser Lys His Val
            20                  25                  30

His Trp Tyr Gln Gln Lys Pro Gly Gln Ala Pro Val Ala Val Val Tyr
        35                  40                  45

Asp Asp Ser Asp Arg Pro Ser Gly Val Pro Glu Arg Phe Ser Gly Ser
50                  55                  60

Asn Ser Gly Asn Thr Ala Thr Leu Thr Ile Ser Ser Val Glu Ala Gly
65                  70                  75                  80

Asp Glu Ala Asp Tyr Tyr Cys Gln Val Trp Asp Arg Ser Ser Asp His
                85                  90                  95

```
Phe Trp Leu Phe Gly Gly Gly Thr Arg Leu Thr Val Leu
            100                 105
```

<210> SEQ ID NO 25
<211> LENGTH: 109
<212> TYPE: PRT
<213> ORGANISM: Homo sapiens

<400> SEQUENCE: 25

```
Gln Leu Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Ser
            20                  25                  30

Asn Phe Val Ser Trp Tyr Gln His Pro Gly Lys Ala Pro Lys Leu
        35                  40                  45

Met Ile Tyr Glu Val Ser Gln Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Asp Asp Glu Ala Asp Tyr Tyr Cys Ser Ser Tyr Ala Gly Ser
                85                  90                  95

Val Val Leu Phe Gly Gly Gly Thr Lys Leu Thr Val Leu
            100                 105
```

<210> SEQ ID NO 26
<211> LENGTH: 109
<212> TYPE: PRT
<213> ORGANISM: Homo sapiens

<400> SEQUENCE: 26

```
Gln Leu Val Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Ser
            20                  25                  30

Asn Phe Val Ser Trp Tyr Gln His Pro Gly Lys Ala Pro Lys Leu
        35                  40                  45

Met Ile Tyr Glu Val Ser Gln Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Asp Asp Glu Ala Asp Tyr Tyr Cys Ser Ser Tyr Ala Gly Ser
                85                  90                  95

Val Val Leu Phe Gly Gly Gly Thr Lys Leu Thr Val Leu
            100                 105
```

<210> SEQ ID NO 27
<211> LENGTH: 107
<212> TYPE: PRT
<213> ORGANISM: Homo sapiens

<400> SEQUENCE: 27

```
Asp Ile Val Met Thr Gln Ser Pro Ala Thr Leu Ser Leu Ser Pro Gly
1               5                   10                  15

Glu Arg Ala Thr Leu Ser Cys Trp Ala Ser Gln Tyr Ile Asn Thr Tyr
            20                  25                  30

Val Asn Trp Tyr Gln His Lys Pro Gly Gln Ala Pro Arg Leu Leu Ile
        35                  40                  45

Tyr Asp Ala Ser Lys Arg Ala Thr Gly Ile Pro Ala Arg Phe Ser Gly
```

```
                50                  55                  60
Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Gly Ser Asn Trp Pro Leu
                 85                  90                  95

Thr Phe Gly Gln Gly Thr Arg Leu Glu Ile Lys
                100                 105

<210> SEQ ID NO 28
<211> LENGTH: 107
<212> TYPE: PRT
<213> ORGANISM: Homo sapiens

<400> SEQUENCE: 28

Glu Ile Val Met Thr Gln Ser Pro Ser Phe Val Ser Ala Ser Val Gly
  1               5                  10                  15

Asp Arg Val Thr Ile Thr Cys Arg Ala Ser Gln Asp Ile Ser Asn Trp
                 20                  25                  30

Leu Val Trp Tyr Gln Gln Lys Pro Gly Lys Ala Pro Lys Leu Leu Ile
                 35                  40                  45

Tyr Ala Ser Ser Asn Leu Gln Ser Gly Val Pro Ser Arg Phe Ser Gly
             50                  55                  60

Ser Gly Ser Gly Thr Asp Phe Ala Leu Thr Ile Ser Ser Leu Gln Pro
 65                  70                  75                  80

Glu Asp Phe Ala Thr Tyr Tyr Cys Gln Gln Glu Asn Ser Phe Pro Tyr
                 85                  90                  95

Thr Phe Gly Gln Gly Thr Lys Leu Glu Ile Lys
                100                 105

<210> SEQ ID NO 29
<211> LENGTH: 112
<212> TYPE: PRT
<213> ORGANISM: Homo sapiens

<400> SEQUENCE: 29

Val Ile Trp Met Thr Gln Ser Pro Leu Ser Leu Pro Val Thr Pro Gly
  1               5                  10                  15

Glu Ala Ala Ser Ile Ser Cys Arg Ser Ser Gln Ser Leu Leu His Arg
                 20                  25                  30

Asn Gly Arg Thr Phe Phe Ala Trp Tyr Leu Gln Lys Pro Gly Gln Ser
                 35                  40                  45

Pro Gln Ile Leu Ile Tyr Leu Gly Ser Asn Arg Ala Phe Gly Val Pro
             50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Ile Tyr Tyr Cys Met Gln Gly
                 85                  90                  95

Leu Gln Thr Pro Tyr Thr Phe Gly Gln Gly Thr Lys Leu Glu Ile Lys
                100                 105                 110

<210> SEQ ID NO 30
<211> LENGTH: 112
<212> TYPE: PRT
<213> ORGANISM: Homo sapiens

<400> SEQUENCE: 30

Val Ile Trp Met Thr Gln Ser Pro Leu Ser Leu Pro Val Thr Pro Gly
  1               5                  10                  15
```

Glu Ala Ala Ser Ile Ser Cys Arg Ser Ser Gln Ser Leu Leu His Arg
            20                  25                  30

Asn Gly Arg Thr Phe Phe Ala Trp Tyr Leu Gln Lys Pro Gly Gln Ser
        35                  40                  45

Pro Gln Ile Leu Ile Tyr Leu Gly Ser Asn Arg Ala Phe Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Leu Gln Thr Pro Tyr Thr Phe Gly Gln Gly Thr Lys Leu Glu Ile Lys
            100                 105                 110

<210> SEQ ID NO 31
<211> LENGTH: 107
<212> TYPE: PRT
<213> ORGANISM: Homo sapiens

<400> SEQUENCE: 31

Asp Ile Val Met Thr Gln Thr Pro Ser Thr Gln Ser Ala Ser Val Gly
1               5                   10                  15

Asp Arg Val Thr Ile Thr Cys Arg Ala Ser Gln Ser Ile Ser Ile Trp
            20                  25                  30

Leu Ala Trp Tyr Gln Gln Lys Pro Gly Lys Ala Pro Lys Leu Leu Ile
        35                  40                  45

His Asp Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Arg Tyr Asn Asp Tyr Pro Pro
                85                  90                  95

Thr Phe Gly Pro Gly Thr Lys Val Glu Ile Lys
            100                 105

<210> SEQ ID NO 32
<211> LENGTH: 107
<212> TYPE: PRT
<213> ORGANISM: Homo sapiens

<400> SEQUENCE: 32

Glu Ile Val Met Thr Gln Ser Pro Ser Thr Gln Ser Ala Ser Val Gly
1               5                   10                  15

Asp Arg Val Thr Ile Thr Cys Arg Ala Ser Gln Ser Ile Ser Ile Trp
            20                  25                  30

Leu Ala Trp Tyr Gln Gln Lys Pro Gly Lys Ala Pro Lys Leu Leu Ile
        35                  40                  45

His Asp Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Ser Ala Thr Tyr Tyr Cys Gln Arg Tyr Asn Asp Tyr Pro Pro
                85                  90                  95

Thr Phe Gly Pro Gly Thr Lys Val Glu Ile Lys
            100                 105

<210> SEQ ID NO 33

```
<211> LENGTH: 110
<212> TYPE: PRT
<213> ORGANISM: Homo sapiens

<400> SEQUENCE: 33

Gln Ser Val Leu Thr Gln Pro Pro Ser Val Ser Gly Thr Pro Gly Gln
1               5                   10                  15

Arg Val Thr Ile Ser Cys Ser Gly Ser Asn Ser Asn Ala Gly Arg Asp
            20                  25                  30

Tyr Val Ser Trp Tyr Gln Gln Val Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Asp Gly Asp Tyr Tyr Cys Ile Val Trp Asp Gly Ser Leu
                85                  90                  95

Ser Gly Tyr Val Phe Gly Thr Gly Thr Lys Val Thr Val Leu
            100                 105                 110

<210> SEQ ID NO 34
<211> LENGTH: 109
<212> TYPE: PRT
<213> ORGANISM: Homo sapiens

<400> SEQUENCE: 34

Ser Tyr Glu Leu Thr Gln Pro Ser Ser Leu Thr Val Ser Pro Gly Gly
1               5                   10                  15

Thr Val Thr Leu Thr Cys Gly Leu Ser Ser Gly Ala Val Thr Ser Gly
            20                  25                  30

His Tyr Pro Tyr Trp Phe Gln Gln Lys Pro Gly Gln Ala Pro Lys Thr
        35                  40                  45

Leu Ile Phe Asp Thr Ser Arg Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Asp Ala Asp Tyr Tyr Cys Leu Leu Ala Cys Asn Gly
                85                  90                  95

Ala Cys Val Phe Gly Gly Gly Thr Lys Leu Thr Val Leu
            100                 105

<210> SEQ ID NO 35
<211> LENGTH: 109
<212> TYPE: PRT
<213> ORGANISM: Homo sapiens

<400> SEQUENCE: 35

Ser Tyr Glu Leu Thr Gln Pro Ser Ser Leu Thr Val Ser Pro Gly Gly
1               5                   10                  15

Thr Val Thr Leu Thr Cys Gly Leu Ser Ser Gly Ala Val Thr Ser Gly
            20                  25                  30

His Tyr Pro Tyr Trp Phe Gln Gln Lys Pro Gly Gln Ala Pro Lys Thr
        35                  40                  45

Leu Ile Phe Asp Thr Ser Arg Lys His Ser Trp Thr Pro Ala Arg Phe
    50                  55                  60

Ser Gly Ser Leu Leu Gly Gly Lys Ala Ala Leu Thr Leu Ser Gly Ala
65                  70                  75                  80
```

-continued

Gln Pro Glu Asp Asp Ala Asp Tyr Tyr Cys Leu Leu Ala Cys Asn Gly
                85                  90                  95

Ala Cys Val Phe Gly Gly Gly Thr Lys Leu Thr Val Leu
            100                 105

<210> SEQ ID NO 36
<211> LENGTH: 110
<212> TYPE: PRT
<213> ORGANISM: Homo sapiens

<400> SEQUENCE: 36

Gln Ser Val Leu Thr Gln Pro Pro Ser Val Ser Gly Thr Pro Gly Gln
1               5                   10                  15

Arg Val Thr Ile Ser Cys Ser Gly Ser Asn Ser Asn Val Gly Arg Asp
            20                  25                  30

Tyr Val Ser Trp Tyr Gln Gln Val Pro Gly Thr Ala Pro Lys Leu Leu
        35                  40                  45

Ile Tyr Lys Asn Asn Arg Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Asp Gly Asp Tyr Tyr Cys Ile Val Trp Asp Gly Ser Leu
                85                  90                  95

Ser Gly Tyr Val Phe Gly Thr Gly Thr Lys Val Thr Val Leu
            100                 105                 110

<210> SEQ ID NO 37
<211> LENGTH: 110
<212> TYPE: PRT
<213> ORGANISM: Homo sapiens

<400> SEQUENCE: 37

Gln Leu Val Leu Thr Gln Pro Pro Ser Val Ser Gly Thr Pro Gly Gln
1               5                   10                  15

Arg Val Thr Ile Ser Cys Ser Gly Ser Asn Ser Asn Val Gly Arg Asp
            20                  25                  30

Tyr Val Ser Trp Tyr Gln Gln Val Pro Gly Thr Ala Pro Lys Leu Leu
        35                  40                  45

Ile Tyr Lys Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Asp Gly Asp Tyr Tyr Cys Ile Val Trp Asp Gly Ser Leu
                85                  90                  95

Ser Gly Tyr Val Phe Gly Thr Gly Thr Lys Val Thr Val Leu
            100                 105                 110

<210> SEQ ID NO 38
<211> LENGTH: 29
<212> TYPE: PRT
<213> ORGANISM: Homo sapiens

<400> SEQUENCE: 38

Gln Val Thr Leu Lys Glu Ser Gly Gly Leu Val Gln Pro Gly Gly
1               5                   10                  15

Ser Leu Arg Leu Ser Cys Val Ala Ser Gly Phe Thr Phe
            20                  25

```
<210> SEQ ID NO 39
<211> LENGTH: 6
<212> TYPE: PRT
<213> ORGANISM: Homo sapiens

<400> SEQUENCE: 39

Arg Thr Tyr Trp Met His
1               5

<210> SEQ ID NO 40
<211> LENGTH: 14
<212> TYPE: PRT
<213> ORGANISM: Homo sapiens

<400> SEQUENCE: 40

Trp Val Arg Gln Asp Pro Gly Lys Gly Leu Val Trp Val Ser
1               5                   10

<210> SEQ ID NO 41
<211> LENGTH: 17
<212> TYPE: PRT
<213> ORGANISM: Homo sapiens

<400> SEQUENCE: 41

Arg Leu Asp Glu Val Gly Arg Leu Thr Ser Tyr Ala Asp Ser Val Asn
1               5                   10                  15

Gly

<210> SEQ ID NO 42
<211> LENGTH: 32
<212> TYPE: PRT
<213> ORGANISM: Homo sapiens

<400> SEQUENCE: 42

Arg Phe Thr Ile Ser Arg Asp Asn Ala Lys Asn Ile Leu Tyr Leu Gln
1               5                   10                  15

Met Asn Ser Leu Arg Ala Glu Asp Thr Gly Val Tyr Tyr Cys Ala Arg
            20                  25                  30

<210> SEQ ID NO 43
<211> LENGTH: 8
<212> TYPE: PRT
<213> ORGANISM: Homo sapiens

<400> SEQUENCE: 43

Asp Leu Ser Gly Ser Ala Asp Tyr
1               5

<210> SEQ ID NO 44
<211> LENGTH: 11
<212> TYPE: PRT
<213> ORGANISM: Homo sapiens

<400> SEQUENCE: 44

Trp Gly Gln Gly Thr Leu Val Thr Val Ser Ser
1               5                   10

<210> SEQ ID NO 45
<211> LENGTH: 23
<212> TYPE: PRT
<213> ORGANISM: Homo sapiens

<400> SEQUENCE: 45

Asp Val Val Leu Thr Gln Ser Pro Leu Phe Leu Pro Val Thr Pro Gly
```

```
1               5                   10                  15
Glu Pro Ala Ser Ile Ser Cys
                20

<210> SEQ ID NO 46
<211> LENGTH: 16
<212> TYPE: PRT
<213> ORGANISM: Homo sapiens

<400> SEQUENCE: 46

Arg Ser Ser Gln Ser Leu Leu His Ser Arg Gly His Thr Ser Leu His
1               5                   10                  15

<210> SEQ ID NO 47
<211> LENGTH: 15
<212> TYPE: PRT
<213> ORGANISM: Homo sapiens

<400> SEQUENCE: 47

Trp Tyr Leu Gln Lys Pro Gly Gln Ser Pro His Leu Leu Ile Tyr
1               5                   10                  15

<210> SEQ ID NO 48
<211> LENGTH: 7
<212> TYPE: PRT
<213> ORGANISM: Homo sapiens

<400> SEQUENCE: 48

Ser Val Phe Asn Arg Ala Ser
1               5

<210> SEQ ID NO 49
<211> LENGTH: 32
<212> TYPE: PRT
<213> ORGANISM: Homo sapiens

<400> SEQUENCE: 49

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
                20                  25                  30

<210> SEQ ID NO 50
<211> LENGTH: 9
<212> TYPE: PRT
<213> ORGANISM: Homo sapiens

<400> SEQUENCE: 50

Met Gln Ala Leu Glu Pro Pro Tyr Thr
1               5

<210> SEQ ID NO 51
<211> LENGTH: 10
<212> TYPE: PRT
<213> ORGANISM: Homo sapiens

<400> SEQUENCE: 51

Phe Gly Gln Gly Thr Lys Leu Glu Ile Lys
1               5                   10

<210> SEQ ID NO 52
<211> LENGTH: 29
<212> TYPE: PRT
<213> ORGANISM: Homo sapiens
```

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ser Ala Ser Gln Phe Ile Leu
            20                  25

<210> SEQ ID NO 53
<211> LENGTH: 6
<212> TYPE: PRT
<213> ORGANISM: Homo sapiens

<400> SEQUENCE: 53

Ser Asn Tyr Trp Val His
1               5

<210> SEQ ID NO 54
<211> LENGTH: 14
<212> TYPE: PRT
<213> ORGANISM: Homo sapiens

<400> SEQUENCE: 54

Trp Val Arg Gln Val Pro Gly Glu Gly Leu Val Trp Val Ser
1               5                   10

<210> SEQ ID NO 55
<211> LENGTH: 17
<212> TYPE: PRT
<213> ORGANISM: Homo sapiens

<400> SEQUENCE: 55

Arg Ile Asn Glu Asp Gly Ser Val Thr Ser Tyr Ala Asp Ser Val Lys
1               5                   10                  15

Gly

<210> SEQ ID NO 56
<211> LENGTH: 32
<212> TYPE: PRT
<213> ORGANISM: Homo sapiens

<400> SEQUENCE: 56

Arg Phe Thr Ile Ser Arg Asp Asn Ala Lys Asn Thr Leu Tyr Leu Gln
1               5                   10                  15

Met Asn Ser Leu Arg Val Asp Asp Thr Ala Val Tyr Tyr Cys Val Arg
            20                  25                  30

<210> SEQ ID NO 57
<211> LENGTH: 8
<212> TYPE: PRT
<213> ORGANISM: Homo sapiens

<400> SEQUENCE: 57

Asp Leu Cys Gly Glu Arg Asp Asp
1               5

<210> SEQ ID NO 58
<211> LENGTH: 11
<212> TYPE: PRT
<213> ORGANISM: Homo sapiens

<400> SEQUENCE: 58

Trp Gly Gln Gly Thr Leu Val Ser Val Ser Ser
1               5                   10

<210> SEQ ID NO 59
<211> LENGTH: 23
<212> TYPE: PRT
<213> ORGANISM: Homo sapiens

<400> SEQUENCE: 59

Asp Ile Val Met Thr Gln Ser Pro Leu Ser Leu Pro Val Thr Pro Gly
1               5                   10                  15

Glu Ala Ala Ser Ile Ser Cys
            20

<210> SEQ ID NO 60
<211> LENGTH: 16
<212> TYPE: PRT
<213> ORGANISM: Homo sapiens

<400> SEQUENCE: 60

Arg Ser Ser Gln Ser Leu Leu His Arg Asn Gly Lys Thr Phe Phe Ala
1               5                   10                  15

<210> SEQ ID NO 61
<211> LENGTH: 15
<212> TYPE: PRT
<213> ORGANISM: Homo sapiens

<400> SEQUENCE: 61

Trp Tyr Leu Gln Lys Pro Gly Gln Ser Pro Gln Ile Leu Ile Tyr
1               5                   10                  15

<210> SEQ ID NO 62
<211> LENGTH: 7
<212> TYPE: PRT
<213> ORGANISM: Homo sapiens

<400> SEQUENCE: 62

Leu Gly Ser Asn Arg Ala Ser
1               5

<210> SEQ ID NO 63
<211> LENGTH: 32
<212> TYPE: PRT
<213> ORGANISM: Homo sapiens

<400> SEQUENCE: 63

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Ile Tyr Tyr Cys
            20                  25                  30

<210> SEQ ID NO 64
<211> LENGTH: 9
<212> TYPE: PRT
<213> ORGANISM: Homo sapiens

<400> SEQUENCE: 64

Met Gln Gly Leu Gln Thr Pro Tyr Thr
1               5

<210> SEQ ID NO 65
<211> LENGTH: 10
<212> TYPE: PRT
<213> ORGANISM: Homo sapiens

```
<400> SEQUENCE: 65

Phe Gly Gln Gly Thr Lys Leu Glu Ile Lys
1               5                   10

<210> SEQ ID NO 66
<211> LENGTH: 29
<212> TYPE: PRT
<213> ORGANISM: Homo sapiens

<400> SEQUENCE: 66

Glu Val Gln Leu Val Gln Ser Gly Gly Gly Leu Val Gln Pro Gly Gly
1               5                   10                  15

Ser Leu Gly Leu Ser Cys Ala Ala Ser Gly Phe Ile Phe
            20                  25

<210> SEQ ID NO 67
<211> LENGTH: 6
<212> TYPE: PRT
<213> ORGANISM: Homo sapiens

<400> SEQUENCE: 67

Thr Ser Tyr Ala Met Thr
1               5

<210> SEQ ID NO 68
<211> LENGTH: 14
<212> TYPE: PRT
<213> ORGANISM: Homo sapiens

<400> SEQUENCE: 68

Trp Val Arg Gln Ala Pro Gly Lys Gly Leu Glu Trp Val Ser
1               5                   10

<210> SEQ ID NO 69
<211> LENGTH: 17
<212> TYPE: PRT
<213> ORGANISM: Homo sapiens

<400> SEQUENCE: 69

Val Ile Thr Gly Asn Val Gly Thr Ser Tyr Tyr Ala Asp Ser Val Lys
1               5                   10                  15

Gly

<210> SEQ ID NO 70
<211> LENGTH: 32
<212> TYPE: PRT
<213> ORGANISM: Homo sapiens

<400> SEQUENCE: 70

Arg Phe Thr Ile Ser Arg Asp Asn Ser Lys Lys Thr Val Ser Leu Gln
1               5                   10                  15

Met Asn Ser Leu Arg Ala Glu Asp Thr Ala Ile Tyr Tyr Cys Val Lys
            20                  25                  30

<210> SEQ ID NO 71
<211> LENGTH: 13
<212> TYPE: PRT
<213> ORGANISM: Homo sapiens

<400> SEQUENCE: 71

Thr Arg Tyr Asp Phe Ser Ser Gly Tyr Tyr Phe Asp Asp
1               5                   10
```

<210> SEQ ID NO 72
<211> LENGTH: 11
<212> TYPE: PRT
<213> ORGANISM: Homo sapiens

<400> SEQUENCE: 72

Trp Gly Gln Gly Thr Leu Val Ser Val Ser Ser
1               5                   10

<210> SEQ ID NO 73
<211> LENGTH: 23
<212> TYPE: PRT
<213> ORGANISM: Homo sapiens

<400> SEQUENCE: 73

Asp Ile Val Met Thr Gln Ser Pro Ser Ser Val Ser Ala Ser Val Gly
1               5                   10                  15

Asp Lys Val Thr Ile Thr Cys
            20

<210> SEQ ID NO 74
<211> LENGTH: 11
<212> TYPE: PRT
<213> ORGANISM: Homo sapiens

<400> SEQUENCE: 74

Arg Ala Ser Gln Gly Ile Ser Arg Trp Leu Ala
1               5                   10

<210> SEQ ID NO 75
<211> LENGTH: 15
<212> TYPE: PRT
<213> ORGANISM: Homo sapiens

<400> SEQUENCE: 75

Trp Tyr Gln Gln Lys Pro Gly Glu Ala Pro Glu Leu Leu Ile Tyr
1               5                   10                  15

<210> SEQ ID NO 76
<211> LENGTH: 7
<212> TYPE: PRT
<213> ORGANISM: Homo sapiens

<400> SEQUENCE: 76

Ala Ala Ser Ser Leu Gln Ser
1               5

<210> SEQ ID NO 77
<211> LENGTH: 32
<212> TYPE: PRT
<213> ORGANISM: Homo sapiens

<400> SEQUENCE: 77

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 78
<211> LENGTH: 9
<212> TYPE: PRT
<213> ORGANISM: Homo sapiens

<400> SEQUENCE: 78

Gln Gln Ala Asn Ser Phe Pro Ile Thr
1               5

<210> SEQ ID NO 79
<211> LENGTH: 10
<212> TYPE: PRT
<213> ORGANISM: Homo sapiens

<400> SEQUENCE: 79

Phe Gly Gln Gly Thr Arg Leu Gln Ile Lys
1               5                   10

<210> SEQ ID NO 80
<211> LENGTH: 29
<212> TYPE: PRT
<213> ORGANISM: Homo sapiens

<400> SEQUENCE: 80

Glu Val Gln Leu Val Glu Ser Gly Gly Thr Leu Val Gln Pro Gly Gly
1               5                   10                  15

Ser Leu Arg Leu Ser Cys Ala Ala Ser Gly Phe Thr Phe
            20                  25

<210> SEQ ID NO 81
<211> LENGTH: 6
<212> TYPE: PRT
<213> ORGANISM: Homo sapiens

<400> SEQUENCE: 81

Ser Asp Tyr Trp Met Asn
1               5

<210> SEQ ID NO 82
<211> LENGTH: 14
<212> TYPE: PRT
<213> ORGANISM: Homo sapiens

<400> SEQUENCE: 82

Trp Val Arg Gln Ala Pro Gly Lys Gly Leu Glu Trp Val Ala
1               5                   10

<210> SEQ ID NO 83
<211> LENGTH: 17
<212> TYPE: PRT
<213> ORGANISM: Homo sapiens

<400> SEQUENCE: 83

Asn Ile Lys Gln Asp Gly Ser Glu Lys Tyr Tyr Val Asp Ser Leu Arg
1               5                   10                  15

Gly

<210> SEQ ID NO 84
<211> LENGTH: 32
<212> TYPE: PRT
<213> ORGANISM: Homo sapiens

<400> SEQUENCE: 84

Arg Val Thr Ile Ser Arg Asp Asn Ala Gln Asn Ser Val Phe Leu Gln
1               5                   10                  15

Met His Ser Leu Ser Val Glu Asp Thr Ala Val Tyr Tyr Cys Ala Arg
            20                  25                  30

```
<210> SEQ ID NO 85
<211> LENGTH: 14
<212> TYPE: PRT
<213> ORGANISM: Homo sapiens

<400> SEQUENCE: 85

Asp Gly Tyr Thr Phe Gly Pro Ala Thr Thr Glu Leu Asp His
1               5                  10

<210> SEQ ID NO 86
<211> LENGTH: 11
<212> TYPE: PRT
<213> ORGANISM: Homo sapiens

<400> SEQUENCE: 86

Trp Gly Arg Gly Thr Leu Val Ser Val Ser Ser
1               5                  10

<210> SEQ ID NO 87
<211> LENGTH: 22
<212> TYPE: PRT
<213> ORGANISM: Homo sapiens

<400> SEQUENCE: 87

Gln Leu Val Leu Thr Gln Pro Pro Ser Val Ser Val Ser Pro Gly Gln
1               5                  10                  15

Thr Ala Ser Ile Thr Cys
            20

<210> SEQ ID NO 88
<211> LENGTH: 11
<212> TYPE: PRT
<213> ORGANISM: Homo sapiens

<400> SEQUENCE: 88

Ser Gly Asp Glu Leu Arg Asn Lys Tyr Thr Ser
1               5                  10

<210> SEQ ID NO 89
<211> LENGTH: 15
<212> TYPE: PRT
<213> ORGANISM: Homo sapiens

<400> SEQUENCE: 89

Trp Tyr Gln Gln Lys Ser Gly Gln Ser Pro Val Leu Val Ile Tyr
1               5                  10                  15

<210> SEQ ID NO 90
<211> LENGTH: 7
<212> TYPE: PRT
<213> ORGANISM: Homo sapiens

<400> SEQUENCE: 90

Gln Asp Asn Asn Arg Pro Ser
1               5

<210> SEQ ID NO 91
<211> LENGTH: 32
<212> TYPE: PRT
<213> ORGANISM: Homo sapiens

<400> SEQUENCE: 91

Gly Ile Pro Glu Arg Phe Ser Gly Ser Gln Ser Gly Asp Thr Ala Thr
1               5                  10                  15
```

Leu Thr Ile Ser Gly Thr Gln Ala Val Asp Glu Ala Asp Tyr Tyr Cys
            20                  25                  30

<210> SEQ ID NO 92
<211> LENGTH: 9
<212> TYPE: PRT
<213> ORGANISM: Homo sapiens

<400> SEQUENCE: 92

Gln Ala Trp Val Ser Gln Thr Leu Val
1               5

<210> SEQ ID NO 93
<211> LENGTH: 10
<212> TYPE: PRT
<213> ORGANISM: Homo sapiens

<400> SEQUENCE: 93

Phe Gly Gly Gly Thr Lys Leu Thr Val Leu
1               5                   10

<210> SEQ ID NO 94
<211> LENGTH: 29
<212> TYPE: PRT
<213> ORGANISM: Homo sapiens

<400> SEQUENCE: 94

Glu Val Gln Leu Val Gln Ser Gly Gly Gly Leu Ala Gln Pro Gly Arg
1               5                   10                  15

Ser Leu Arg Leu Ser Cys Ala Ala Ser Gly Phe Gly Phe
            20                  25

<210> SEQ ID NO 95
<211> LENGTH: 6
<212> TYPE: PRT
<213> ORGANISM: Homo sapiens

<400> SEQUENCE: 95

Asp Asp Phe Ala Met His
1               5

<210> SEQ ID NO 96
<211> LENGTH: 14
<212> TYPE: PRT
<213> ORGANISM: Homo sapiens

<400> SEQUENCE: 96

Trp Val Arg Gln Pro Pro Gly Lys Gly Leu Glu Trp Val Ser
1               5                   10

<210> SEQ ID NO 97
<211> LENGTH: 17
<212> TYPE: PRT
<213> ORGANISM: Homo sapiens

<400> SEQUENCE: 97

Gly Leu Thr Trp Asn Gly Gly Ser Ile Asp Tyr Ala Gly Ser Val Arg
1               5                   10                  15

Gly

<210> SEQ ID NO 98
<211> LENGTH: 32
<212> TYPE: PRT
<213> ORGANISM: Homo sapiens

<400> SEQUENCE: 98

Arg Phe Thr Ile Ser Arg Asp Asn Ala Lys Asn Ser Leu Phe Leu Gln
1               5                   10                  15

Met Asn Ser Leu Arg Ala Glu Asp Thr Ala Leu Tyr Tyr Cys Ala Lys
            20                  25                  30

<210> SEQ ID NO 99
<211> LENGTH: 12
<212> TYPE: PRT
<213> ORGANISM: Homo sapiens

<400> SEQUENCE: 99

Gly Leu Ser Gly Gly Thr Met Ala Pro Phe Asp Ile
1               5                   10

<210> SEQ ID NO 100
<211> LENGTH: 11
<212> TYPE: PRT
<213> ORGANISM: Homo sapiens

<400> SEQUENCE: 100

Trp Gly Gln Gly Thr Met Val Ser Val Ser Ser
1               5                   10

<210> SEQ ID NO 101
<211> LENGTH: 22
<212> TYPE: PRT
<213> ORGANISM: Homo sapiens

<400> SEQUENCE: 101

Gln Ala Gly Leu Thr Gln Pro Pro Ser Val Ser Val Ala Pro Gly Gln
1               5                   10                  15

Thr Ala Thr Ile Pro Cys
            20

<210> SEQ ID NO 102
<211> LENGTH: 11
<212> TYPE: PRT
<213> ORGANISM: Homo sapiens

<400> SEQUENCE: 102

Gly Gly Asn Asn Ile Gly Ser Lys His Val His
1               5                   10

<210> SEQ ID NO 103
<211> LENGTH: 15
<212> TYPE: PRT
<213> ORGANISM: Homo sapiens

<400> SEQUENCE: 103

Trp Tyr Gln Gln Lys Pro Gly Gln Ala Pro Val Ala Val Val Tyr
1               5                   10                  15

<210> SEQ ID NO 104
<211> LENGTH: 7
<212> TYPE: PRT
<213> ORGANISM: Homo sapiens

<400> SEQUENCE: 104

Asp Asp Ser Asp Arg Pro Ser
1               5

```
<210> SEQ ID NO 105
<211> LENGTH: 32
<212> TYPE: PRT
<213> ORGANISM: Homo sapiens

<400> SEQUENCE: 105

Gly Val Pro Glu Arg Phe Ser Gly Ser Asn Ser Gly Asn Thr Ala Thr
1               5                   10                  15

Leu Thr Ile Ser Ser Val Glu Ala Gly Asp Glu Ala Asp Tyr Tyr Cys
            20                  25                  30

<210> SEQ ID NO 106
<211> LENGTH: 12
<212> TYPE: PRT
<213> ORGANISM: Homo sapiens

<400> SEQUENCE: 106

Gln Val Trp Asp Arg Ser Ser Asp His Phe Trp Leu
1               5                   10

<210> SEQ ID NO 107
<211> LENGTH: 10
<212> TYPE: PRT
<213> ORGANISM: Homo sapiens

<400> SEQUENCE: 107

Phe Gly Gly Gly Thr Arg Leu Thr Val Leu
1               5                   10

<210> SEQ ID NO 108
<211> LENGTH: 29
<212> TYPE: PRT
<213> ORGANISM: Homo sapiens

<400> SEQUENCE: 108

Glu Val Gln Leu Leu Glu Ser Gly Gly Val Val Gln Pro Gly Arg
1               5                   10                  15

Ser Leu Arg Leu Ser Cys Ala Ala Ser Gly Phe Thr Phe
            20                  25

<210> SEQ ID NO 109
<211> LENGTH: 6
<212> TYPE: PRT
<213> ORGANISM: Homo sapiens

<400> SEQUENCE: 109

Ser Asn Tyr Gly Met His
1               5

<210> SEQ ID NO 110
<211> LENGTH: 14
<212> TYPE: PRT
<213> ORGANISM: Homo sapiens

<400> SEQUENCE: 110

Trp Val Arg Gln Ala Pro Gly Lys Gly Leu Glu Trp Val Ala
1               5                   10

<210> SEQ ID NO 111
<211> LENGTH: 17
<212> TYPE: PRT
<213> ORGANISM: Homo sapiens

<400> SEQUENCE: 111
```

```
Val Val Trp Phe Asp Gly Ser Tyr Lys Tyr Tyr Thr Asp Ser Val Lys
1               5                   10                  15

Gly

<210> SEQ ID NO 112
<211> LENGTH: 32
<212> TYPE: PRT
<213> ORGANISM: Homo sapiens

<400> SEQUENCE: 112

Arg Phe Thr Ile Ser Arg Asp Asn Ser Lys Ser Thr Leu Tyr Leu Gln
1               5                   10                  15

Met Asn Ser Leu Arg Ala Glu Asp Thr Ala Val Tyr Tyr Cys Val Ser
            20                  25                  30

<210> SEQ ID NO 113
<211> LENGTH: 9
<212> TYPE: PRT
<213> ORGANISM: Homo sapiens

<400> SEQUENCE: 113

Pro Ile Met Thr Ser Ala Phe Asp Ile
1               5

<210> SEQ ID NO 114
<211> LENGTH: 11
<212> TYPE: PRT
<213> ORGANISM: Homo sapiens

<400> SEQUENCE: 114

Trp Gly Pro Gly Thr Met Val Ser Val Ser Ser
1               5                   10

<210> SEQ ID NO 115
<211> LENGTH: 22
<212> TYPE: PRT
<213> ORGANISM: Homo sapiens

<400> SEQUENCE: 115

Gln Leu Val Leu Thr Gln Pro Pro Ser Ala Ser Gly Ser Pro Gly Gln
1               5                   10                  15

Ser Val Thr Ile Ser Cys
            20

<210> SEQ ID NO 116
<211> LENGTH: 14
<212> TYPE: PRT
<213> ORGANISM: Homo sapiens

<400> SEQUENCE: 116

Thr Gly Thr Ser Ser Asp Val Gly Gly Ser Asn Phe Val Ser
1               5                   10

<210> SEQ ID NO 117
<211> LENGTH: 15
<212> TYPE: PRT
<213> ORGANISM: Homo sapiens

<400> SEQUENCE: 117

Trp Tyr Gln His His Pro Gly Lys Ala Pro Lys Leu Met Ile Tyr
1               5                   10                  15

<210> SEQ ID NO 118
```

```
<211> LENGTH: 7
<212> TYPE: PRT
<213> ORGANISM: Homo sapiens

<400> SEQUENCE: 118

Glu Val Ser Gln Arg Pro Ser
1               5

<210> SEQ ID NO 119
<211> LENGTH: 32
<212> TYPE: PRT
<213> ORGANISM: Homo sapiens

<400> SEQUENCE: 119

Gly Val Pro Asp Arg Phe Ser Gly Ser Lys Ser Gly Asn Thr Ala Ser
1               5                   10                  15

Leu Thr Val Ser Gly Leu Gln Ala Asp Asp Glu Ala Asp Tyr Tyr Cys
            20                  25                  30

<210> SEQ ID NO 120
<211> LENGTH: 9
<212> TYPE: PRT
<213> ORGANISM: Homo sapiens

<400> SEQUENCE: 120

Ser Ser Tyr Ala Gly Ser Val Val Leu
1               5

<210> SEQ ID NO 121
<211> LENGTH: 10
<212> TYPE: PRT
<213> ORGANISM: Homo sapiens

<400> SEQUENCE: 121

Phe Gly Gly Gly Thr Lys Leu Thr Val Leu
1               5                   10

<210> SEQ ID NO 122
<211> LENGTH: 29
<212> TYPE: PRT
<213> ORGANISM: Homo sapiens

<400> SEQUENCE: 122

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe
            20                  25

<210> SEQ ID NO 123
<211> LENGTH: 6
<212> TYPE: PRT
<213> ORGANISM: Homo sapiens

<400> SEQUENCE: 123

Ser Asn Tyr Gly Met His
1               5

<210> SEQ ID NO 124
<211> LENGTH: 14
<212> TYPE: PRT
<213> ORGANISM: Homo sapiens

<400> SEQUENCE: 124

Trp Val Arg Gln Ala Pro Gly Lys Gly Leu Glu Trp Val Ala
```

-continued

```
<210> SEQ ID NO 125
<211> LENGTH: 17
<212> TYPE: PRT
<213> ORGANISM: Homo sapiens

<400> SEQUENCE: 125

Val Val Trp Leu Asp Gly Ser Tyr Lys Tyr Tyr Thr Gly Ser Val Lys
1               5                   10                  15

Gly

<210> SEQ ID NO 126
<211> LENGTH: 32
<212> TYPE: PRT
<213> ORGANISM: Homo sapiens

<400> SEQUENCE: 126

Arg Phe Thr Ile Ser Arg Asp Asn Ser Lys Ser Thr Leu Tyr Leu Gln
1               5                   10                  15

Met Asn Ser Leu Arg Ala Glu Asp Thr Ala Ala Tyr Tyr Cys Val Ser
                20                  25                  30

<210> SEQ ID NO 127
<211> LENGTH: 9
<212> TYPE: PRT
<213> ORGANISM: Homo sapiens

<400> SEQUENCE: 127

Pro Ile Met Thr Ser Ala Phe Asp Ile
1               5

<210> SEQ ID NO 128
<211> LENGTH: 11
<212> TYPE: PRT
<213> ORGANISM: Homo sapiens

<400> SEQUENCE: 128

Trp Gly Pro Gly Thr Met Val Thr Val Ser Ser
1               5                   10

<210> SEQ ID NO 129
<211> LENGTH: 22
<212> TYPE: PRT
<213> ORGANISM: Homo sapiens

<400> SEQUENCE: 129

Gln Leu Val Leu Thr Gln Pro Pro Ser Ala Ser Gly Ser Pro Gly Gln
1               5                   10                  15

Ser Val Thr Ile Ser Cys
                20

<210> SEQ ID NO 130
<211> LENGTH: 14
<212> TYPE: PRT
<213> ORGANISM: Homo sapiens

<400> SEQUENCE: 130

Thr Gly Thr Ser Ser Asp Val Gly Gly Ser Asn Phe Val Ser
1               5                   10

<210> SEQ ID NO 131
<211> LENGTH: 15
```

```
<212> TYPE: PRT
<213> ORGANISM: Homo sapiens

<400> SEQUENCE: 131

Trp Tyr Gln His His Pro Gly Lys Ala Pro Lys Leu Met Ile Tyr
1               5                   10                  15

<210> SEQ ID NO 132
<211> LENGTH: 7
<212> TYPE: PRT
<213> ORGANISM: Homo sapiens

<400> SEQUENCE: 132

Glu Val Ser Gln Arg Pro Ser
1               5

<210> SEQ ID NO 133
<211> LENGTH: 32
<212> TYPE: PRT
<213> ORGANISM: Homo sapiens

<400> SEQUENCE: 133

Gly Val Pro Asp Arg Phe Ser Gly Ser Lys Ser Gly Asn Thr Ala Ser
1               5                   10                  15

Leu Thr Val Ser Gly Leu Gln Ala Asp Asp Glu Ala Asp Tyr Tyr Cys
            20                  25                  30

<210> SEQ ID NO 134
<211> LENGTH: 9
<212> TYPE: PRT
<213> ORGANISM: Homo sapiens

<400> SEQUENCE: 134

Ser Ser Tyr Ala Gly Ser Val Val Leu
1               5

<210> SEQ ID NO 135
<211> LENGTH: 10
<212> TYPE: PRT
<213> ORGANISM: Homo sapiens

<400> SEQUENCE: 135

Phe Gly Gly Gly Thr Lys Leu Thr Val Leu
1               5                   10

<210> SEQ ID NO 136
<211> LENGTH: 29
<212> TYPE: PRT
<213> ORGANISM: Homo sapiens

<400> SEQUENCE: 136

Glu Val Gln Leu Val Glu Ser Gly Gly Leu Ala Gln Pro Gly Gly
1               5                   10                  15

Ser Leu Arg Leu Ser Cys Glu Ala Ser Gly Phe His Leu
            20                  25

<210> SEQ ID NO 137
<211> LENGTH: 6
<212> TYPE: PRT
<213> ORGANISM: Homo sapiens

<400> SEQUENCE: 137

Ala Gly Asn Ala Met Ala
1               5
```

```
<210> SEQ ID NO 138
<211> LENGTH: 14
<212> TYPE: PRT
<213> ORGANISM: Homo sapiens

<400> SEQUENCE: 138

Trp Val Arg Gln Ala Pro Gly Lys Gly Leu Glu Trp Val Ala
1               5                   10

<210> SEQ ID NO 139
<211> LENGTH: 17
<212> TYPE: PRT
<213> ORGANISM: Homo sapiens

<400> SEQUENCE: 139

Ala Ile Gly Gly Ser Asp Asp Arg Thr Asp Tyr Ala Asp Ser Val Lys
1               5                   10                  15

Gly

<210> SEQ ID NO 140
<211> LENGTH: 32
<212> TYPE: PRT
<213> ORGANISM: Homo sapiens

<400> SEQUENCE: 140

Arg Phe Thr Ile Ser Arg Asp Lys Ser Lys Asn Thr Leu Ser Leu Gln
1               5                   10                  15

Met Asn Ser Leu Arg Val Glu Asp Thr Ala Val Tyr Tyr Cys Ala Lys
            20                  25                  30

<210> SEQ ID NO 141
<211> LENGTH: 9
<212> TYPE: PRT
<213> ORGANISM: Homo sapiens

<400> SEQUENCE: 141

Asp Ile Trp Arg Trp Ala Phe Asp Tyr
1               5

<210> SEQ ID NO 142
<211> LENGTH: 11
<212> TYPE: PRT
<213> ORGANISM: Homo sapiens

<400> SEQUENCE: 142

Trp Gly Gln Gly Thr Leu Val Ser Val Ser Ser
1               5                   10

<210> SEQ ID NO 143
<211> LENGTH: 23
<212> TYPE: PRT
<213> ORGANISM: Homo sapiens

<400> SEQUENCE: 143

Asp Ile Val Met Thr Gln Ser Pro Ala Thr Leu Ser Leu Ser Pro Gly
1               5                   10                  15

Glu Arg Ala Thr Leu Ser Cys
            20

<210> SEQ ID NO 144
<211> LENGTH: 11
<212> TYPE: PRT
```

-continued

<213> ORGANISM: Homo sapiens

<400> SEQUENCE: 144

Trp Ala Ser Gln Tyr Ile Asn Thr Tyr Val Asn
1               5                   10

<210> SEQ ID NO 145
<211> LENGTH: 15
<212> TYPE: PRT
<213> ORGANISM: Homo sapiens

<400> SEQUENCE: 145

Trp Tyr Gln His Lys Pro Gly Gln Ala Pro Arg Leu Leu Ile Tyr
1               5                   10                  15

<210> SEQ ID NO 146
<211> LENGTH: 7
<212> TYPE: PRT
<213> ORGANISM: Homo sapiens

<400> SEQUENCE: 146

Asp Ala Ser Lys Arg Ala Thr
1               5

<210> SEQ ID NO 147
<211> LENGTH: 32
<212> TYPE: PRT
<213> ORGANISM: Homo sapiens

<400> SEQUENCE: 147

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 148
<211> LENGTH: 9
<212> TYPE: PRT
<213> ORGANISM: Homo sapiens

<400> SEQUENCE: 148

Gln Gln Gly Ser Asn Trp Pro Leu Thr
1               5

<210> SEQ ID NO 149
<211> LENGTH: 10
<212> TYPE: PRT
<213> ORGANISM: Homo sapiens

<400> SEQUENCE: 149

Phe Gly Gln Gly Thr Arg Leu Glu Ile Lys
1               5                   10

<210> SEQ ID NO 150
<211> LENGTH: 29
<212> TYPE: PRT
<213> ORGANISM: Homo sapiens

<400> SEQUENCE: 150

Glu Val Gln Leu Val Glu Ser Gly Gly Gly Leu Val Asn Pro Gly Gly
1               5                   10                  15

Ser Leu Arg Leu Ser Cys Ala Ala Ser Gly Phe Thr Phe
            20                  25

```
<210> SEQ ID NO 151
<211> LENGTH: 6
<212> TYPE: PRT
<213> ORGANISM: Homo sapiens

<400> SEQUENCE: 151

Ser Asn Tyr Ala Met Asn
1               5

<210> SEQ ID NO 152
<211> LENGTH: 14
<212> TYPE: PRT
<213> ORGANISM: Homo sapiens

<400> SEQUENCE: 152

Trp Val Arg Gln Ala Pro Gly Lys Gly Leu Glu Trp Val Ser
1               5                   10

<210> SEQ ID NO 153
<211> LENGTH: 17
<212> TYPE: PRT
<213> ORGANISM: Homo sapiens

<400> SEQUENCE: 153

Ser Ile Ser Arg Ser Gly Asp Tyr Ile Tyr Tyr Ala Asp Ser Leu Lys
1               5                   10                  15

Gly

<210> SEQ ID NO 154
<211> LENGTH: 32
<212> TYPE: PRT
<213> ORGANISM: Homo sapiens

<400> SEQUENCE: 154

Arg Ser Thr Ile Ser Arg Asp Asn Ala Lys Asn Ser Leu Phe Leu Gln
1               5                   10                  15

Met Asn Ser Leu Arg Ala Glu Asp Ser Ala Val Tyr Tyr Cys Ala Arg
                20                  25                  30

<210> SEQ ID NO 155
<211> LENGTH: 19
<212> TYPE: PRT
<213> ORGANISM: Homo sapiens

<400> SEQUENCE: 155

Asp Trp Gly Arg Leu Gly Tyr Cys Ser Ser Asn Asn Cys Pro Asp Ala
1               5                   10                  15

Phe Asp Val

<210> SEQ ID NO 156
<211> LENGTH: 11
<212> TYPE: PRT
<213> ORGANISM: Homo sapiens

<400> SEQUENCE: 156

Trp Gly Gln Gly Thr Arg Val Ser Val Ser Ser
1               5                   10

<210> SEQ ID NO 157
<211> LENGTH: 23
<212> TYPE: PRT
<213> ORGANISM: Homo sapiens
```

```
<400> SEQUENCE: 157

Glu Ile Val Met Thr Gln Ser Pro Ser Phe Val Ser Ala Ser Val Gly
1               5                   10                  15

Asp Arg Val Thr Ile Thr Cys
            20

<210> SEQ ID NO 158
<211> LENGTH: 11
<212> TYPE: PRT
<213> ORGANISM: Homo sapiens

<400> SEQUENCE: 158

Arg Ala Ser Gln Asp Ile Ser Asn Trp Leu Val
1               5                   10

<210> SEQ ID NO 159
<211> LENGTH: 15
<212> TYPE: PRT
<213> ORGANISM: Homo sapiens

<400> SEQUENCE: 159

Trp Tyr Gln Gln Lys Pro Gly Lys Ala Pro Lys Leu Leu Ile Tyr
1               5                   10                  15

<210> SEQ ID NO 160
<211> LENGTH: 7
<212> TYPE: PRT
<213> ORGANISM: Homo sapiens

<400> SEQUENCE: 160

Ala Ser Ser Asn Leu Gln Ser
1               5

<210> SEQ ID NO 161
<211> LENGTH: 32
<212> TYPE: PRT
<213> ORGANISM: Homo sapiens

<400> SEQUENCE: 161

Gly Val Pro Ser Arg Phe Ser Gly Ser Gly Ser Gly Thr Asp Phe Ala
1               5                   10                  15

Leu Thr Ile Ile Ser Leu Gln Pro Glu Asp Phe Ala Thr Tyr Tyr Cys
            20                  25                  30

<210> SEQ ID NO 162
<211> LENGTH: 9
<212> TYPE: PRT
<213> ORGANISM: Homo sapiens

<400> SEQUENCE: 162

Gln Gln Glu Asn Ser Phe Pro Tyr Thr
1               5

<210> SEQ ID NO 163
<211> LENGTH: 10
<212> TYPE: PRT
<213> ORGANISM: Homo sapiens

<400> SEQUENCE: 163

Phe Gly Gln Gly Thr Lys Leu Glu Ile Lys
1               5                   10

<210> SEQ ID NO 164
```

```
<211> LENGTH: 29
<212> TYPE: PRT
<213> ORGANISM: Homo sapiens

<400> SEQUENCE: 164

Gln Val Gln Leu Val Glu Ser Gly Gly Gly Leu Val Gln Pro Gly Gly
1               5                   10                  15

Ser Leu Arg Leu Ser Cys Ser Ala Ser Gln Phe Ile Leu
            20                  25

<210> SEQ ID NO 165
<211> LENGTH: 6
<212> TYPE: PRT
<213> ORGANISM: Homo sapiens

<400> SEQUENCE: 165

Ser Asn Tyr Trp Val His
1               5

<210> SEQ ID NO 166
<211> LENGTH: 14
<212> TYPE: PRT
<213> ORGANISM: Homo sapiens

<400> SEQUENCE: 166

Trp Val Arg Gln Val Pro Gly Glu Gly Leu Val Trp Val Ser
1               5                   10

<210> SEQ ID NO 167
<211> LENGTH: 17
<212> TYPE: PRT
<213> ORGANISM: Homo sapiens

<400> SEQUENCE: 167

Arg Ile Asn Glu Asp Gly Ser Val Thr Ser Tyr Ala Asp Ser Val Lys
1               5                   10                  15

Gly

<210> SEQ ID NO 168
<211> LENGTH: 32
<212> TYPE: PRT
<213> ORGANISM: Homo sapiens

<400> SEQUENCE: 168

Arg Phe Thr Ile Ser Arg Asp Asn Ala Lys Asn Thr Leu Tyr Leu Gln
1               5                   10                  15

Met Asn Ser Leu Arg Val Asp Asp Thr Ala Val Tyr Tyr Cys Val Arg
            20                  25                  30

<210> SEQ ID NO 169
<211> LENGTH: 8
<212> TYPE: PRT
<213> ORGANISM: Homo sapiens

<400> SEQUENCE: 169

Asp Leu Cys Gly Glu Arg Asp Asp
1               5

<210> SEQ ID NO 170
<211> LENGTH: 11
<212> TYPE: PRT
<213> ORGANISM: Homo sapiens

<400> SEQUENCE: 170
```

```
Trp Gly Gln Gly Thr Leu Val Thr Val Ser Ser
1               5                   10
```

<210> SEQ ID NO 171
<211> LENGTH: 23
<212> TYPE: PRT
<213> ORGANISM: Homo sapiens

<400> SEQUENCE: 171

```
Val Ile Trp Met Thr Gln Ser Pro Leu Ser Leu Pro Val Thr Pro Gly
1               5                   10                  15

Glu Ala Ala Ser Ile Ser Cys
            20
```

<210> SEQ ID NO 172
<211> LENGTH: 16
<212> TYPE: PRT
<213> ORGANISM: Homo sapiens

<400> SEQUENCE: 172

```
Arg Ser Ser Gln Ser Leu Leu His Arg Asn Gly Arg Thr Phe Phe Ala
1               5                   10                  15
```

<210> SEQ ID NO 173
<211> LENGTH: 15
<212> TYPE: PRT
<213> ORGANISM: Homo sapiens

<400> SEQUENCE: 173

```
Trp Tyr Leu Gln Lys Pro Gly Gln Ser Pro Gln Ile Leu Ile Tyr
1               5                   10                  15
```

<210> SEQ ID NO 174
<211> LENGTH: 7
<212> TYPE: PRT
<213> ORGANISM: Homo sapiens

<400> SEQUENCE: 174

```
Leu Gly Ser Asn Arg Ala Phe
1               5
```

<210> SEQ ID NO 175
<211> LENGTH: 32
<212> TYPE: PRT
<213> ORGANISM: Homo sapiens

<400> SEQUENCE: 175

```
Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Ile Tyr Tyr Cys
            20                  25                  30
```

<210> SEQ ID NO 176
<211> LENGTH: 9
<212> TYPE: PRT
<213> ORGANISM: Homo sapiens

<400> SEQUENCE: 176

```
Met Gln Gly Leu Gln Thr Pro Tyr Thr
1               5
```

<210> SEQ ID NO 177
<211> LENGTH: 10

```
<212> TYPE: PRT
<213> ORGANISM: Homo sapiens

<400> SEQUENCE: 177

Phe Gly Gln Gly Thr Lys Leu Glu Ile Lys
1               5                   10

<210> SEQ ID NO 178
<211> LENGTH: 29
<212> TYPE: PRT
<213> ORGANISM: Homo sapiens

<400> SEQUENCE: 178

Gln Leu Gln Leu Gln Glu Ser Gly Gly Gly Leu Val Gln Pro Gly Gly
1               5                   10                  15

Ser Leu Arg Leu Ser Cys Ser Ala Ser Gln Phe Ile Leu
            20                  25

<210> SEQ ID NO 179
<211> LENGTH: 6
<212> TYPE: PRT
<213> ORGANISM: Homo sapiens

<400> SEQUENCE: 179

Ser Asn Tyr Trp Val His
1               5

<210> SEQ ID NO 180
<211> LENGTH: 14
<212> TYPE: PRT
<213> ORGANISM: Homo sapiens

<400> SEQUENCE: 180

Trp Val Arg Gln Val Pro Gly Glu Gly Leu Val Trp Val Ser
1               5                   10

<210> SEQ ID NO 181
<211> LENGTH: 17
<212> TYPE: PRT
<213> ORGANISM: Homo sapiens

<400> SEQUENCE: 181

Arg Ile Asn Glu Asp Gly Ser Val Thr Ser Tyr Ala Asp Ser Val Lys
1               5                   10                  15

Gly

<210> SEQ ID NO 182
<211> LENGTH: 32
<212> TYPE: PRT
<213> ORGANISM: Homo sapiens

<400> SEQUENCE: 182

Arg Phe Thr Ile Ser Arg Asp Asn Ala Lys Asn Thr Leu Tyr Leu Gln
1               5                   10                  15

Met Asn Ser Leu Arg Val Asp Asp Thr Ala Val Tyr Tyr Cys Val Arg
            20                  25                  30

<210> SEQ ID NO 183
<211> LENGTH: 8
<212> TYPE: PRT
<213> ORGANISM: Homo sapiens

<400> SEQUENCE: 183
```

Asp Leu Cys Trp Glu Arg Asp Asp
1               5

<210> SEQ ID NO 184
<211> LENGTH: 11
<212> TYPE: PRT
<213> ORGANISM: Homo sapiens

<400> SEQUENCE: 184

Trp Gly Gln Gly Thr Leu Val Ser Val Ser Ser
1               5                   10

<210> SEQ ID NO 185
<211> LENGTH: 23
<212> TYPE: PRT
<213> ORGANISM: Homo sapiens

<400> SEQUENCE: 185

Val Ile Trp Met Thr Gln Ser Pro Leu Ser Leu Pro Val Thr Pro Gly
1               5                   10                  15

Glu Ala Ala Ser Ile Ser Cys
            20

<210> SEQ ID NO 186
<211> LENGTH: 16
<212> TYPE: PRT
<213> ORGANISM: Homo sapiens

<400> SEQUENCE: 186

Arg Ser Ser Gln Ser Leu Leu His Arg Asn Gly Arg Thr Phe Phe Ala
1               5                   10                  15

<210> SEQ ID NO 187
<211> LENGTH: 15
<212> TYPE: PRT
<213> ORGANISM: Homo sapiens

<400> SEQUENCE: 187

Trp Tyr Leu Gln Lys Pro Gly Gln Ser Pro Gln Ile Leu Ile Tyr
1               5                   10                  15

<210> SEQ ID NO 188
<211> LENGTH: 7
<212> TYPE: PRT
<213> ORGANISM: Homo sapiens

<400> SEQUENCE: 188

Leu Gly Ser Asn Arg Ala Phe
1               5

<210> SEQ ID NO 189
<211> LENGTH: 32
<212> TYPE: PRT
<213> ORGANISM: Homo sapiens

<400> SEQUENCE: 189

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Ile Tyr Tyr Cys
            20                  25                  30

<210> SEQ ID NO 190
<211> LENGTH: 9
<212> TYPE: PRT

```
<213> ORGANISM: Homo sapiens

<400> SEQUENCE: 190

Met Gln Gly Leu Gln Thr Pro Tyr Thr
1               5

<210> SEQ ID NO 191
<211> LENGTH: 10
<212> TYPE: PRT
<213> ORGANISM: Homo sapiens

<400> SEQUENCE: 191

Phe Gly Gln Gly Thr Lys Leu Glu Ile Lys
1               5                   10

<210> SEQ ID NO 192
<211> LENGTH: 29
<212> TYPE: PRT
<213> ORGANISM: Homo sapiens

<400> SEQUENCE: 192

Gln Val Gln Leu Val Gln Ser Gly Gly Val Val Gln Pro Gly Gly
1               5                   10                  15

Ser Leu Arg Leu Ser Cys Ala Ala Ser Pro Phe Thr Phe
            20                  25

<210> SEQ ID NO 193
<211> LENGTH: 6
<212> TYPE: PRT
<213> ORGANISM: Homo sapiens

<400> SEQUENCE: 193

Lys Thr Ser Ile Leu His
1               5

<210> SEQ ID NO 194
<211> LENGTH: 14
<212> TYPE: PRT
<213> ORGANISM: Homo sapiens

<400> SEQUENCE: 194

Trp Val Arg Gln Ala Pro Gly Lys Gly Leu Glu Trp Val Ser
1               5                   10

<210> SEQ ID NO 195
<211> LENGTH: 17
<212> TYPE: PRT
<213> ORGANISM: Homo sapiens

<400> SEQUENCE: 195

Ala Met Ser Tyr Asp Gly Phe Ser Lys Tyr Tyr Ala Asp Ser Val Lys
1               5                   10                  15

Gly

<210> SEQ ID NO 196
<211> LENGTH: 32
<212> TYPE: PRT
<213> ORGANISM: Homo sapiens

<400> SEQUENCE: 196

Arg Leu Thr Ile Ser Arg Asp Ser Ser Thr Asn Thr Leu Tyr Leu Glu
1               5                   10                  15

Met Asn Ser Leu Arg Phe Glu Asp Thr Ala Leu Tyr Phe Cys Ala Arg
```

```
                    20                  25                  30
```

<210> SEQ ID NO 197
<211> LENGTH: 13
<212> TYPE: PRT
<213> ORGANISM: Homo sapiens

<400> SEQUENCE: 197

```
Glu Ala Tyr Thr Ser Gly Arg Ala Gly Cys Phe Asn Pro
1               5                   10
```

<210> SEQ ID NO 198
<211> LENGTH: 11
<212> TYPE: PRT
<213> ORGANISM: Homo sapiens

<400> SEQUENCE: 198

```
Trp Gly Gln Gly Val Leu Val Ser Val Ser Ser
1               5                   10
```

<210> SEQ ID NO 199
<211> LENGTH: 23
<212> TYPE: PRT
<213> ORGANISM: Homo sapiens

<400> SEQUENCE: 199

```
Asp Ile Val Met Thr Gln Thr Pro Ser Thr Gln Ser Ala Ser Val Gly
1               5                   10                  15

Asp Arg Val Thr Ile Thr Cys
            20
```

<210> SEQ ID NO 200
<211> LENGTH: 11
<212> TYPE: PRT
<213> ORGANISM: Homo sapiens

<400> SEQUENCE: 200

```
Arg Ala Ser Gln Ser Ile Ser Ile Trp Leu Ala
1               5                   10
```

<210> SEQ ID NO 201
<211> LENGTH: 15
<212> TYPE: PRT
<213> ORGANISM: Homo sapiens

<400> SEQUENCE: 201

```
Trp Tyr Gln Gln Lys Pro Gly Lys Ala Pro Lys Leu Leu Ile His
1               5                   10                  15
```

<210> SEQ ID NO 202
<211> LENGTH: 7
<212> TYPE: PRT
<213> ORGANISM: Homo sapiens

<400> SEQUENCE: 202

```
Asp Ala Ser Thr Leu Glu Ser
1               5
```

<210> SEQ ID NO 203
<211> LENGTH: 32
<212> TYPE: PRT
<213> ORGANISM: Homo sapiens

<400> SEQUENCE: 203

```
Gly Val Pro Ser Arg Phe Ser Gly Ser Gly Ser Gly Thr Glu Phe Thr
1               5                   10                  15

Leu Thr Ile Ser Ser Leu Gln Pro Asp Asp Ser Ala Thr Tyr Tyr Cys
            20                  25                  30
```

<210> SEQ ID NO 204
<211> LENGTH: 9
<212> TYPE: PRT
<213> ORGANISM: Homo sapiens

<400> SEQUENCE: 204

```
Gln Arg Tyr Asn Asp Tyr Pro Pro Thr
1               5
```

<210> SEQ ID NO 205
<211> LENGTH: 10
<212> TYPE: PRT
<213> ORGANISM: Homo sapiens

<400> SEQUENCE: 205

```
Phe Gly Pro Gly Thr Lys Val Glu Ile Lys
1               5                   10
```

<210> SEQ ID NO 206
<211> LENGTH: 28
<212> TYPE: PRT
<213> ORGANISM: Homo sapiens

<400> SEQUENCE: 206

```
Gln Val Leu Lys Glu Ser Gly Gly Val Val Gln Pro Gly Gly Ser
1               5                   10                  15

Leu Arg Leu Ser Cys Ala Ala Ser Pro Phe Thr Phe
            20                  25
```

<210> SEQ ID NO 207
<211> LENGTH: 6
<212> TYPE: PRT
<213> ORGANISM: Homo sapiens

<400> SEQUENCE: 207

```
Glu Thr Ser Ile Leu His
1               5
```

<210> SEQ ID NO 208
<211> LENGTH: 14
<212> TYPE: PRT
<213> ORGANISM: Homo sapiens

<400> SEQUENCE: 208

```
Trp Val Arg Gln Ala Pro Gly Lys Gly Leu Glu Trp Val Ser
1               5                   10
```

<210> SEQ ID NO 209
<211> LENGTH: 17
<212> TYPE: PRT
<213> ORGANISM: Homo sapiens

<400> SEQUENCE: 209

```
Ala Met Ser Tyr Asp Gly Phe Ser Lys Tyr Tyr Ala Asp Ser Val Lys
1               5                   10                  15

Gly
```

<210> SEQ ID NO 210

```
<211> LENGTH: 32
<212> TYPE: PRT
<213> ORGANISM: Homo sapiens

<400> SEQUENCE: 210

Arg Leu Thr Ile Ser Arg Asp Ser Ser Thr Asn Thr Leu Tyr Leu Glu
1               5                   10                  15

Met Asn Ser Leu Arg Phe Glu Asp Thr Ala Leu Tyr Phe Cys Ala Arg
                20                  25                  30

<210> SEQ ID NO 211
<211> LENGTH: 13
<212> TYPE: PRT
<213> ORGANISM: Homo sapiens

<400> SEQUENCE: 211

Glu Ala Tyr Thr Ser Gly Arg Ala Gly Cys Phe Asp Pro
1               5                   10

<210> SEQ ID NO 212
<211> LENGTH: 11
<212> TYPE: PRT
<213> ORGANISM: Homo sapiens

<400> SEQUENCE: 212

Trp Gly Gln Gly Val Leu Val Ser Val Ser Ser
1               5                   10

<210> SEQ ID NO 213
<211> LENGTH: 23
<212> TYPE: PRT
<213> ORGANISM: Homo sapiens

<400> SEQUENCE: 213

Glu Ile Val Met Thr Gln Ser Pro Ser Thr Gln Ser Ala Ser Val Gly
1               5                   10                  15

Asp Arg Val Thr Ile Thr Cys
                20

<210> SEQ ID NO 214
<211> LENGTH: 11
<212> TYPE: PRT
<213> ORGANISM: Homo sapiens

<400> SEQUENCE: 214

Arg Ala Ser Gln Ser Ile Ser Ile Trp Leu Ala
1               5                   10

<210> SEQ ID NO 215
<211> LENGTH: 15
<212> TYPE: PRT
<213> ORGANISM: Homo sapiens

<400> SEQUENCE: 215

Trp Tyr Gln Gln Lys Pro Gly Lys Ala Pro Lys Leu Leu Ile His
1               5                   10                  15

<210> SEQ ID NO 216
<211> LENGTH: 7
<212> TYPE: PRT
<213> ORGANISM: Homo sapiens

<400> SEQUENCE: 216

Asp Ala Ser Thr Leu Glu Ser
```

<210> SEQ ID NO 217
<211> LENGTH: 32
<212> TYPE: PRT
<213> ORGANISM: Homo sapiens

<400> SEQUENCE: 217

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Ser Ala Thr Tyr Tyr Cys
            20                  25                  30

<210> SEQ ID NO 218
<211> LENGTH: 9
<212> TYPE: PRT
<213> ORGANISM: Homo sapiens

<400> SEQUENCE: 218

Gln Arg Tyr Asn Asp Tyr Pro Pro Thr
1               5

<210> SEQ ID NO 219
<211> LENGTH: 10
<212> TYPE: PRT
<213> ORGANISM: Homo sapiens

<400> SEQUENCE: 219

Phe Gly Pro Gly Thr Lys Val Glu Ile Lys
1               5                   10

<210> SEQ ID NO 220
<211> LENGTH: 29
<212> TYPE: PRT
<213> ORGANISM: Homo sapiens

<400> SEQUENCE: 220

Glu Val Gln Leu Val Glu Ser Gly Gly Gly Leu Val Gln Pro Gly Gly
1               5                   10                  15

Ser Leu Arg Val Ser Cys Ala Ala Ser Gly Phe Thr Leu
            20                  25

<210> SEQ ID NO 221
<211> LENGTH: 6
<212> TYPE: PRT
<213> ORGANISM: Homo sapiens

<400> SEQUENCE: 221

Asn Thr Tyr Trp Met His
1               5

<210> SEQ ID NO 222
<211> LENGTH: 14
<212> TYPE: PRT
<213> ORGANISM: Homo sapiens

<400> SEQUENCE: 222

Trp Val Arg Gln Ala Pro Gly Lys Gly Leu Val Trp Val Ser
1               5                   10

<210> SEQ ID NO 223
<211> LENGTH: 17
<212> TYPE: PRT
<213> ORGANISM: Homo sapiens

```
<400> SEQUENCE: 223

Arg Ile Asn Glu Asp Gly Thr Thr Ile Ser Tyr Ala Asp Ser Val Arg
1               5                   10                  15

Gly

<210> SEQ ID NO 224
<211> LENGTH: 32
<212> TYPE: PRT
<213> ORGANISM: Homo sapiens

<400> SEQUENCE: 224

Arg Phe Thr Ile Ser Arg Asp Asn Ala Glu Asn Thr Leu Tyr Leu Gln
1               5                   10                  15

Met His Ser Leu Arg Ala Glu Asp Thr Gly Val Tyr Tyr Cys Ala Arg
            20                  25                  30

<210> SEQ ID NO 225
<211> LENGTH: 8
<212> TYPE: PRT
<213> ORGANISM: Homo sapiens

<400> SEQUENCE: 225

Asp Phe Thr Gly Pro Phe Asp Ser
1               5

<210> SEQ ID NO 226
<211> LENGTH: 11
<212> TYPE: PRT
<213> ORGANISM: Homo sapiens

<400> SEQUENCE: 226

Trp Gly Gln Gly Thr Leu Val Ser Val Ser Ser
1               5                   10

<210> SEQ ID NO 227
<211> LENGTH: 22
<212> TYPE: PRT
<213> ORGANISM: Homo sapiens

<400> SEQUENCE: 227

Gln Ser Val Leu Thr Gln Pro Pro Ser Val Ser Gly Thr Pro Gly Gln
1               5                   10                  15

Arg Val Thr Ile Ser Cys
            20

<210> SEQ ID NO 228
<211> LENGTH: 13
<212> TYPE: PRT
<213> ORGANISM: Homo sapiens

<400> SEQUENCE: 228

Ser Gly Ser Asn Ser Asn Ala Gly Arg Asp Tyr Val Ser
1               5                   10

<210> SEQ ID NO 229
<211> LENGTH: 15
<212> TYPE: PRT
<213> ORGANISM: Homo sapiens

<400> SEQUENCE: 229

Trp Tyr Gln Gln Val Pro Gly Thr Ala Pro Lys Leu Leu Ile Tyr
1               5                   10                  15
```

<210> SEQ ID NO 230
<211> LENGTH: 7
<212> TYPE: PRT
<213> ORGANISM: Homo sapiens

<400> SEQUENCE: 230

Lys Asn Asn Gln Arg Pro Ser
1               5

<210> SEQ ID NO 231
<211> LENGTH: 32
<212> TYPE: PRT
<213> ORGANISM: Homo sapiens

<400> SEQUENCE: 231

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Asp Gly Asp Tyr Tyr Cys
            20                  25                  30

<210> SEQ ID NO 232
<211> LENGTH: 11
<212> TYPE: PRT
<213> ORGANISM: Homo sapiens

<400> SEQUENCE: 232

Ile Val Trp Asp Gly Ser Leu Ser Gly Tyr Val
1               5                   10

<210> SEQ ID NO 233
<211> LENGTH: 10
<212> TYPE: PRT
<213> ORGANISM: Homo sapiens

<400> SEQUENCE: 233

Phe Gly Thr Gly Thr Lys Val Thr Val Leu
1               5                   10

<210> SEQ ID NO 234
<211> LENGTH: 29
<212> TYPE: PRT
<213> ORGANISM: Homo sapiens

<400> SEQUENCE: 234

Gln Leu Gln Leu Gln Glu Ser Gly Gly Leu Val Gln Pro Gly Gly
1               5                   10                  15

Ser Leu Arg Leu Ser Cys Val Val Ser Gly Phe Thr Phe
            20                  25

<210> SEQ ID NO 235
<211> LENGTH: 6
<212> TYPE: PRT
<213> ORGANISM: Homo sapiens

<400> SEQUENCE: 235

Ser Ser His Ala Met Ser
1               5

<210> SEQ ID NO 236
<211> LENGTH: 14
<212> TYPE: PRT
<213> ORGANISM: Homo sapiens

<400> SEQUENCE: 236

Trp Val Arg Gln Ala Pro Gly Lys Gly Leu Glu Trp Val Ser
1               5                   10

<210> SEQ ID NO 237
<211> LENGTH: 17
<212> TYPE: PRT
<213> ORGANISM: Homo sapiens

<400> SEQUENCE: 237

Ser Ile Ser Ile Ser Gly Gly Asp Thr Phe Tyr Ala Asp Ser Val Arg
1               5                   10                  15

Gly

<210> SEQ ID NO 238
<211> LENGTH: 32
<212> TYPE: PRT
<213> ORGANISM: Homo sapiens

<400> SEQUENCE: 238

Arg Phe Thr Ile Phe Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Thr
            20                  25                  30

<210> SEQ ID NO 239
<211> LENGTH: 7
<212> TYPE: PRT
<213> ORGANISM: Homo sapiens

<400> SEQUENCE: 239

Glu Thr Ser Pro Asn Asp Tyr
1               5

<210> SEQ ID NO 240
<211> LENGTH: 11
<212> TYPE: PRT
<213> ORGANISM: Homo sapiens

<400> SEQUENCE: 240

Trp Gly Gln Gly Thr Leu Val Ser Val Ser Ser
1               5                   10

<210> SEQ ID NO 241
<211> LENGTH: 22
<212> TYPE: PRT
<213> ORGANISM: Homo sapiens

<400> SEQUENCE: 241

Ser Tyr Glu Leu Thr Gln Pro Ser Ser Leu Thr Val Ser Pro Gly Gly
1               5                   10                  15

Thr Val Thr Leu Thr Cys
            20

<210> SEQ ID NO 242
<211> LENGTH: 14
<212> TYPE: PRT
<213> ORGANISM: Homo sapiens

<400> SEQUENCE: 242

Gly Leu Ser Ser Gly Ala Val Thr Ser Gly His Tyr Pro Tyr
1               5                   10

<210> SEQ ID NO 243
<211> LENGTH: 15
<212> TYPE: PRT
<213> ORGANISM: Homo sapiens

<400> SEQUENCE: 243

Trp Phe Gln Gln Lys Pro Gly Gln Ala Pro Lys Thr Leu Ile Phe
1               5                   10                  15

<210> SEQ ID NO 244
<211> LENGTH: 7
<212> TYPE: PRT
<213> ORGANISM: Homo sapiens

<400> SEQUENCE: 244

Asp Thr Ser Arg Lys His Ser
1               5

<210> SEQ ID NO 245
<211> LENGTH: 32
<212> TYPE: PRT
<213> ORGANISM: Homo sapiens

<400> SEQUENCE: 245

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Ala Asp Tyr Tyr Cys
            20                  25                  30

<210> SEQ ID NO 246
<211> LENGTH: 9
<212> TYPE: PRT
<213> ORGANISM: Homo sapiens

<400> SEQUENCE: 246

Leu Leu Ala Cys Asn Gly Ala Cys Val
1               5

<210> SEQ ID NO 247
<211> LENGTH: 10
<212> TYPE: PRT
<213> ORGANISM: Homo sapiens

<400> SEQUENCE: 247

Phe Gly Gly Gly Thr Lys Leu Thr Val Leu
1               5                   10

<210> SEQ ID NO 248
<211> LENGTH: 29
<212> TYPE: PRT
<213> ORGANISM: Homo sapiens

<400> SEQUENCE: 248

Glu Val Gln Leu Val Glu Thr Gly Gly Gly Leu Val Gln Pro Gly Gly
1               5                   10                  15

Ser Leu Arg Leu Ser Cys Val Val Ser Gly Phe Thr Phe
            20                  25

<210> SEQ ID NO 249
<211> LENGTH: 6
<212> TYPE: PRT
<213> ORGANISM: Homo sapiens

<400> SEQUENCE: 249

```
Ser Ser His Ala Met Ser
1               5

<210> SEQ ID NO 250
<211> LENGTH: 14
<212> TYPE: PRT
<213> ORGANISM: Homo sapiens

<400> SEQUENCE: 250

Trp Val Arg Gln Ala Pro Gly Lys Gly Leu Glu Trp Val Ser
1               5                   10

<210> SEQ ID NO 251
<211> LENGTH: 17
<212> TYPE: PRT
<213> ORGANISM: Homo sapiens

<400> SEQUENCE: 251

Ser Ile Ser Ile Ser Gly Gly Asp Thr Phe Tyr Ala Asp Ser Val Arg
1               5                   10                  15

Gly

<210> SEQ ID NO 252
<211> LENGTH: 32
<212> TYPE: PRT
<213> ORGANISM: Homo sapiens

<400> SEQUENCE: 252

Arg Phe Thr Ile Phe Arg Asp Asn Ser Lys Asn Thr Val Tyr Leu Gln
1               5                   10                  15

Met Asn Ser Leu Arg Ala Glu Asp Thr Ala Val Tyr Tyr Cys Ala Thr
            20                  25                  30

<210> SEQ ID NO 253
<211> LENGTH: 7
<212> TYPE: PRT
<213> ORGANISM: Homo sapiens

<400> SEQUENCE: 253

Glu Thr Ser Pro Asn Asp Tyr
1               5

<210> SEQ ID NO 254
<211> LENGTH: 11
<212> TYPE: PRT
<213> ORGANISM: Homo sapiens

<400> SEQUENCE: 254

Trp Gly Gln Gly Thr Leu Val Thr Val Ser Ser
1               5                   10

<210> SEQ ID NO 255
<211> LENGTH: 22
<212> TYPE: PRT
<213> ORGANISM: Homo sapiens

<400> SEQUENCE: 255

Ser Tyr Glu Leu Thr Gln Pro Ser Ser Leu Thr Val Ser Pro Gly Gly
1               5                   10                  15

Thr Val Thr Leu Thr Cys
            20
```

-continued

```
<210> SEQ ID NO 256
<211> LENGTH: 14
<212> TYPE: PRT
<213> ORGANISM: Homo sapiens

<400> SEQUENCE: 256

Gly Leu Ser Ser Gly Ala Val Thr Ser Gly His Tyr Pro Tyr
1               5                   10

<210> SEQ ID NO 257
<211> LENGTH: 15
<212> TYPE: PRT
<213> ORGANISM: Homo sapiens

<400> SEQUENCE: 257

Trp Phe Gln Gln Lys Pro Gly Gln Ala Pro Lys Thr Leu Ile Phe
1               5                   10                  15

<210> SEQ ID NO 258
<211> LENGTH: 7
<212> TYPE: PRT
<213> ORGANISM: Homo sapiens

<400> SEQUENCE: 258

Asp Thr Ser Arg Lys His Ser
1               5

<210> SEQ ID NO 259
<211> LENGTH: 32
<212> TYPE: PRT
<213> ORGANISM: Homo sapiens

<400> SEQUENCE: 259

Trp Thr Pro Ala Arg Phe Ser Gly Ser Leu Leu Gly Gly Lys Ala Ala
1               5                   10                  15

Leu Thr Leu Ser Gly Ala Gln Pro Glu Asp Asp Ala Asp Tyr Tyr Cys
            20                  25                  30

<210> SEQ ID NO 260
<211> LENGTH: 9
<212> TYPE: PRT
<213> ORGANISM: Homo sapiens

<400> SEQUENCE: 260

Leu Leu Ala Cys Asn Gly Ala Cys Val
1               5

<210> SEQ ID NO 261
<211> LENGTH: 10
<212> TYPE: PRT
<213> ORGANISM: Homo sapiens

<400> SEQUENCE: 261

Phe Gly Gly Gly Thr Lys Leu Thr Val Leu
1               5                   10

<210> SEQ ID NO 262
<211> LENGTH: 29
<212> TYPE: PRT
<213> ORGANISM: Homo sapiens

<400> SEQUENCE: 262

Glu Val Gln Leu Val Glu Ser Gly Gly Gly Leu Val Gln Pro Gly Gly
1               5                   10                  15
```

```
Ser Leu Arg Val Ser Cys Ala Ala Ser Gly Phe Thr Leu
            20                  25
```

<210> SEQ ID NO 263
<211> LENGTH: 6
<212> TYPE: PRT
<213> ORGANISM: Homo sapiens

<400> SEQUENCE: 263

```
Asn Thr Tyr Trp Met His
1               5
```

<210> SEQ ID NO 264
<211> LENGTH: 14
<212> TYPE: PRT
<213> ORGANISM: Homo sapiens

<400> SEQUENCE: 264

```
Trp Val Arg Gln Ala Pro Gly Lys Gly Leu Val Trp Val Ser
1               5                   10
```

<210> SEQ ID NO 265
<211> LENGTH: 17
<212> TYPE: PRT
<213> ORGANISM: Homo sapiens

<400> SEQUENCE: 265

```
Arg Ile Asn Glu Asp Gly Thr Thr Ile Ser Tyr Ala Asp Ser Val Arg
1               5                   10                  15

Gly
```

<210> SEQ ID NO 266
<211> LENGTH: 32
<212> TYPE: PRT
<213> ORGANISM: Homo sapiens

<400> SEQUENCE: 266

```
Arg Phe Thr Ile Ser Arg Asp Asn Ala Glu Asn Thr Leu Tyr Leu Gln
1               5                   10                  15

Met His Ser Leu Arg Ala Glu Asp Thr Gly Val Tyr Tyr Cys Ala Arg
            20                  25                  30
```

<210> SEQ ID NO 267
<211> LENGTH: 8
<212> TYPE: PRT
<213> ORGANISM: Homo sapiens

<400> SEQUENCE: 267

```
Asp Phe Thr Gly Pro Phe Asp Ser
1               5
```

<210> SEQ ID NO 268
<211> LENGTH: 11
<212> TYPE: PRT
<213> ORGANISM: Homo sapiens

<400> SEQUENCE: 268

```
Trp Gly Gln Gly Thr Leu Val Ser Val Ser Ser
1               5                   10
```

<210> SEQ ID NO 269
<211> LENGTH: 22
<212> TYPE: PRT
<213> ORGANISM: Homo sapiens -continued

<400> SEQUENCE: 269

Gln Ser Val Leu Thr Gln Pro Pro Ser Val Ser Gly Thr Pro Gly Gln
1               5                   10                  15

Arg Val Thr Ile Ser Cys
            20

<210> SEQ ID NO 270
<211> LENGTH: 13
<212> TYPE: PRT
<213> ORGANISM: Homo sapiens

<400> SEQUENCE: 270

Ser Gly Ser Asn Ser Asn Val Gly Arg Asp Tyr Val Ser
1               5                   10

<210> SEQ ID NO 271
<211> LENGTH: 15
<212> TYPE: PRT
<213> ORGANISM: Homo sapiens

<400> SEQUENCE: 271

Trp Tyr Gln Gln Val Pro Gly Thr Ala Pro Lys Leu Leu Ile Tyr
1               5                   10                  15

<210> SEQ ID NO 272
<211> LENGTH: 7
<212> TYPE: PRT
<213> ORGANISM: Homo sapiens

<400> SEQUENCE: 272

Lys Asn Asn Arg Arg Pro Ser
1               5

<210> SEQ ID NO 273
<211> LENGTH: 32
<212> TYPE: PRT
<213> ORGANISM: Homo sapiens

<400> SEQUENCE: 273

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Asp Gly Asp Tyr Tyr Cys
            20                  25                  30

<210> SEQ ID NO 274
<211> LENGTH: 11
<212> TYPE: PRT
<213> ORGANISM: Homo sapiens

<400> SEQUENCE: 274

Ile Val Trp Asp Gly Ser Leu Ser Gly Tyr Val
1               5                   10

<210> SEQ ID NO 275
<211> LENGTH: 10
<212> TYPE: PRT
<213> ORGANISM: Homo sapiens

<400> SEQUENCE: 275

Phe Gly Thr Gly Thr Lys Val Thr Val Leu
1               5                   10

```
<210> SEQ ID NO 276
<211> LENGTH: 29
<212> TYPE: PRT
<213> ORGANISM: Homo sapiens

<400> SEQUENCE: 276

Glu Val Gln Leu Val Glu Ser Gly Gly Gly Leu Val Gln Pro Gly Gly
1               5                   10                  15

Ser Leu Arg Val Ser Cys Ala Ala Ser Gly Phe Thr Leu
            20                  25

<210> SEQ ID NO 277
<211> LENGTH: 6
<212> TYPE: PRT
<213> ORGANISM: Homo sapiens

<400> SEQUENCE: 277

Asn Thr Tyr Trp Met His
1               5

<210> SEQ ID NO 278
<211> LENGTH: 14
<212> TYPE: PRT
<213> ORGANISM: Homo sapiens

<400> SEQUENCE: 278

Trp Val Arg Gln Ala Pro Gly Lys Gly Leu Val Trp Val Ser
1               5                   10

<210> SEQ ID NO 279
<211> LENGTH: 17
<212> TYPE: PRT
<213> ORGANISM: Homo sapiens

<400> SEQUENCE: 279

Arg Ile Asn Glu Asp Gly Thr Thr Ile Ser Tyr Ala Asp Ser Val Arg
1               5                   10                  15

Gly

<210> SEQ ID NO 280
<211> LENGTH: 32
<212> TYPE: PRT
<213> ORGANISM: Homo sapiens

<400> SEQUENCE: 280

Arg Phe Thr Ile Ser Arg Asp Asn Ala Glu Asn Thr Leu Tyr Leu Gln
1               5                   10                  15

Met His Ser Leu Arg Ala Glu Asp Thr Gly Val Tyr Tyr Cys Ala Arg
            20                  25                  30

<210> SEQ ID NO 281
<211> LENGTH: 8
<212> TYPE: PRT
<213> ORGANISM: Homo sapiens

<400> SEQUENCE: 281

Asp Phe Thr Gly Pro Phe Asp Ser
1               5

<210> SEQ ID NO 282
<211> LENGTH: 11
<212> TYPE: PRT
<213> ORGANISM: Homo sapiens
```

```
<400> SEQUENCE: 282

Trp Gly Gln Gly Thr Leu Val Ser Val Ser Ser
1               5                   10

<210> SEQ ID NO 283
<211> LENGTH: 22
<212> TYPE: PRT
<213> ORGANISM: Homo sapiens

<400> SEQUENCE: 283

Gln Leu Val Leu Thr Gln Pro Pro Ser Val Ser Gly Thr Pro Gly Gln
1               5                   10                  15

Arg Val Thr Ile Ser Cys
            20

<210> SEQ ID NO 284
<211> LENGTH: 13
<212> TYPE: PRT
<213> ORGANISM: Homo sapiens

<400> SEQUENCE: 284

Ser Gly Ser Asn Ser Asn Val Gly Arg Asp Tyr Val Ser
1               5                   10

<210> SEQ ID NO 285
<211> LENGTH: 15
<212> TYPE: PRT
<213> ORGANISM: Homo sapiens

<400> SEQUENCE: 285

Trp Tyr Gln Gln Val Pro Gly Thr Ala Pro Lys Leu Leu Ile Tyr
1               5                   10                  15

<210> SEQ ID NO 286
<211> LENGTH: 7
<212> TYPE: PRT
<213> ORGANISM: Homo sapiens

<400> SEQUENCE: 286

Lys Asn Asn Gln Arg Pro Ser
1               5

<210> SEQ ID NO 287
<211> LENGTH: 32
<212> TYPE: PRT
<213> ORGANISM: Homo sapiens

<400> SEQUENCE: 287

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Asp Gly Asp Tyr Tyr Cys
            20                  25                  30

<210> SEQ ID NO 288
<211> LENGTH: 11
<212> TYPE: PRT
<213> ORGANISM: Homo sapiens

<400> SEQUENCE: 288

Ile Val Trp Asp Gly Ser Leu Ser Gly Tyr Val
1               5                   10

<210> SEQ ID NO 289
```

```
<211> LENGTH: 10
<212> TYPE: PRT
<213> ORGANISM: Homo sapiens

<400> SEQUENCE: 289

Phe Gly Thr Gly Thr Lys Val Thr Val Leu
1               5                   10

<210> SEQ ID NO 290
<211> LENGTH: 8
<212> TYPE: PRT
<213> ORGANISM: Homo sapiens

<400> SEQUENCE: 290

Asp Leu Ala Gly Glu Arg Asp Asp
1               5

<210> SEQ ID NO 291
<211> LENGTH: 8
<212> TYPE: PRT
<213> ORGANISM: Homo sapiens

<400> SEQUENCE: 291

Asp Leu Ser Gly Glu Arg Asp Asp
1               5

<210> SEQ ID NO 292
<211> LENGTH: 19
<212> TYPE: PRT
<213> ORGANISM: Homo sapiens

<400> SEQUENCE: 292

Asp Trp Gly Arg Leu Gly Tyr Trp Ser Ser Asn Asn Tyr Pro Asp Ala
1               5                   10                  15

Phe Asp Val

<210> SEQ ID NO 293
<211> LENGTH: 19
<212> TYPE: PRT
<213> ORGANISM: Homo sapiens

<400> SEQUENCE: 293

Asp Trp Gly Arg Leu Gly Tyr Ala Ser Ser Asn Asn Ala Pro Asp Ala
1               5                   10                  15

Phe Asp Val

<210> SEQ ID NO 294
<211> LENGTH: 13
<212> TYPE: PRT
<213> ORGANISM: Homo sapiens

<400> SEQUENCE: 294

Glu Ala Tyr Thr Ser Gly Arg Ala Gly Trp Phe Asn Pro
1               5                   10

<210> SEQ ID NO 295
<211> LENGTH: 13
<212> TYPE: PRT
<213> ORGANISM: Homo sapiens

<400> SEQUENCE: 295

Glu Ala Tyr Thr Ser Gly Arg Ala Gly Ala Phe Asn Pro
1               5                   10
```

<210> SEQ ID NO 296
<211> LENGTH: 13
<212> TYPE: PRT
<213> ORGANISM: Homo sapiens

<400> SEQUENCE: 296

Glu Ala Tyr Thr Ser Gly Arg Ala Gly Trp Phe Asp Pro
1               5                   10

<210> SEQ ID NO 297
<211> LENGTH: 13
<212> TYPE: PRT
<213> ORGANISM: Homo sapiens

<400> SEQUENCE: 297

Glu Ala Tyr Thr Ser Gly Arg Ala Gly Ala Phe Asp Pro
1               5                   10

<210> SEQ ID NO 298
<211> LENGTH: 8
<212> TYPE: PRT
<213> ORGANISM: Homo sapiens

<400> SEQUENCE: 298

Asp Leu Trp Gly Glu Arg Asp Asp
1               5

<210> SEQ ID NO 299
<211> LENGTH: 8
<212> TYPE: PRT
<213> ORGANISM: Homo sapiens

<400> SEQUENCE: 299

Asp Leu Ala Gly Glu Arg Asp Asp
1               5

<210> SEQ ID NO 300
<211> LENGTH: 9
<212> TYPE: PRT
<213> ORGANISM: Homo sapiens

<400> SEQUENCE: 300

Leu Leu Ala Tyr Asn Gly Ala Trp Val
1               5

<210> SEQ ID NO 301
<211> LENGTH: 9
<212> TYPE: PRT
<213> ORGANISM: Homo sapiens

<400> SEQUENCE: 301

Leu Leu Ala Ala Asn Gly Ala Ala Val
1               5

<210> SEQ ID NO 302
<211> LENGTH: 9
<212> TYPE: PRT
<213> ORGANISM: Homo sapiens

<400> SEQUENCE: 302

Leu Leu Ala Tyr Asn Gly Ala Trp Val
1               5

<210> SEQ ID NO 303

```
<211> LENGTH: 9
<212> TYPE: PRT
<213> ORGANISM: Homo sapiens

<400> SEQUENCE: 303

Leu Leu Ala Ala Asn Gly Ala Ala Val
1               5
```